United States Patent
Pulst et al.

(10) Patent No.: US 9,920,333 B2
(45) Date of Patent: *Mar. 20, 2018

(54) METHOD OF MAKING INDUCED PLURIPOTENT STEM CELLS

(71) Applicant: University of Utah Research Foundation, Salt Lake City, UT (US)

(72) Inventors: Stefan M. Pulst, Salt Lake City, UT (US); Sharan Paul, Salt Lake City, UT (US); Warunee Dansithong, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/984,861

(22) Filed: Dec. 30, 2015

(65) Prior Publication Data

US 2016/0222411 A1 Aug. 4, 2016

Related U.S. Application Data

(60) Division of application No. 13/975,004, filed on Aug. 23, 2013, now Pat. No. 9,228,204, which is a continuation-in-part of application No. 13/960,305, filed on Aug. 6, 2013, now abandoned, which is a continuation of application No. PCT/US2012/025117, filed on Feb. 14, 2012.

(60) Provisional application No. 61/442,695, filed on Feb. 14, 2011.

(51) Int. Cl.
| | |
|---|---|
| *C12N 5/00* | (2006.01) |
| *C12N 15/86* | (2006.01) |
| *C12N 5/074* | (2010.01) |
| *C12N 5/0793* | (2010.01) |
| *C12N 15/85* | (2006.01) |

(52) U.S. Cl.
CPC ............ *C12N 15/86* (2013.01); *C12N 5/0619* (2013.01); *C12N 5/0696* (2013.01); *C12N 15/85* (2013.01); *C12N 2501/602* (2013.01); *C12N 2501/603* (2013.01); *C12N 2501/604* (2013.01); *C12N 2501/606* (2013.01); *C12N 2510/00* (2013.01); *C12N 2710/10043* (2013.01); *C12N 2710/10343* (2013.01)

(58) Field of Classification Search
USPC .................................................. 435/325, 455
See application file for complete search history.

(56) References Cited

PUBLICATIONS

Takahashi (Cell, 2006, vol. 126:663-676).*
Yu (Science, 2007, vol. 318, p. 1917-1920).*
Nakagawa (Nat Biotechnol, Jan. 2008, vol. 26: 101-106; published online Nov. 11, 2007).*
Okita (Science, Nov. 7, 2008, vol. 322, p. 949-953).*
Feng (Cell Stem Cell, Apr. 3, 2009, vol. 4, p. 301-312).*
Shao (Expert Opin. Biol. Ther., Feb. 2010, vol. 10, No. 1, p. 231-242).*
Aoi (Science, Aug. 1, 2008, vol. 321, No. 5889, p. 699-702, available online Feb. 14, 2008).*
Aasen (Nature Biotech., Nov. 2008, vol. 26, No. 11, p. 1276-1284).*
Sugii (PNAS, Feb. 23, 2010, vol. 107, No. 8, p. 3558-3563).*
Stadtfeld (Cell Stem Cell, Mar. 6, 2008, vol. 2, p. 230-240; published online Feb. 14, 2008).*
Carey (PNAS, 2009, vol. 106, p. 157-162).*
Carey (Nature Methods, Jan. 2010, vol. 7, No. 1, p. 46-59).*
Sommer (Stem Cells, 2009, 27, 543-549).*
Kaji (Nature, Apr. 9, 2009, vol. 458, p. 771-776).*
Gonzalez (PNAS, Jun. 2, 2009, vol. 106, No. 22, p. 8918-8922).*
Paul (Annals of Neurol., 2012, vol. 72, Suppl. 16, pp. S103).*
Toes (PNAS, Dec. 1997, vol. 94, p. 14660-14665).*

* cited by examiner

*Primary Examiner* — Michael C Wilson
(74) *Attorney, Agent, or Firm* — Thorpe North and Western, LLP; David W. Osborne

(57) ABSTRACT

Systems, constructs, and methods for reprogramming cells are provided. In one aspect, for example, a transformation construct for generating iPS cells can include an expression vector having a plurality of reprogramming factors, each reprogramming factor being under control of a separate promoter.

10 Claims, 15 Drawing Sheets

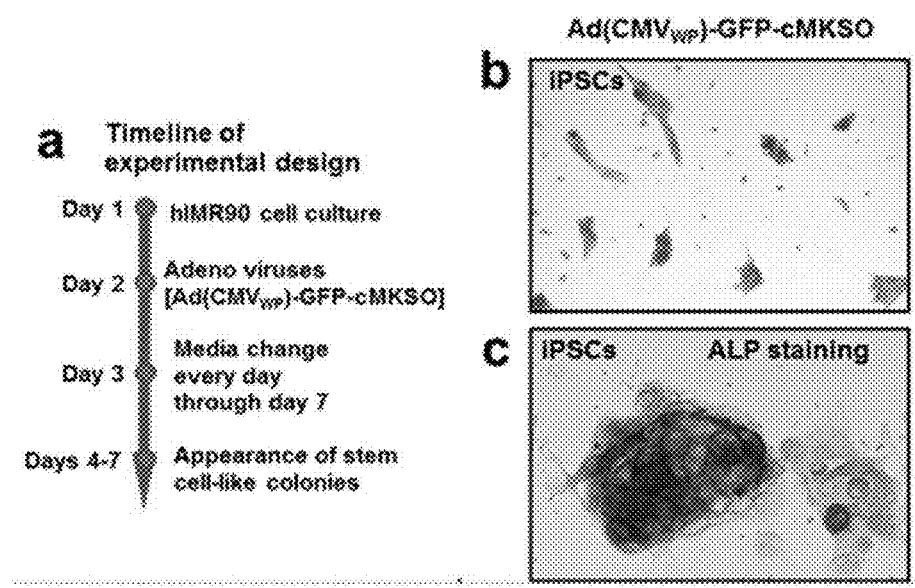
FIG. 18A-C
pAd-GFP-KcMOS
K: KLF4, cM: c-MYC, O: OCT3/4 and S: SOX2
FIG. 19

METHOD OF MAKING INDUCED PLURIPOTENT STEM CELLS

PRIORITY DATA

This application is a divisional of U.S. patent application Ser. No. 13/975,004, filed on Aug. 23, 2013, now issued as U.S. Pat. No. 9,228,204, which is a continuation-in-part of U.S. patent application Ser. No. 13/960,305, filed on Aug. 6, 2013, which is a continuation of Patent Cooperation Treaty Patent Application Serial No. PCT/US2012/025117, filed on Feb. 14, 2012, which claims the benefit of U.S. Provisional Patent Application Ser. No. 61/442,695, filed on Feb. 14, 2011, all of which are incorporated herein by reference.

GOVERNMENT INTEREST

This invention was made with government support under grant numbers RO1NS33123 and RC4NS073009 from the National Institutes of Neurological Disorders and Stroke. The United States government has certain rights to this invention.

BACKGROUND

Current protocols for the generation of induced pluripotent stem (iPS) cells from somatic cells are slow (e.g. 30-45 days) and are inefficient (<0.1% of cells are reprogrammed). Additionally, the generation of iPS cells from somatic cells achieved by simultaneous viral transduction of defined reprogramming transcription factors using Lenti- or Retro- or Adeno-viruses requires multiple viral vectors for gene delivery. Lenti- or Retro-viruses can also result in insertional mutagenesis and can present significant barriers to research, clinical, and therapeutic application of iPS cells. A single gene delivery system does not ensure the infectivity and co-expression of all genes in one cell which is critical for reprogramming. Despite the progress in embryonic stem (ES) cells research in recent years, feeder cells such as inactivated mouse embryonic fibroblasts (iMEF) are still required to generate iPS cells from human or mouse fibroblasts. Feeder cells provide the essential support and nutrients to allow ES/iPS cells to grow, attach, and proliferate. The risk of contamination of viruses or other macromolecules from the mouse cells limits the use of such iPS cells for therapeutic purposes.

SUMMARY

The present disclosure provides systems, constructs, and methods for reprogramming cells. In one aspect, for example, a transformation construct for generating iPS cells can include an expression vector having a plurality of reprogramming factors, where each reprogramming factor is under control of a separate promoter. In one aspect, the expression vector can be selected from plasmids, viruses, and combinations thereof. In another aspect, the expression vector can be selected from adenoviral vectors, episomal vectors, retroviral vectors, and lentiviral vectors. In one specific aspect the expression vector can be an episomal vector.

Various reprogramming factors are contemplated for use in aspects of the present invention. In one aspect, for example, the plurality of reprogramming factors can include OCT3/4, SOX2, and at least one member selected from KLF4, c-Myc, NANOG, or LIN28. In another aspect, the plurality of reprogramming factors can include OCT3/4, SOX2, KLF4, and c-Myc. In yet another aspect, the plurality of reprogramming factors can consist of OCT3/4, SOX2, and KLF4. In a further aspect, the plurality of reprogramming factors includes OCT3/4, SOX2, NANOG, and LIN28. Furthermore, in one aspect, the expression vector can have a sequence that is at least 80% homologous to SEQ ID 72. In yet another aspect, the expression vector has a sequence that is at least 95% homologous to SEQ ID 72. In a further aspect, the expression vector has the sequence of SEQ ID 72.

Various promoters and/or sets of promoters are contemplated, and any appropriate promoter is considered to be within the present scope. In one aspect, for example, at least one of the reprogramming factors is under the control of a CMV promoter. In another aspect, the CMV promoter is a weak CMV promoter. Furthermore, in various aspects the expression vector can further include a reporter sequence under control of a separate promoter.

The present disclosure additionally provides methods of generating iPS cells. In one aspect such a method can include separately cloning a plurality of reprogramming factors including OCT3/4, SOX2, and at least one member selected from the group consisting of KLF4, c-Myc, NANOG, or LIN28 into separate vectors, where each reprogramming factor is controlled by a separate promoter. The method can further include consecutively cloning each of the reprogramming factors including each promoter into a single shuttle vector, linearizing the shuttle vector and recombining in bacterial cells to create an expression vector, infecting transformable cells with the expression vector, and growing the transformable cells for a period of time to generate iPS cells. In one specific aspect, the reprogramming factors can be cloned into separate vectors using blunt end ligation. In some aspects, the present method can further include generating the iPS cells in the absence of feeder cells, in the absence of a matrigel matrix, or in the absence of feeder cells and a matrigel matrix.

Furthermore, in one aspect an iPS cell is provided that is generated according to the methods and techniques of the present disclosure. In another aspect, a subsequent generation cell ultimately obtained from the iPS cell according to the present disclosure is provided. In yet another aspect, the differentiated cell derived from the iPS cell according to the present disclosure is provided. Non-limiting examples of such differentiated cell types can include endoderm, ectoderm, mesoderm, or an appropriate combination thereof. In some aspects, the differentiated cell can be a neuron.

BRIEF DESCRIPTION OF THE DRAWINGS

FIG. 18A shows the generation of iPS cells using the CMV weak promoter in accordance with another aspect of the present disclosure;

FIG. 18B shows the generation of iPS cells using the CMV weak promoter in accordance with another aspect of the present disclosure;

FIG. 18C shows the generation of iPS cells using the CMV weak promoter in accordance with another aspect of the present disclosure; and FIG. 19 shows a schematic view of an exemplary expression construct in accordance with another aspect of the present disclosure.

DETAILED DESCRIPTION

Figure 1:
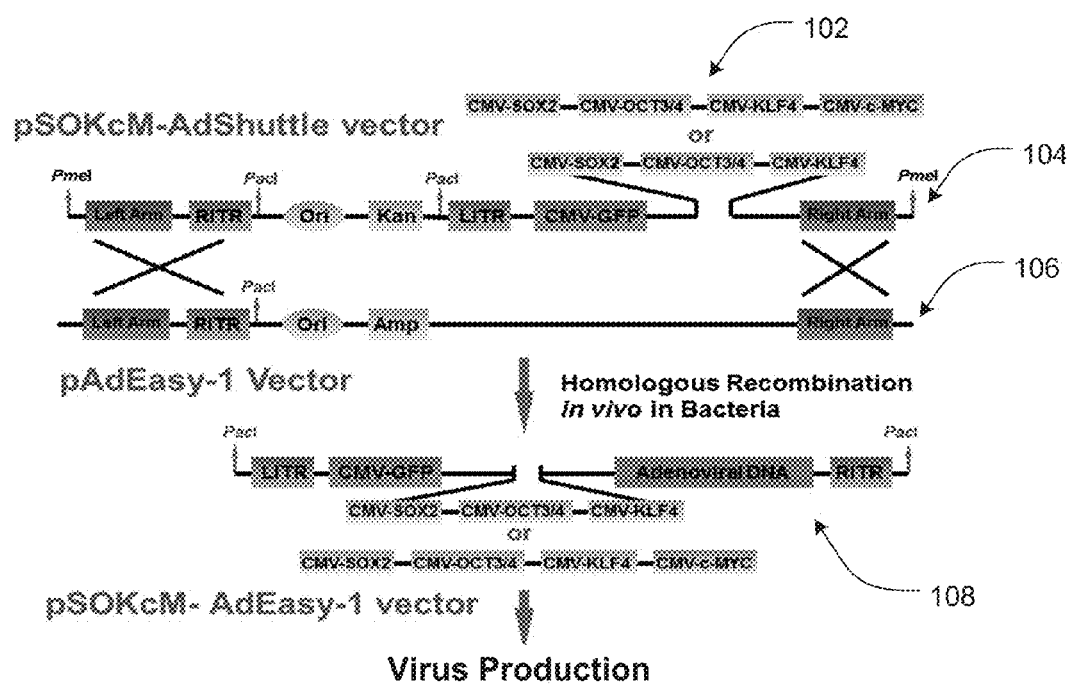
FIG. 1 is a schematic view of a vector system in accordance with one aspect of the present disclosure.

Before the present disclosure is described herein, it is to be understood that this disclosure is not limited to the particular structures, process steps, or materials disclosed herein, but is extended to equivalents thereof as would be recognized by those ordinarily skilled in the relevant arts. It should also be understood that terminology employed herein is used for the purpose of describing particular embodiments only and is not intended to be limiting.

Definitions

The following terminology will be used in accordance with the definitions set forth below.

It should be noted that, as used in this specification and the appended claims, the singular forms "a," and, "the" include plural referents unless the context clearly dictates otherwise. Thus, for example, reference to "a cell" includes one or more of such cells and reference to "the flask" includes reference to one or more of such flasks.

As used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result. For example, a composition that is "substantially free of" particles would either completely lack particles, or so nearly completely lack particles that the effect would be the same as if it completely lacked particles. In other words, a composition that is "substantially free of" an ingredient or element may still actually contain such item as long as there is no measurable effect thereof.

As used herein, the term "about" is used to provide flexibility to a numerical range endpoint by providing that a given value may be "a little above" or "a little below" the endpoint.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 2, 3, 4, and 5, individually.

This same principle applies to ranges reciting only one numerical value as a minimum or a maximum. Furthermore, such an interpretation should apply regardless of the breadth of the range or the characteristics being described.

The Disclosure

The inventors have developed a non-integrating vector system where multiple reprogramming factors are cloned in a single cassette in an expression vector. In some aspects, all defined reprogramming factors that are sufficient for the generation of iPS cells are cloned in a single cassette in an expression vector. Additionally, each gene corresponding to each reprogramming factor is expressed under the control of its own independent promoter that allows the balanced expression of all genes in one cell. In contrast to single expression of reprogramming factors in individual vectors, cells are reprogrammed into iPS cells in about 2-14 days with greater than about 80% efficiency without the need for feeder cells. These iPS cells show human ES cell morphology, and express ES cell surface markers and pluripotent cell-specific genes. The iPS cells can also be differentiated into cells of the three germ layers. Furthermore, iPS cells can be generated from a variety of cells, including, without limitation, human skeletal muscle cells and skin fibroblasts.

Several different standards to demonstrate pluripotency have traditionally been used. Except for the ability to generate normal embryos, iPS cells generated by the present invention in as little as 2-3 days without feeder cells meet all the reported criteria seen in iPS cells generated by other methods. Cells reprogrammed using the present techniques display features typical of human ES cells, including the presence of an unmethylated NANOG promoter, early initiation of mesenchymal to epithelial transition, expression of ES cell-marker genes and cell surface markers, as well as differentiation into germ layers in vitro and in vivo, including neurons.

Balanced expression of reprogramming factors under the control of individual promoters leads to a qualitative change in reprogramming and obviates the use of feeder cells. The short and reproducible time course of reprogramming can facilitate the study of these pathways and identify novel proteins important in the reprogramming process. This is particularly true for those proteins and lincRNAs that show overall little expression changes between the initial and final time points, but actually experience a change in between these time points. Initial pathway analysis highlights the importance of genes involved in cytokine-receptor pathways, with later upregulation of genes involved in hedgehog signaling, whereas genes involved in cell cycle and DNA replication are down-regulated at intermediate and late stages, as is described more fully herein. The more complete and coordinated activation of reprogramming pathways as a result of balanced expression of reprogramming factors can allow further detailed dissection of these pathways and their timing as well as analysis of the role of linc- and other non-coding RNAs in human reprogramming.

It should also be noted that the methods for vector construction, gene expression, generation of iPS cells, cell lines utilized, and other specific protocol details are shown as non-limiting examples in the following discussion. Furthermore, the techniques described herein can be utilized in a variety of contemplated transformation systems, and should not be seen as being limited to the iPS transformation system disclosed herein. Variation in the number of reprogramming factors included in the cassette and the specific types of reprogramming factors can vary, both within the iPS system and in other transformation systems.

A variety of promoters are contemplated, and any promoter that can be utilized as described herein is considered to be within the present scope. In some cases the selection of a given promoter or set of promoters can be a design choice that takes into account the particular expression vector utilized, any size requirements or limitations established by the promoter/vector combination, and the like. In one non-limiting aspect, however, the promoter can be a cytomegalovirus (CMV) promoter, and in some aspects a human CMV promoter. Additionally, in some aspects each reprogramming factor in the expression vector can have a separate promoter of the same promoter type, e.g. each reprogramming factor can have a separate CMV promoter. In other aspects, each reprogramming factor can have a separate promoter, but all of the promoters in the expression vector may not be of the same promoter type. Thus, in some cases different promoters can be utilized to affect the balance of expression of the reprogramming factors in a cell. In some aspects, each reprogramming factor may have a different type of promoter. It is also noted that a promoter can be modified to increase or decrease expression of a reprogramming factor if desired.

In some aspects it is contemplated that a promoter-driven reporter can be included in the cassette to, among other things, track transgene expression. Any reporter that can be loaded into the cassette with the reprogramming factors is considered to be within the present scope. In one specific example, the reporter can be a promoter driven GFP marker. Thus in some aspects a reporter can be expressed using a dedicated reporter promoter, while in other aspects a reporter can be expressed using one or more of the reprogramming factor promoters.

Furthermore, numerous expression vectors are contemplated, and any such vector that is capable of receiving and expressing multiple reprogramming factors each from dedicated promoters is considered to be within the present scope. Non-limiting examples can include adenoviral vectors, episomal vectors, retroviral vectors, lentiviral vectors, and the like.

As has been described, in one aspect the present disclosure provides a transformation construct for generating iPS cells that can include a vector backbone having a plurality of reprogramming factors, where each reprogramming factor is under control of a separate promoter. The vector backbone can be contained in a suitable delivery package such as, for example, an adenovirus particle, an episomal expression vehicle, etc.

As one specific example, and without using feeder cells and/or matrigel systems, the inventors have successfully created human induced pluripotent stem (iPS) cells from human embryonic fibroblast IMR90 cells by producing an adenoviral vector containing multi-reprogramming factors in a single cassette. It is noted that the use of IMR90 fibroblasts should not be seen as limiting, and any cell type capable of reprogramming is considered to be within the present scope. Non-limiting examples of cells and cell-types can include human fibroblasts, human fibroblasts from patients with SCA2, skeletal muscle (e.g. SKMC), and the like. Additionally, the present scope includes all fibroblast cell lines as well as other cells such as muscle and blood cells, as well as cell lines derived therefrom.

This adenoviral construct allows balanced expression of all reprogramming factors in single cell, and greatly speeds up the reprogramming efficiency of cells in a short period of time over conventional iPS cell generation methods. For example, traditional iPS cell generation methods can take about 30-45 days, whereas the present methods can generate iPS cells in 10 days or less. In one aspect, iPS cells can be generated in from about 2 to about 10 days. In another aspect, iPS cells can be generated in from about 2 to about 6 days. In yet another aspect, iPS cells can be generated in from about 2 to about 3 days. The time period for the generation of iPS cells is measured from the time of transfection with a viral cassette until the observable appearance of stem cell-like colonies.

As has been described, the current methods allow iPS cells to be generated without the use of feeder cells and/or matrigel systems. While not intending to be bound to any scientific theory, this may be due to a more rapid transformation of the cells into iPS cells. Because the multiple reprogramming factors are introduced simultaneously into recipient cells under the control of separate promoters, regardless of the expression vector utilized, this may allow a more rapid transformation into iPS cells that more quickly forms colonies of cells that have increased surface area compared to, for example, adhered fibroblasts. Such increased surface area also results in increased access to nutrients in the culture medium, thus rendering feeder cells unnecessary. Furthermore, the simultaneous or near simultaneous transformation into iPS cells may promote survival of iPS cells through secreted factors. Additionally, cells that are just about to transform into iPS cells, or that have just undergone this transition, begin to migrate towards each other to form colonies. This also suggests the presence of secretable factors to indicate location and initiate locomotion toward iPS cell colonies. Various classes of such secretable factors are contemplated, including, without limitation, peptides, proteins, lipoproteins, glycoproteins, glycolipids, and the like, and may be co-expressed with receptor molecules at the cell surface.

Numerous methods and techniques for generating an expression vector are contemplated, and can vary depending on the vector utilized, the cell system, the preferences of the technician, etc. As such, the following description is not considered to be limiting. In one aspect, reprogramming factors can be cloned separately into separate vectors, where each reprogramming factor is under the control of a separate promoter, such as, for example, a cytomegalovirus (CMV) promoter. One example of such a vector is pAdTrack-CMV. It is noted that the present scope includes any promoter that is capable of being separately associated with a set of reprogramming factors and loaded into a vector. Non-limiting examples can include the CAG-promoter, a combination of CMV early enhancer elements, chicken beta-actin promoter, and the like. Additionally, a mutated promoter, such as a mutated CMV promoter, can be utilized to alter the expression of the associated reprogramming factor.

Subsequently, multiple reprogramming factors along with the associated promoters can be consecutively subcloned into a shuttle vector. One non-limiting example can be using blunt end ligation. Any number of reprogramming factors can be subcloned into the shuttle vector. In one aspect, at least two reprogramming factors can be subcloned therein. In another aspect, at least three reprogramming factors can be subcloned therein. In another aspect, at least four reprogramming factors can be subcloned therein.

A variety of reprogramming factors and reprogramming factor combinations are contemplated, and any such factor or factor combination capable of generating iPS cells is considered to be within the present scope. Non-liming examples of reprogramming factors include OCT3/4, SOX2, KLF4, c-Myc, NANOG, LIN28, and the like, including combinations thereof. In one aspect, the reprogramming factors can include OCT3/4, SOX2 and at least one factor selected from KLF4, c-Myc, NANOG, or LIN28. In another aspect, the reprogramming factors can include OCT3/4, SOX2, and at least two factors selected from, KLF4, c-Myc, NANOG, or LIN28. In one specific aspect, the reprogramming factors include OCT3/4, SOX2, KLF4, and c-Myc. In one aspect, one example of an OCT3/4, SOX2, KLF4, and c-Myc construct is at least 80% homologous to SEQ ID 1. In another aspect, the construct can be at least 95% homologous, or 100% homologous to SEQ ID 1. Furthermore, in one aspect, the expression vector can have a sequence that is at least 80% homologous to SEQ ID 72. In yet another aspect, the expression vector has a sequence that is at least 95% homologous to SEQ ID 72. In a further aspect, the expression vector has the sequence of SEQ ID 72. In some aspects, SEQ ID 72 may be otherwise referred to as pAd-GFP-KcMOS. It should be noted that the order of the reprogramming factors as recited herein may not be limiting, but can be used in specific order when so specified. For example, pAd-GFP-KcMOS can be referred to in some aspects as pAd-SocMK. As such, the present scope includes sequences similar to SEQ ID 72 where the reprogramming factors have been inserted in a different order. A schematic representation of an exemplary expression construct pAd-GFP-KcMOS is shown in FIG. 19.

In another specific aspect, the reprogramming factors include or consist of OCT3/4, SOX2, and KLF4. In one aspect, one example of an OCT3/4, SOX2, and KLF4 construct is at least 80% homologous to SEQ ID 4. In another aspect, the construct can be at least 95% homologous, or 100% homologous to SEQ ID 4. In yet another specific aspect, the reprogramming factors include or consist of OCT3/4, SOX2, NANOG, and LIN28. In a further specific aspect, the reprogramming factors include OCT3/4, SOX2, NANOG, and LIN28. In yet another aspect, other members of the OCT, SOC, NANOG, and LIN families can be utilized.

In another aspect, at least one reprogramming factor can be selected from AIRE, CBFA2T3, CEBPE, CRABP2, EGR4, HIC2, IRX4, IRF7, KCNH2, KLF3, KLF4, KLF9, LIN28B, LHX6, LHX1, NFATC1, NFATC2, PEG3, POLR3G, PAX8, RAX2, RUNX3, SFRS17A, SOX8, TAF4B, ZNF57, and the like. In yet another aspect, at least one reprogramming factor can be selected from ETS1, FOXM1, HEY1, HOXA4, HOXA3, KLF6, KLF2, LZTS1, LBX2, MYBL1, MYBL2, MITF, POGK, RUNX1, SALL2, SOX6, SP140, SMAD6, SMAD9, TCF19, TOP2A, VGLL3, ZNF641, ZNF671, ZNF70, and the like.

Other non-limiting examples of reprogramming factors can include on or more selected from DBP, ZNF33B, CREB3L2, ZSCAN16, AHR, ZNF138, HSF4, HMX2, HEY1, ZNF192, PITX2, MAX, CIR1, PBX3, ZNF3, PRDM2, HOXC9, NFKB2, NRL, BATF3, SOX4, BARHL1, TSC22D3, MEF2D, GATAD2B, ZNF33A, KLF7, NR1D2, AHR, ZNF639, ETV6, IKZF4, NR1D2, ZNF217, HOXC8, GLIS3, HOXC6, ZNF397, ARID4A, ZNF496, MLLT10, ZFP36L1, NRL, PKNOX1, MTA3, PAX7, DMTF1, MZF1, RUNX1, HOXA2, HHEX, MLLT10, NFE2L1, PBX3, YEATS4, TAF6, SREBF2, RFX5, HCLS1, TP53, BACH1, TP53, ADNP, NFIL3, LMO4, KLF2, SCAND2, HOXA6, LMO4, SNAPC5, FOXC1, PCGF6, TAF5L, HOXB4, ETV6, HOXA4, ZNF256, ZNF449, ZNF193, RUNX1, ZBTB17, MYOG, NFIC, TBX5, HOXA5, CUX1, GLI3, CNOT7, TCF25, CNOT7, NPAT, SP4, MSC, IRF2, TBX5, RUNX1, ZBTB38, CREM, ZNF397, NR2F1, ZNF217, KLF5, RFXAP, HMGB2, CBL, ZNF93, ZSCAN12, MYST2, EGR2, SATB1, E2F1, PLAG1, PFDN1, E2F3, ZNF18, ENST00000300681, HLX, E2F2, SALL2, L3MBTL1, RCAN1, ARNT2, RERE, GTF2I, HIF1A, RUNX1, SMAD9, ZNF211, SMAD6, HOXB7, MLL, CREB3L4, GLI2, HOXB8, TBX3, IRF9, NR2F2, CREB3L4, NCOR1, SMAD9, ARNTL, CITED2, ZNF213, CITED2, LZTR1, RFX5, MEIS1, BCL6, TAF5L, RB1, ATF6B, CBFA2T2, ZNF219, SCAND1, ZFP36L1, MYPOP, PBX2, SHOX2, TBX3, STAT2, EBF1, LZTS1, EPAS1, TCF7L2, ZNF236, DLX1, PBX1, ZNF75D, ETS2, TCF25, CSRNP2, TADA2A, ZFHX2, JUN, MMP14, ZBTB16, TFDP3, ZNF19, ZSCAN21, MYC, SOX6, GATAD1, ZFHX3, RUNX2, CREBBP, ELK1, ZNF187, HIF1A, NOBOX, ZSCAN20, ELK1, JDP2, FOXD1, HCFC1, BRD8, TCF21, SIM2, ZKSCAN4, HOXA7, ZNF174, MLLT10, ADNP, TFDP1, CREB3L2, FLI1, SMAD3, ZBTB25, TSC22D2, TCF19, TFDP1, EBF1, STAT1, ETV3, RUNX1, ZNF117, TGIF1, RXRB, USF2, PKNOX2, TFE3, ETV5, SP1, ZKSCAN3, TEAD2, RUNX2, SMAD5, ZNF71, RBPJ, ZNF85, TCF7L1, AR, CREB3L1, PBX1, UHRF1, CREBL2, NR2E3, MSRB2, NFKB1, THRA, NFATC4, NME2, ETS1, TCEAL1, KLF12, USF2, ELF2, CLOCK, NR3C1, UHRF1, ZNF45, ZKSCAN4, ZNF135, HOXB2, ARNT, NFYC, UBP1, MEIS2, GLI2, TBX2, ZFHX4, CTBP1, ZKSCAN2, KLF6, STAT5B, ZFP37, LASS2, TEAD1, NR2C2, CUX1, THRA, RUNX1T1, SP140, HMG20A, STAT3, MYBL2, ZSCAN18, MTA2, TOP2B, SCMH1, HOXB2, ZNF3, ZNF281, ZXDC, ARNTL2, EBF1, STAT6, FOXO3, NR3C1, ZNF500, VAX2, MSRB2, PPARG, TCF4, CTBP1, HOXB3, DMTF1, SOX13, TADA3, HDAC1, ZKSCAN5, HOXB5, TARDBP, ZNF91, FOXC2, ZNF498, PTTG1, SUPT6H, GLI2, YY1, TAF12, FUBP1, STAT3, CREB1, ZEB2, ZNF175, PURA, CREM, ZNF268, ZNF132, SLC2A4RG, POU6F1, SMAD2, ZNF70, FOXO3, ATF1, RELA, TOP2A, TCF12, SP140, FUBP1, ZEB2, MSL3, BLZF1, MECOM, NFIC, PRRX1, KLF6, FOXM1, RELA, EGR1, CLOCK, ZNF202, TSHZ3, BACH1, PPARG, ZNF189, ZNF45, PHTF1, GTF2H4, PHTF1, SRF, FOXL1, ATF2, HOPX, NR2C1, ZNF69, SIX4, ELK3, ZNF167, MECOM, HMGB1, NFYB, ZNF148, ZEB1, RFXANK, PCGF2, STRN3, HOMEZ, ZNF498, NFAT5, SATB2, CTNNB1, ADNP2, TCF7L2, HOXB6, HIC1, ATF2, ZHX3, MTA1, GTF2IRD1, CTNNB1, E2F7, TRERF1, FOXF2, TFCP2, HDX, PITX1, ZNF207, E2F7, PRDM2, LCOR, PITX1, ZNF155, CUX1, FOXO3, MEF2C, TFE3, ZEB1, ZNF197, and the like.

Furthermore, additional non-limiting examples of reprogramming factors can include on or more selected from SLC30A9, ZFP36L2, ELK4, ZHX3, TCFL5, GABPB1, NKX3-1, BLZF1, BLZF1, ZSCAN2, ZNF134, AFF1, NFYA, NCOR1, TRPS1, PLAGL2, PURB, GTF2H3, TAF7, CBFB, TRPS1, ATF6, ZSCAN30, FOXN2, CTCF, CREB3, SOX9, SIX1, E2F3, BHLHE41, FOSL1, TEAD3, ZHX3, TWIST1, BUD31, AFF1, NPAS1, TFCP2, TAF1B, TFEB, AFF4, ZNF174, ETV1, ZSCAN30, ZNF35, SOX5, ETV1, NFYC, ETV1, TRIM22, NFE2L3, TSHZ1, ZNF83, ENO1, AFF4, FOXN2, TCF7L2, SMAD4, BNC1, ETV1, FOS, GAS7, TRIM28, NCOR1, ZSCAN22, ELK4, SALL1, GATAD2A, DRAP1, TFAM, MEIS3, NFIX, MSX2, SMAD1, EGR3, POU2F2, GABPB1, ELF1, NFYC, IRF3, ZNF215, MAFK, ENST00000445531, KLF10, BHLHE40, TFAM, TSC22D1, MEF2B, CSRNP1, HR, CSRNP1, JUND, TARDBP, RARG, ATF5, TCF3, BCL3, PRDM1, ELF1, JUNB, GCFC1, MAFF, TULP4, USF1, IRF1, RBCK1, NOTCH1, AHCTF1, ZNF134, PPARD, ZNF274, TGIF2, UBN1, PRDM1, KLF3, MEF2B, ZNF444, DRGX, RAX2, MNT, PPARA, ZNF41, ZNF215, HMGA1, ZNF169, RBCK1, ZNF169, MBD1, MYCL1, TARDBP, C2orf3, ZNF81, FOXO4, MAX, MYNN, PLAGL2, FOSB, MSX1, KLF16, ZNF197, SOLH, ELF4, ZHX1, NFIA, IRF3, GCFC1, TEAD4, ZHX2, TFEB, E2F5, NKX1-1, AATF, GATA2, HNRNPAB, NFATC2, ZNF92, MAX, ZNF628, KLF4, RXRA, ZNF232, CSDA, PA2G4, YBX1, XBP1, MLL, NPAS2, SCML2, CSDA, SOX13, MYOD1, PPARD, NOTCH1, CNBP, TFIP11, IRF7, ZSCAN29, NKX2-3, ZNF24, HNF1B, C11orf9, FBXW7, MEF2D, REXO4, NFATC3, SOX8, ZNF207, SPEN, MGA, SNAPC4, ZRANB2, PA2G4, AHCTF1, MNT, ARID3A, RNF4, ERF, ETV4, DLX2, KLF9, ESRRA, YBX1, GATAD2A, ESRRA, TP73, KLF17, NKX6-3, MXD1, NFYC, HOXA9, TBP, TP73, HSF1, MBD1, TSC22D4, CEBPB, MTF1, RARA, BTAF1, MBD1, TLX2, TAF13, MRRF, CITED1, NFATC1, MLL, FOXL2, LASS5, NR1H3, NFATC1, LEF1, ZNF81, POU3F1, MXD1, PAX8, NOLC1, MGA, TBX1, SCML1, GABPA, NR1D1, MEF2A, POU2F1, HMBOX1, MAFG, HMX1, ZGPAT, IRX4, MBD1, MAFG, GRHL2, SPDEF, ATF3, PRRX2, NR1H2, E2F6, MAFB, MRRF, KLF11, HR, HEYL, CNBP, SNAPC2, MLX, FOXA3, ATF3, PITX3, ZNF24, ZSCAN5A, AEBP1, E2F6, ZNF37A, LHX1, E2F6, HMBOX1, ETV2, FOXK2, ATF3, MAFB, RUNX3, ZGLP1, FOXK2, ZNF394, SPIB, ETV2, ZNF394, VDR, HMBOX1, HMG20B, LASS6, MYNN, ZGLP1, FOXK2, NR6A1, ARGFX, HIRA, CDX1, KLF1, ESR1, EN2, ZKSCAN1, HMG20B, TCF15, TPRX1, HMG20B, RARA, NFYA, ZNF263, RORA, PURB, TAF5, GSX1, HNF1A, UNCX, SEBOX, LASS6, FOXE3, IRX2, BATF2, DUXA, MAF, E2F4, MLL, ZNF148, MAFA, ZNF165, SIX2, LHX6, ECSIT, DUX4, HES6, TAF4, TFAP2E, SIX3, NR4A2, RELB, IRX2, LHX3, NFE2, NR4A2, MLL4, HOXA10, SPEN, E4F1, NKX1-2, SREBF1, NKX2-5, HES6, ZNF169, CCRN4L, RFX3, TBX19, RBCK1, FOXH1, HOXB9, HES6, MESP1, LBX1, STAT4, DUX4, NFX1, NR2F6, HES6, HES1, HMX1, PPARA, ZNF445, DUX4L4, SOX11, EVX1, PBX4, ZXDC, ZNF131, LMO1, ZNF3, KDM5B, STAT5A, DUX4, PHF5A, REL, ZNF446, MLL4, ZNF157, IRF5, HOXA9, TAF10, HSF1, ZNF133, TRERF1, NR113, ISL2, LMX1B, SIM1, SCAND2, MYNN, ARX, TBX6, VSX1, TBX10, NR5A2, GATA6, PAX6, TFDP2, KDM5B, SNAPC5, HAND1, PAX4, DUX4, NFX1, ZNF277, SNAPC5, ZBTB48, POU5F1, ESRRG, HOXD9, CBFA2T2, FOXD2, TEF, PHF1, DDIT3, SUPT4H1, LASS3, ZNF33A, RORB, POU5F1, DMRT1, HINFP, EDF1, CDX1, ATF4, ZNF323, CNOT8, POU4F2, VPS72, FOSL2, ATF3, NFXL1, ZIC1, SPI1, CREB5, CEBPD, C5orf41, HSF1, DUX4, ZNF33A, NEUROG3, TRIM25, SREBF1, GCM1, EMX1, LASS4, PRDM2, HMX3, ONECUT2, SIX5, HOPX, ESRRB, HSF2, HOXC4, PROP1, ZNF33A, ZSCAN2, SHOX, HOXA3, NR4A3, MESP2, and the like.

Additionally, it should be noted that any one or more of the above reprogramming factors can be utilized with any other reprogramming factor described herein or in any combination with any other reprogramming factor described herein.

Turning now to FIG. 1, a schematic outline of one non-limiting example of an expression system (e.g. AdEasy-1) is provided. Reprogramming factors of interest, such as, and without limitation, OCT3/4, SOX2, KLF4, and c-Myc, can be first cloned separately into a vector under separate promoters 102 (e.g. pAdTrack-CMV). Then, each reprogramming factor along with the promoter can be consecutively subcloned into a shuttle vector 104 (e.g. pAdTrack) using a technique such as, for example, blunt end ligation. The resultant plasmid can be linearized by digesting with a restriction endonuclease such as PmeI, and recombination can be carried out using high competence bacterial cells, such as E. coli BJ5183 cells, by homologous recombination. In some cases, high competence bacterial cells can allow for more efficient recombination. In cases where an adenoviral vector is to be used, the recombinant adenoviral plasmid 106 (e.g. pSOKcM-AdEasy-1) can then be linearized 108 with an enzyme such as PacI and transfected into an adenovirus packaging cell line for virus production. One non-limiting example of such a cell line is HEK 293A. The "left arm" and "right arm" shown in FIG. 1 represent the regions mediating homologous recombination between the shuttle vector 104 and the adenoviral backbone vector 106. The recombination can be confirmed by multiple restriction endonuclease analyses, and the production of recombinant adenoviruses can be followed by GFP expression.

Figure 2A:
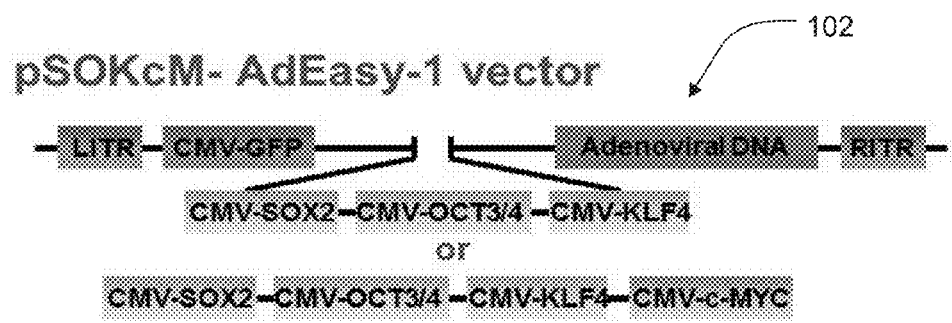
FIG. 2A is a schematic view of a vector system in accordance with another aspect of the present disclosure.
Figure 2B:
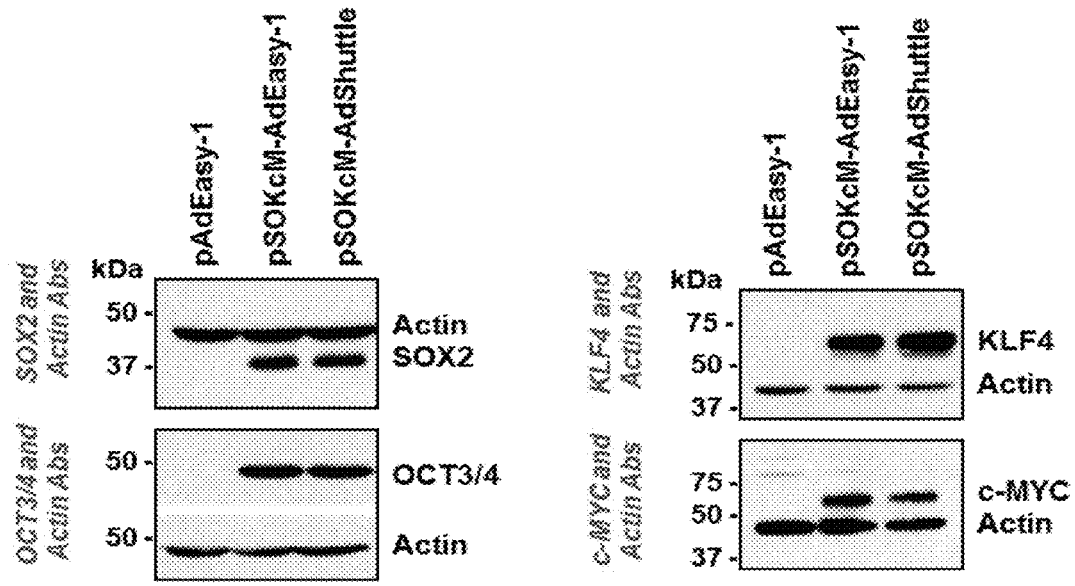
FIG. 2B shows data demonstrating protein expression of multiple reprogramming factors in accordance with another aspect of the present disclosure.
Figure 3A:
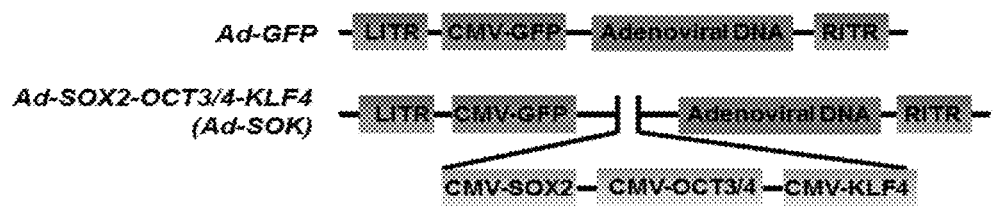
FIG. 3A is a schematic view of an adenoviral construct in accordance with yet another aspect of the present disclosure.
Figure 3B:
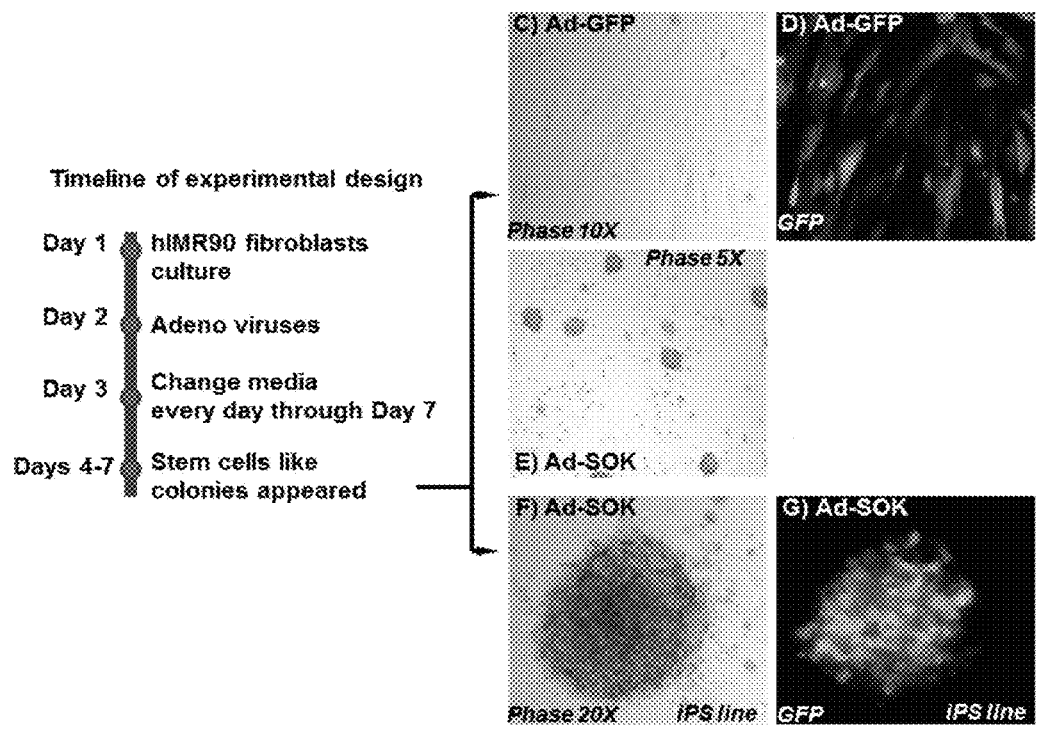
FIG. 3B shows iPS cells generated with adenoviral constructs without feeder cells, IMR90 cells transduced with Ad-GFP, and iPS cell colonies in IMR90 cells transduced with Ad-SOK in accordance with another aspect of the present disclosure.

Validation of protein expression can be accomplished using any of a number of known methods, such as western blotting, and the like. As one example, FIG. 2A shows a schematic representation of an adenoviral vector containing multi-reprogramming factors in a single cassette, pSOKcM-AdEAsy-1 102. FIG. 2B shows SH5Y cells that were transiently transfected with pSOKcM-AdEasy-1 and pSOKcM-AdShuttle constructs. Protein extracts from harvested cells at 40-54 hrs post-transfection were probed by Western blot analysis using the antibodies indicated. Blots were re-probed for Actin as an internal loading control. These results indicate that the recombinant adenoviral construct expresses all proteins from the adenoviral vector in cells tested.

iPS cells can thus be generated using an expression vector containing multi-reprogramming factors. iPS cells can be generated from a variety of transfectable cell types, and any type of cell capable of transfection is considered to be within the present scope. One specific example of such a transfectable cell type includes IMR90 human fetal fibroblasts. As is shown in FIG. 3, iPS cells can be generated with an adenoviral vector without feeder cells or a matrigel matrix. In FIG. 3A, adenoviral constructs (AdEasy-1): Ad-GFP or Ad-SOK are shown. In FIG. 3B a timeline of experimental design is shown. IMR90 cells were transduced with adenoviruses, Ad-GFP or Ad-SOK on day 2. Culture medium was changed every day with regular cell culture medium. Colonies appeared at days 4-7 in culture dishes. The top of FIG. 3B shows photomicrographs of IMR90 cells transduced with Ad-GFP on day 7; phase contrast in the top left image and GFP expression in the top right image. FIG. 3B middle and bottom images show iPS cell-like colonies appearing in IMR90 cells transduced with Ad-SOK on days 4-7, as shown by phase contrast (FIG. 3B middle and bottom left). GFP expression in fluorescence microscopy of the same colony is shown in FIG. 3B bottom right. Thus by days 4-7, several colonies showing ES cell-like morphology emerged and all colonies looked identical. The resultant colonies (iPS cells) can be further expanded or subjected to characterization.

Figure 4A:
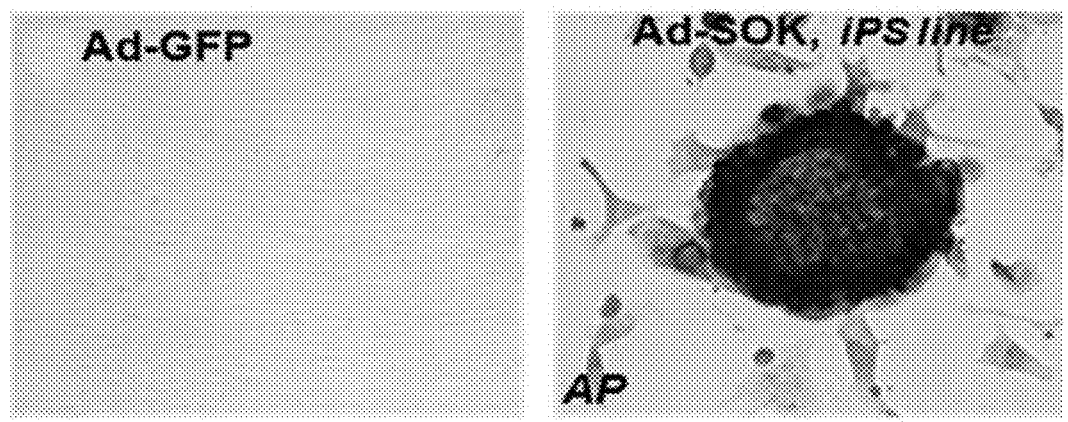
FIG. 4A shows IMR90 cells transduced with adenoviruses, either Ad-GFP (a) or Ad-SOK (b) in accordance with a further aspect of the present disclosure.
Figure 4B:
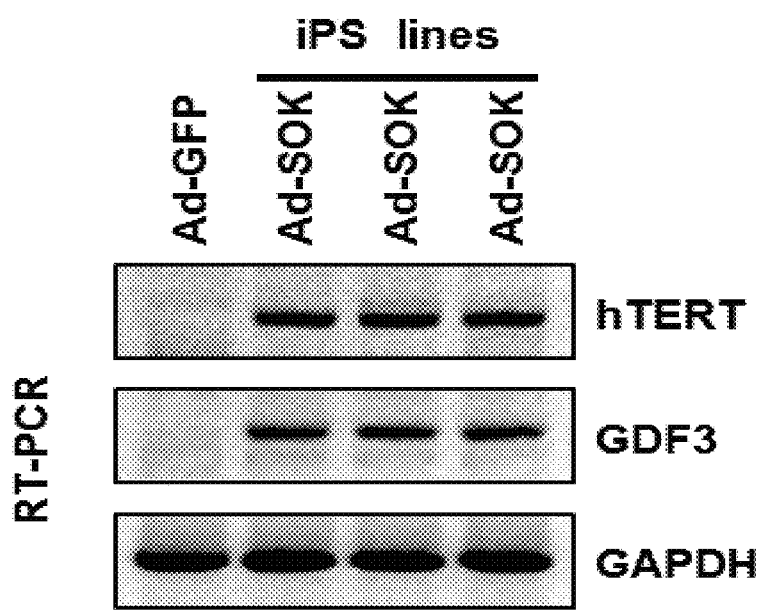
FIG. 4B shows RT-PCR data of EX cell marker genes in accordance with yet a further aspect of the present disclosure.

Following generation, iPS cells can be further characterized. The undifferentiated state of human ES cells/iPS cells express high levels of membrane alkaline phosphatase (AP), and AP staining can be used to characterize such stem cells. For AP staining, iPS cells are generated from iMR90 cells in 24 well plates using the methods as described. At day 7, iPS cells are fixed with 4% paraformaldehyde for 2 minutes, followed by 15-minute incubation with staining solution (Alkaline Phosphatase Detection Kit; Millipore). AP staining data demonstrate the positive staining for iPS cells, as shown in FIG. 4A. In this case, IMR90 cells are transduced with adenoviruses, Ad-GFP or Ad-SOK for 7 days. Human iPS cells generated from Ad-SOK are positive for alkaline phosphatase (AP) staining. FIG. 4B shows RT-PCR analyses of ES cell marker genes. IMR90 cells are transduced with adenoviruses, Ad-GFP or Ad-SOK for 7 days. Total RNA is isolated from harvested cells and synthesized cDNAs (150 ng) are used for RT-PCR analyses. Human iPS cells express many undifferentiated ES cell marker genes including telomerase reverse transcriptase (hTERT) and growth and differentiation factor 3 (GDF3). FIG. 4B shows an expression profile by RT-PCR analyses, demonstrating that iPS cells derived from IMR90 cells highly express the hTERT and GDF3 genes.

Figure 5A:
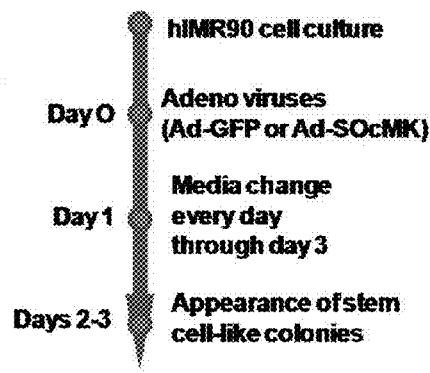
FIG. 5A shows a timeline for transformation in accordance with another aspect of the present disclosure.
Figure 5B:
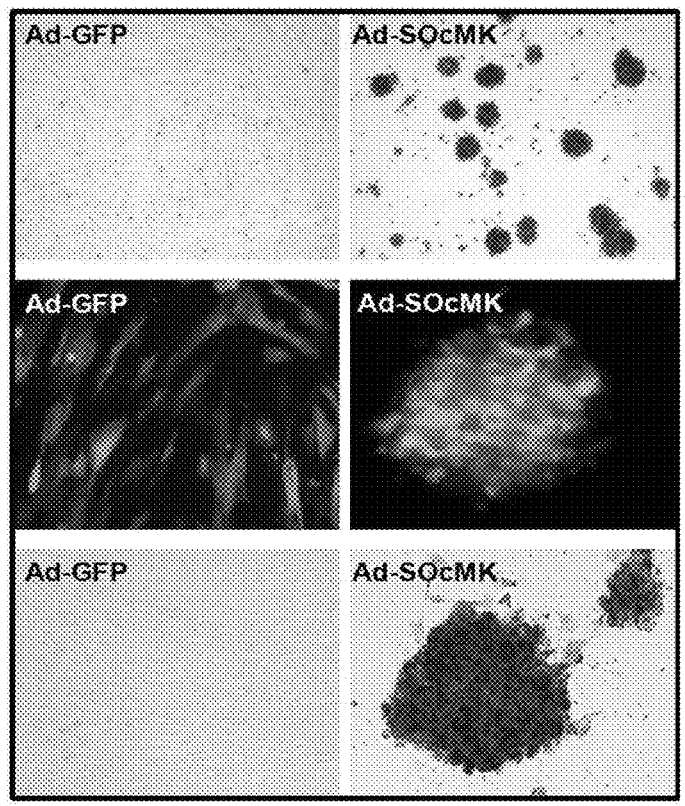
FIG. 5B shows cells tested for ALP staining in accordance with another aspect of the present disclosure.
Figure 5C:
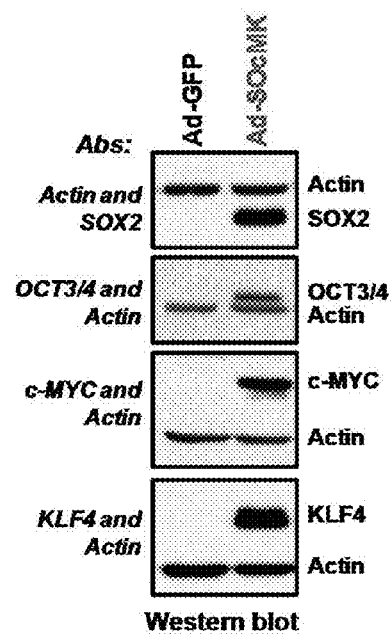
FIG. 5C shows a Western blot analyses in accordance with another aspect of the present disclosure.

In another aspect of the present disclosure, somatic cell reprogramming was tested using the adenovirus containing OCT3/4, SOX2, KLF4, and c-Myc (Ad-SOcMK) shown in FIG. 1. IMR90 cells were transduced with the adenovirus, and the timeline for transformation is shown in FIG. 5A. Briefly, the IMR90 cells were transduced with Ad-SOcMK or Ad-GFP for 12 or 24 hrs, after which the medium was replaced with human ES cell medium. Within 1 day, Ad-SOcMK-transduced cells took on a different appearance and began to form small cell clusters. By day 2 or 3, several colonies of cells showing ES cell-like morphology emerged in the dish (FIG. 1B, top right and middle right). Cells were also tested for ALP staining, as is shown in FIG. 5B, bottom right. The ALP assay reveals strong staining of IMR90-derived iPS cells indicating pluripotency, while no ALP staining is observed in the GFP-transduced cells (FIG. 5B, lower left). The expression of exogenous individual protein factors in protein extracts from harvested cells was also investigated by Western blot analyses, as is shown in FIG. 5C. The results demonstrate that all RFs in the adenovirus are highly expressed in transduced IMR90 cells but not in Ad-GFP-transduced cells.

Gene expression changes during the reprogramming process have traditionally been difficult to study. One reason for this difficulty in human cells may be due to the fact that currently known methods of reprogramming occur at low frequency and take such long periods of time to occur. This is particularly true for a new class of regulatory RNAs, called long inter-spersed non-coding (linc) RNAs. The short and synchronized reprogramming process of the present disclosure can facilitate the study of global transcription changes. To pursue these issues, the inventors have studied global gene expression changes during reprogramming to determine the correlation between gene expression changes and reprogramming. Using singular value decomposition, for example, regulated functional pathways in early and intermediate stages of reprogramming of human cells have been identified, including a set of novel lincRNAs.

Figure 6A:
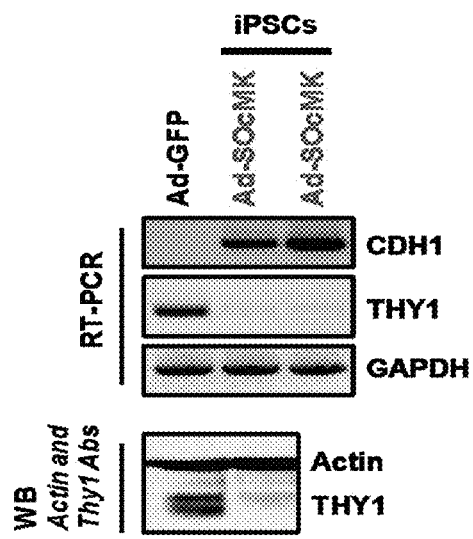
FIG. 6A shows real-time PCR and Western blot data in accordance with another aspect of the present disclosure.
Figure 6B:
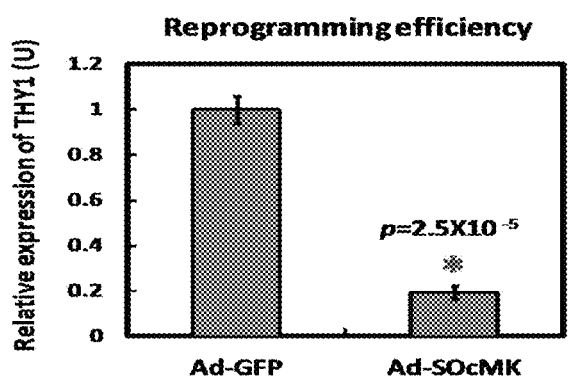
FIG. 6B shows real-time PCR and Western blot data in accordance with another aspect of the present disclosure.

Without intending to be bound to any scientific theory, mesenchymal-to-epithelial transition (MET) is a key regulatory event during reprogramming of somatic cells to the pluripotent state. Expression of exogenous reprogramming factors effectively activate the epithelial program and shut down key mesenchymal genes to favor the MET transition of somatic cells toward induced pluripotency. These events are associated with depletion of the mesenchymal marker THY1, and upregulation of the epithelial marker CDH122-24. To investigate this, the steady-state levels of THY1 and CDH1 in iPS cells generated with Ad-SOcMK are measured. RT PCR and Western blot analyses reveals upregulation of CDH1 and concomitant reduction of THY1 in iPSCs when compared with control (See FIG. 6A). As THY1 is exclusively expressed in fibroblasts and fibroblast cells dramatically switched the state in a short period of time, the expression level of THY1 by real-time PCR can be determined as a function of reprogramming efficiency. Real-time PCR and Western blot data reveals a decrease in levels of THY1 by ~80% in Ad-SOcMK transduced cells as cells are reprogrammed (See FIG. 6A lower panel, and FIG. 6B).

Figure 7A:
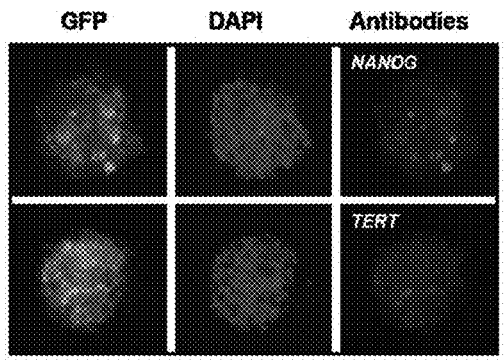
FIG. 7A shows data demonstrating expression of markers in iPS cells in accordance with another aspect of the present disclosure.
Figure 7B:
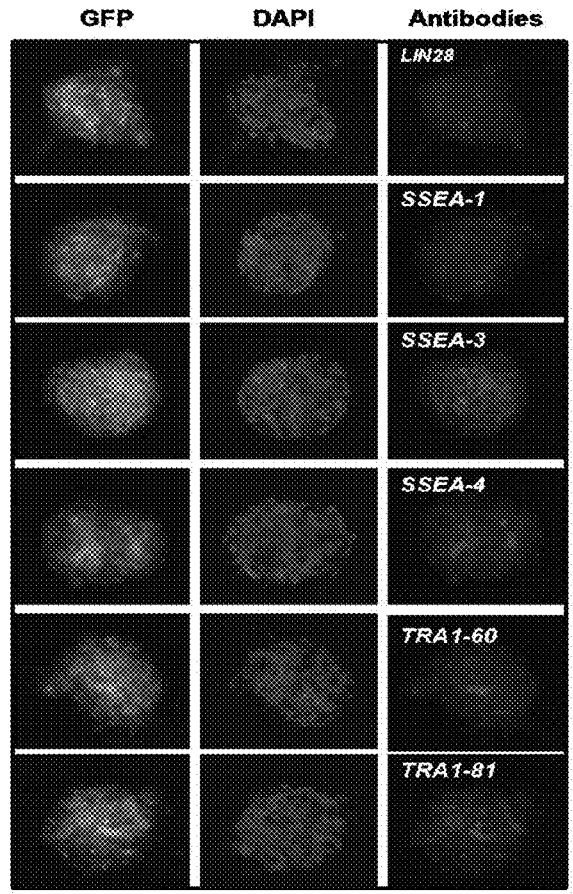
FIG. 7B shows data demonstrating expression of markers in iPS cells in accordance with another aspect of the present disclosure.

It was next examined whether iPS cells generated with Ad-SOcMK express human ES cell-marker genes such as NANOG, Telomerase reverse transcriptase (TERT), LIN28, stage specific embryonic antigens (SSEA-1, -3, and -4), and tumor-related antigens (TRA1-60 and -81). Expression of each marker in iPS cells was studied by immunofluorescence using antibodies against endogenous proteins (FIGS. 7A-B). The corresponding secondary antibodies were conjugated with Dylight variants. Immunostaining data revealed expression of ES cell markers in iPS cells generated with Ad-SOcMK from IMR90 cells.

Figure 8A:
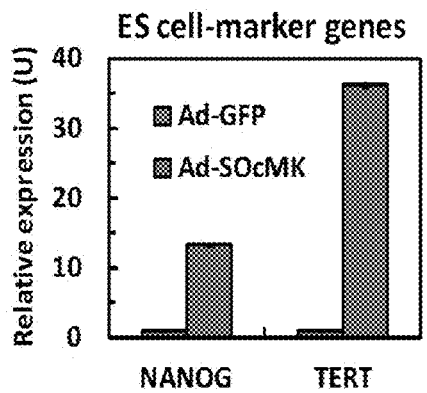
FIG. 8A shows data representing isolated RNA from iPS cells that demonstrate high expression of undifferentiated ES cell-marker genes in accordance with another aspect of the present disclosure.
Figure 8B:
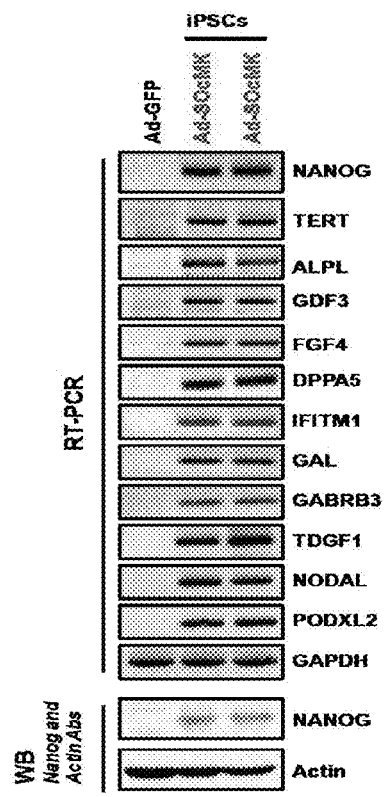
FIG. 8B shows data representing isolated RNA from iPS cells that demonstrate high expression of undifferentiated ES cell-marker genes in accordance with another aspect of the present disclosure.
Figure 8C:
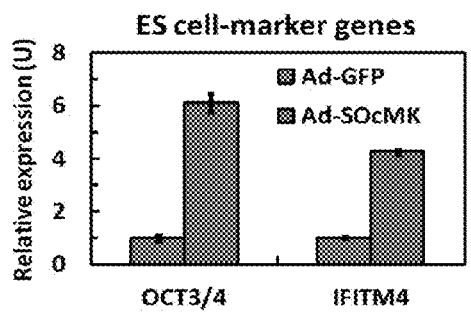
FIG. 8C shows data representing isolated RNA from iPS cells that demonstrate high expression of undifferentiated ES cell-marker genes in accordance with another aspect of the present disclosure.
Figure 8D:
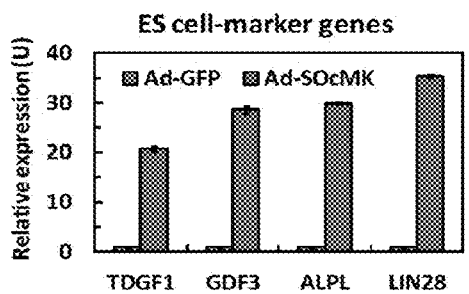
FIG. 8D shows data representing isolated RNA from iPS cells that demonstrate high expression of undifferentiated ES cell-marker genes in accordance with another aspect of the present disclosure.
Figure 8E:
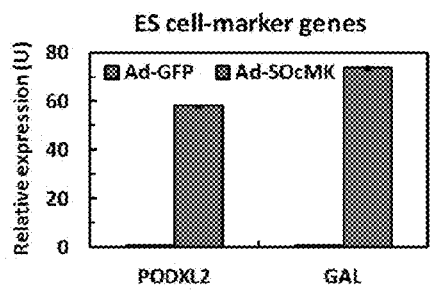
FIG. 8E shows data representing isolated RNA from iPS cells that demonstrate high expression of undifferentiated ES cell-marker genes in accordance with another aspect of the present disclosure.
Figure 8F:
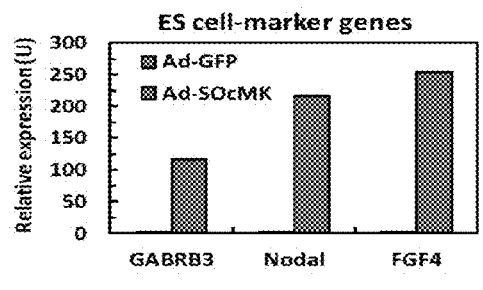
FIG. 8F shows data representing isolated RNA from iPS cells that demonstrate high expression of undifferentiated ES cell-marker genes in accordance with another aspect of the present disclosure.

To measure steady state levels of undifferentiated ES cell-marker genes, real-time RT-PCR, semi-quantitative PCR, and Western blot analyses can be performed. Real-time and semi-quantitative PCR analysis of isolated RNA from iPS cells demonstrate high expression of undifferentiated ES cell-marker genes, including NANOG, TERT, LIN28, ALPL, growth and differentiation factor 3 (GDF3), fibroblast growth factor 4 (FGF4), developmental pluripotency-associated 5 (DPPA5), interferon induced transmembrane protein 1 (IFITM1), galanin prepropeptide (GAL), gamma-aminobutyric acid (GABA) A receptor, beta 3 (GABRB3), teratocarcinoma-derived growth factor 1 (TDGF1), Nodal homolog (NODAL) and podocalyxin-like 2 (PODXL2) (See FIGS. 8A-F). Western blot analyses in protein extracts from harvested iPS cells confirmed protein expression of NANOG in iPS cells generated with Ad-SOcMK (FIG. 8B, bottom panel).

Figure 9:
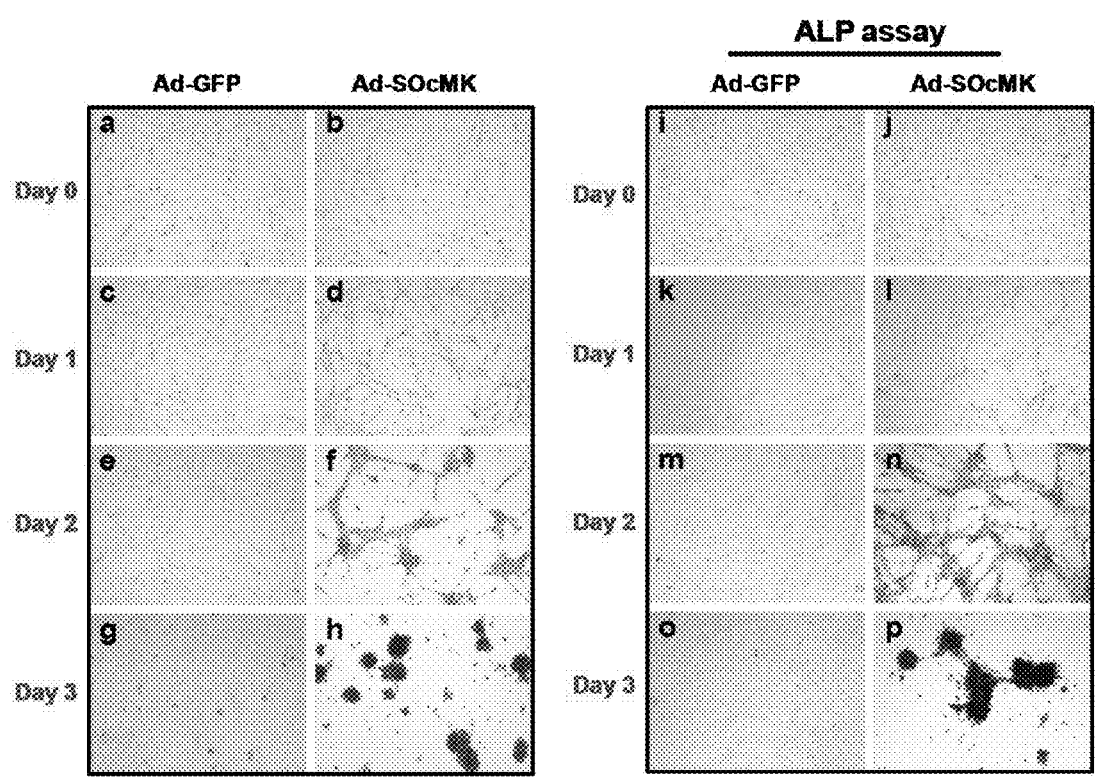
FIG. 9 shows images of cells undergoing morphological changes in accordance with another aspect of the present disclosure.

One of the prominent morphological changes during MET is the transformation of elongated fibroblasts into tightly packed clusters of rounded cells. Ad-SOcMK transduced cells undergo progressive epithelial-like morphological changes from elongated fibroblasts (FIG. 9, panels a, b) to packed clusters of rounded cells as visualized by phase contrast microscopy (FIG. 9, panels d, f, h). Morphological changes occur in close association with expression of ALP. ALP-positive cells appeared as early as day 1 in Ad-SOcMK transduced cells and ALP positive cells progressively increased as reprogramming time increased (FIG. 9, panels l, n, p). Cells transduced with Ad-GFP showed neither morphological changes (FIG. 9, panels c, e, g) nor staining for ALP (FIG. 9, panels k, m, o). Thus, reprogramming of IMR90 cells by Ad-SOcMK results in rapid and specific mesenchymal to epithelial transition with very high efficiency.

Such reprogramming of somatic cells is also accompanied by significant epigenetic changes. As one example, the NANOG promoter changes from a highly methylated state in somatic cells to being unmethylated and active in iPS cells. In one aspect, bisulfite genomic sequence analysis can be used to evaluate the methylation status of cytosine guanine dinucleotides (CpGs) in the NANOG promoter. CpGs are highly unmethylated in iPS cells when compared with the highly methylated CpGs in parent IMR90 cells. This indicates that the NANOG promoter is active in iPS cells derived from IMR90 cells resulting in increased steady-state levels (FIG. 8B, lower panel). In order to exclude the possibility of viral DNA integration into genomic DNA, Southern blot analysis can be performed by digesting genomic DNA from iPS cells generated with Ad-SOcMK with BamHI and AscI for KLF4 and c-MYC probes, respectively. Notably, Southern blot analyses does not detect genomic integration of the adenoviral transgene into iPS cells derived from IMR90 cells (data not shown). In addition, chromosomal G-band analyses showed that iPS cells generated with Ad-SOcMK had a normal karyotype of 46XX (data not show n).

Figures 10A, 10B, 10C, 10D, 10E:
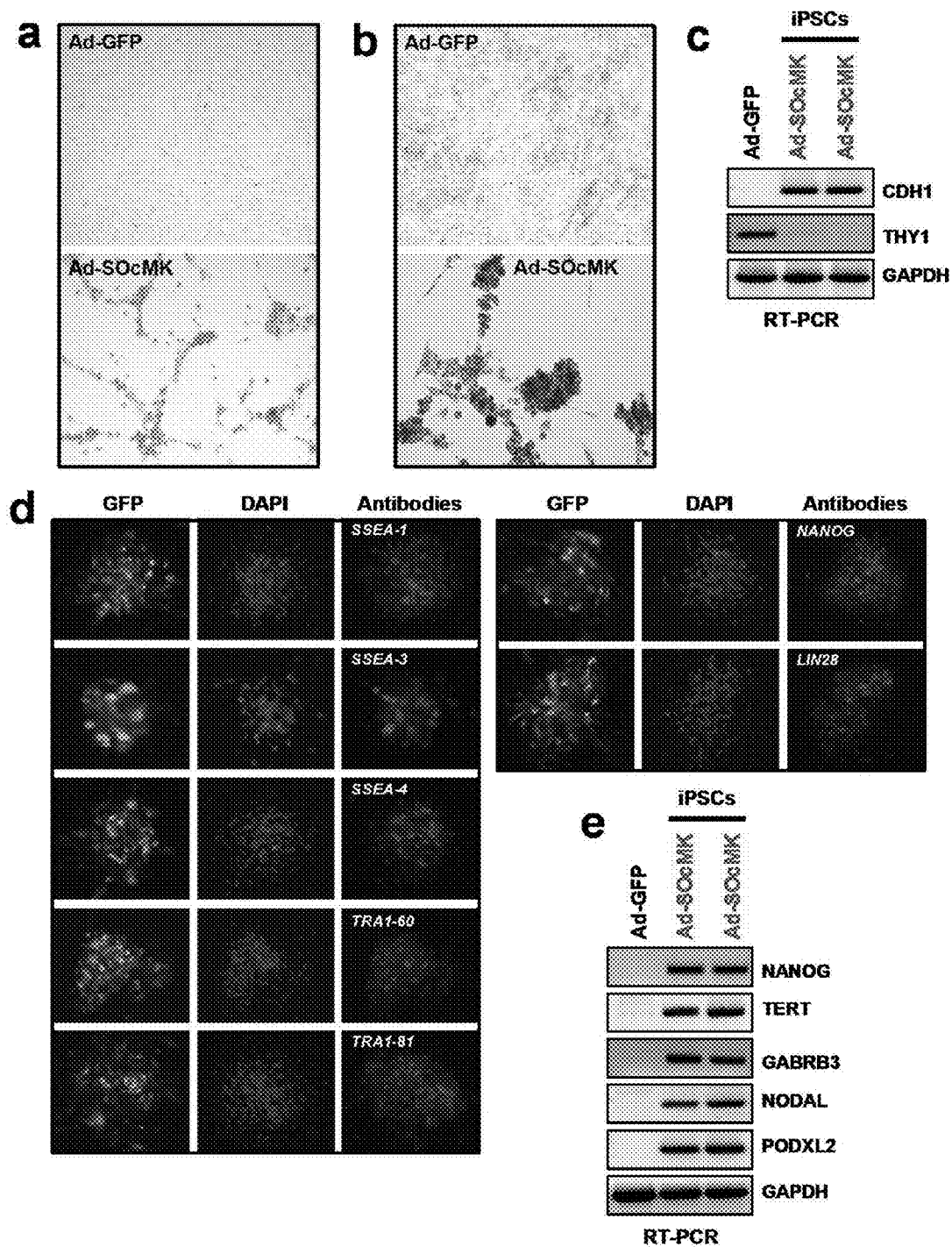
FIG. 10A shows data from SkMC-derived iPS cells in accordance with another aspect of the present disclosure.
FIG. 10B shows data from SkMC-derived iPS cells in accordance with another aspect of the present disclosure.
FIG. 10C shows data from SkMC-derived iPS cells in accordance with another aspect of the present disclosure.
FIG. 10D shows data from SkMC-derived iPS cells in accordance with another aspect of the present disclosure.
FIG. 10E shows data from SkMC-derived iPS cells in accordance with another aspect of the present disclosure.
Figures 11A, 11B, 11C, 11D, 11E:
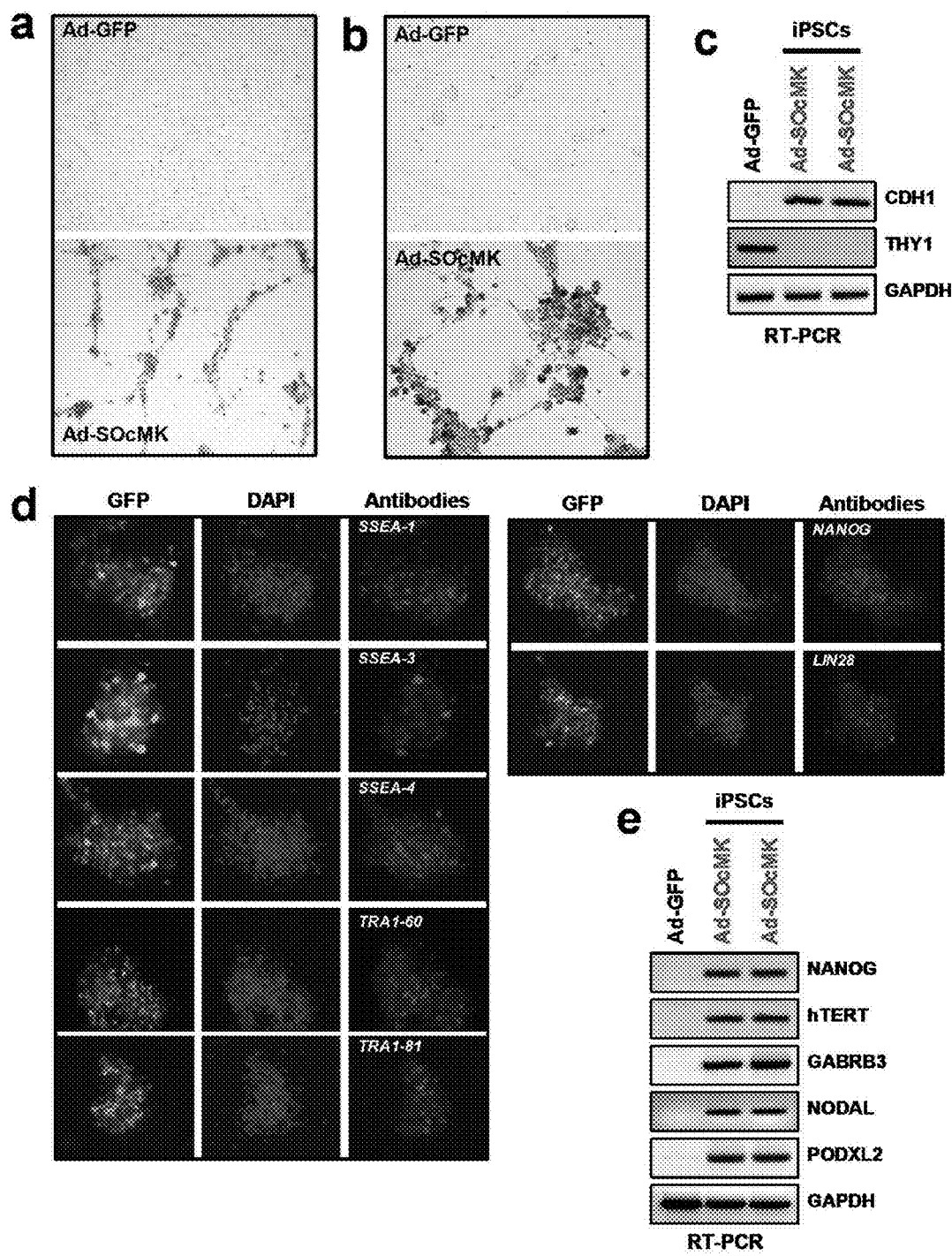
FIG. 11A shows data from SCA2 skin fibroblast-derived iPS cells in accordance with another aspect of the present disclosure.
FIG. 11B shows data from SCA2 skin fibroblast-derived iPS cells in accordance with another aspect of the present disclosure.
FIG. 11C shows data from SCA2 skin fibroblast-derived iPS cells in accordance with another aspect of the present disclosure.
FIG. 11D shows data from SCA2 skin fibroblast-derived iPS cells in accordance with another aspect of the present disclosure.
FIG. 11E shows data from SCA2 skin fibroblast-derived iPS cells in accordance with another aspect of the present disclosure.

As has been described, a variety of cell types can be utilized to generate iPS cells according to aspects of the present disclosure, and any such capable cell is considered to be within the present scope. As examples, human skeletal muscle cells (SkMCs) and spinocerebellar ataxia 2 (SCA2) patient skin fibroblasts can be used. When SkMCs and SCA2 skin fibroblasts are transduced, several iPS cell colonies resembling ES cell-like morphology emerge in the dishes as early as day 3. The SkMC and SCA2 skin fibroblast-derived iPS cells positively stain for ALP, and immunofluorescence and RT-PCR analysis data reveals that these iPS cells express many undifferentiated ES cell-marker genes and followed the MET process (For SkMCs see FIG. 10, panels a-e; for SCA2 see FIG. 11, panels a-e). These findings demonstrate that the expression vectors of the present disclosure can be used to generate iPS cells rapidly and efficiently from a number of somatic cells in a short period of time.

Figure 12:
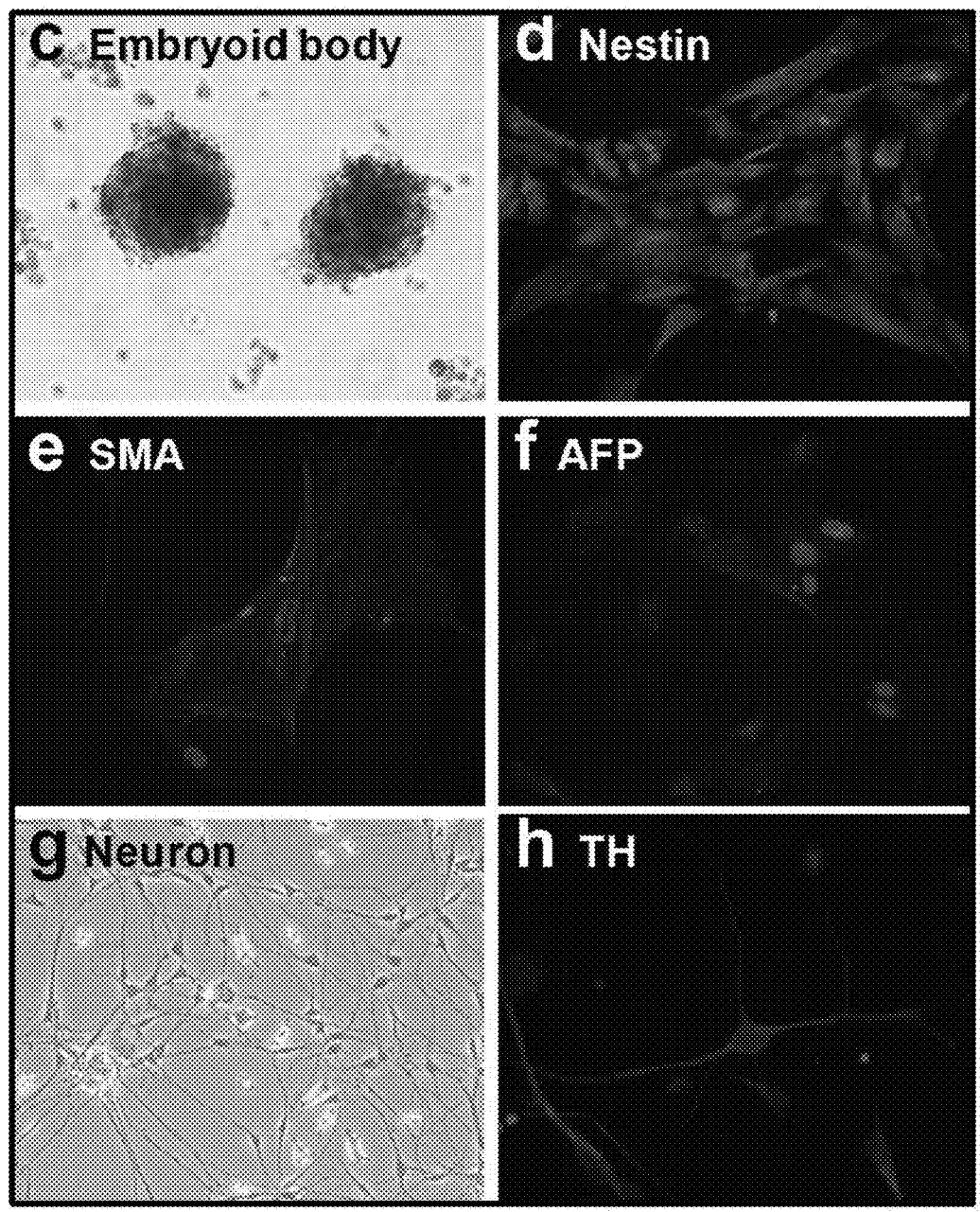
FIG. 12 shows immunohistochemistry data from differentiated iPS cells in accordance with another aspect of the present disclosure.

One of the useful characteristics of pluripotency is the ability of iPS cells to differentiate into all three germ layers. The following non-limiting example is provided to show such differentiation. For example, for in vitro differentiation, freshly prepared iPS cells with Ad-SOcMK as have been described were cultured in ES cell medium without basic fibroblast growth factor (bFGF) for 8-9 days. The resultant embryoid bodies (EBs) in suspension cultures (see FIG. 12, panels c-j) are allowed to differentiate further in chamber slides. After 9-10 days in adherent culture, attached cells show various types of morphologies. Immunocytochemistry reveals the detection of Nestin (ectoderm, FIG. 12, panel d), smooth muscle actin (SMA) (mesoderm, FIG. 12, panel e), and alpha-fetoprotein (AFP) (endoderm, FIG. 12, panel f). To test whether iPS cells could be differentiated into neurons, iPS cells are seeded on inactivated MEF cells and cultured for 22-25 days. Morphological and immunostaining data revealed that the iPS cells were differentiated into neurons with a subpopulation of neurons staining with the dopaminergic marker tyrosine hydroxylase (TH) (FIG. 12, panels g, h).

Figure 13:
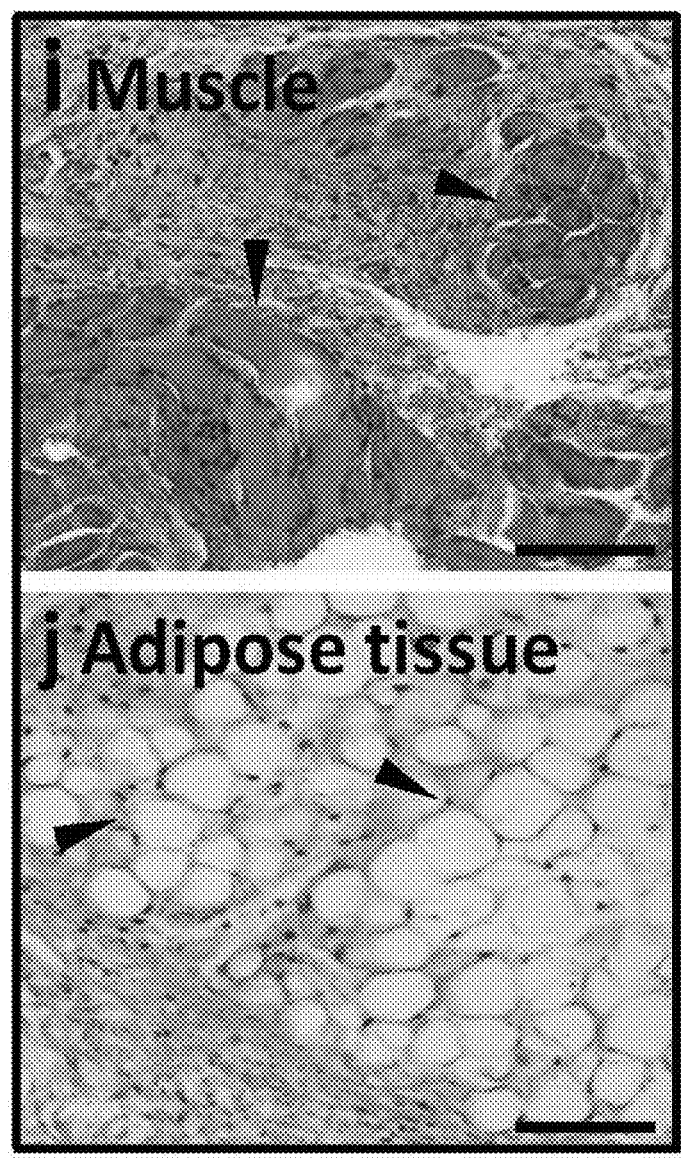
FIG. 13 shows histological data revealing development of muscle and adipose tissues in accordance with another aspect of the present disclosure.

To examine developmental potential in vivo, iPS cells generated with Ad-SOcMK are injected into NOD/SCID mice subcutaneously. After 9-10 weeks, teratomas develop and histological data reveals development of muscle and adipose tissues (mesoderm) (FIG. 13, panels I, j). Thus, iPS cells generated according to aspects of the present disclosure show pluripotency with the potential of differentiating into germ layers in vitro and in vivo.

Figure 14:
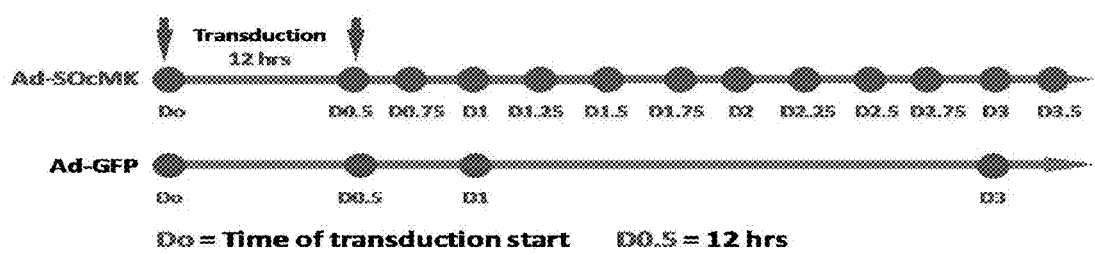
FIG. 14 shows an illustration of an experimental time line in accordance with another aspect of the present disclosure.

As has been described, traditional methods for reprogramming of human primary somatic cells have low efficiency, making the molecular characterization of reprogramming difficult. Given the rapid time course and absence of feeder cell contamination, the techniques according to aspects of the present disclosure can allow monitoring of expression changes at multiple time points during the reprogramming process as compared to just the beginning (fibroblasts) and final (iPS cells) time points. In one aspect, therefore, RNAs are isolated from Ad-SOcMK and Ad-GFP transduced IMR90 cells at 0, 24, 48 and 72 hrs post-transduction and queried for global gene expression changes by hybridization to oligonucleotide arrays representing 27,958 protein coding genes and 7,419 lincRNAs. Differential expression analyses (>2 fold change) shows changes in 6,852 genes for 0/24 hr, 12,945 for 0/48 hr, and 14,158 for 0/72 hr (data not shown). Based on the significant and rapid changes in global gene expression, the experiment is repeated and RNA expression is analyzed at 6 hr intervals for 84 hrs after Ad-SOcMK transduction. FIG. 14 shows an illustration of the experimental time line. To identify temporal waves of gene expression across time points, the entire data set is analyzed, including Ad-GFP-transduced control cells (>1.5-fold differential expression) by using singular value decomposition (SVD)25.

Figure 15A:
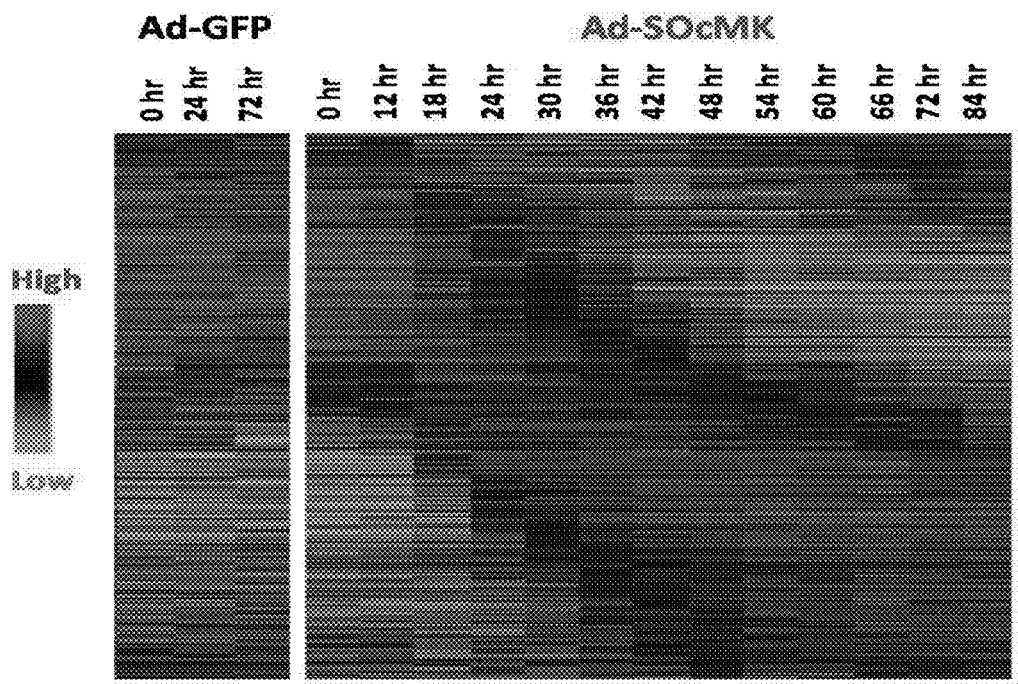
FIG. 15A shows a heat-map of a gene expression profile in accordance with another aspect of the present disclosure.
Figure 15B:
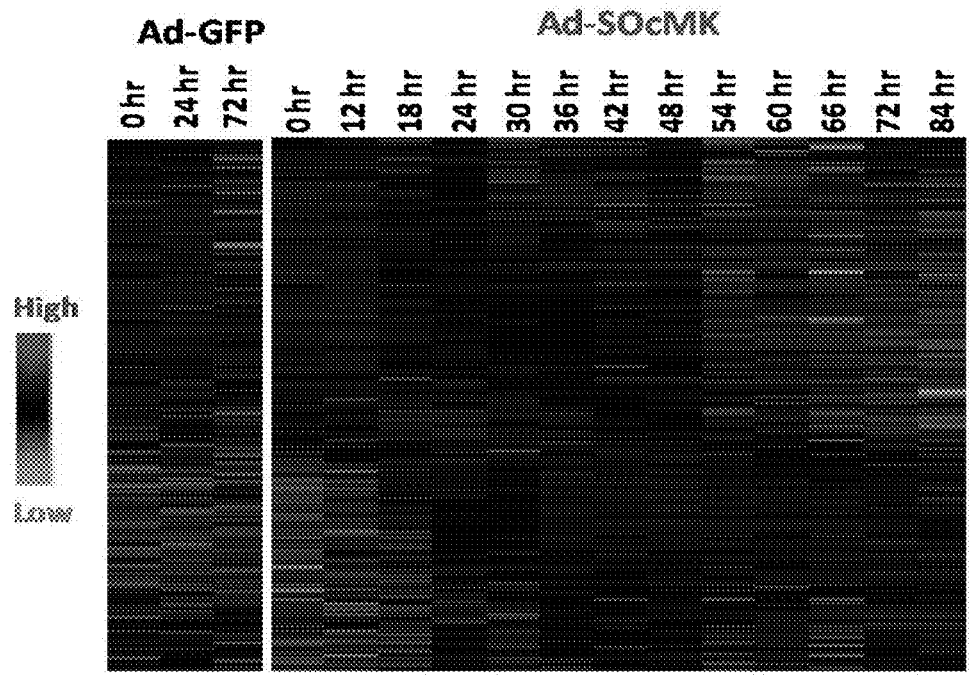
FIG. 15B shows a heat-map of a gene expression profile in accordance with another aspect of the present disclosure.

FIG. 15A shows a heat-map of the gene expression profile for this data set including lincRNAs (21,372 genes). As can be seen in FIG. 15A, a large class of RNAs is highly expressed in IMR90 cells with rapid reduction in the following 12-24 hrs. A second class of RNAs shows little change initially, and then exhibits increased expression with a return to or below initial levels by 72-84 hrs. Additionally, genes in a third group have low expression in the first 24-48 hrs, but then become highly expressed from that time on. Similar clustering of lincRNA expression can be observed (>four-fold differential expression, 1059 lincRNAs, FIG. 15B). Of note, changes in a large number of genes would have remained undetectable as the expression levels were similar at 0/12 hrs compared with 74/82 hrs, while expression greatly changed at the intervening time points.

Gene ontology and KEGG annotation can then be used to examine pathway-wide changes (Table 1). To do this, the heat-map of gene expression (FIG. 15A) is broken down into an early wave: 10%-40% percentile genes, an intermediate wave: 40%-75% percentile genes, and a late wave: 75%-95% percentile genes. Genes related to cytokine-cytokine receptor interactions are up-regulated in the early wave and remain so through 72 hrs (z-score >4.1 at all time points). Genes related to hedgehog signaling show increased expression in the intermediate and late waves (z-score >4.3). Genes involved in DNA replication and cell cycle genes are down-regulated in the intermediate and late wave (z-score >6.2). Additionally, it was validated that various randomly selected genes are specifically enriched or down regulated in ES cells from the two microarray data sets by real-time PCR. For all genes, expression changes are in the same direction within the same order of magnitude (data not shown).

TABLE 1

KEGG pathway genes

| Wave | KEGG Pathway | Gene Set | Number of Genes Up | Number of Genes Down | z-score (Up) | z-score (Down) |
|---|---|---|---|---|---|---|
| Early | Cytokine-cytokine receptor interaction | 265 | 13 | | 4.14 | |
| Intermediate | Hedgehog signaling pathway | 56 | 14 | | 4.89 | |
| | Cytokine-cytokine receptor interaction | 265 | 41 | | 4.88 | |
| | Protein digestion and absorption | 78 | 16 | | 4.29 | |
| Late | Cytokine-cytokine receptor interaction | 265 | 57 | | 5.87 | |
| | Gastric acid secretion | 74 | 20 | | 4.6 | |
| | Malaria | 49 | 15 | | 4.55 | |
| | Hedgehog signaling pathway | 56 | 16 | | 4.37 | |
| | Neuroactive ligand-receptor interaction | 311 | 55 | | 4.14 | |
| Intermediate | Cell cycle | 122 | | 27 | | 7.21 |
| | DNA replication | 35 | | 12 | | 6.78 |
| | Oocyte meiosis | 111 | | 19 | | 4.68 |
| | TGF-beta signaling pathway | 83 | | 15 | | 4.4 |
| Late | DNA replication | 35 | | 16 | | 6.98 |
| | Cell cycle | 122 | | 33 | | 6.23 |
| | Homologous recombination | 27 | | 11 | | 5.27 |

TABLE 1-continued

KEGG pathway genes

| Wave | KEGG Pathway | Gene Set | Number of Genes Up | Number of Genes Down | z-score (Up) | z-score (Down) |
|---|---|---|---|---|---|---|
| | Systemic lupus erythematosus | 122 | | 27 | | 4.42 |
| | Pathways in cancer | 325 | | 56 | | 4.34 |
| | Pancreatic cancer | 70 | | 18 | | 4.33 |
| | TGF-beta signaling pathway | 83 | | 20 | | 4.23 |

As has been described, in some aspects an altered promoter can be utilized to alter the expression of a particular reprogramming factor. The expression of the reprogramming factor can be increased or decreased, depending on the desired results. In one specific aspect, a weakened CMV promoter (CMV$_{WP}$) can be utilized. It should be understood that the discussion of the CMV$_{WP}$ should not be seen as limiting, and is merely exemplary. Because of strong promoter activity, CMV promoter (589 bp) has previously been used in mammalian system to express a protein in order to study protein functionality. Decreasing the expression of a reprogramming factor can be beneficial in the reprogramming process. In some cases, overexpression of a protein may actually hamper the reprogramming process. As such, in some cases factors can be tuned to more beneficial rates of expression. Additionally, by decreasing the size of the CMV promoter without interruption of promoter activity, a greater sequence size can be loaded into the expression vector. To this end, CMV$_{WP}$ has been developed to, among other reasons, regulate protein expression and allow a higher amount of genetic material to be cloned into a single cassette.

Figure 16:
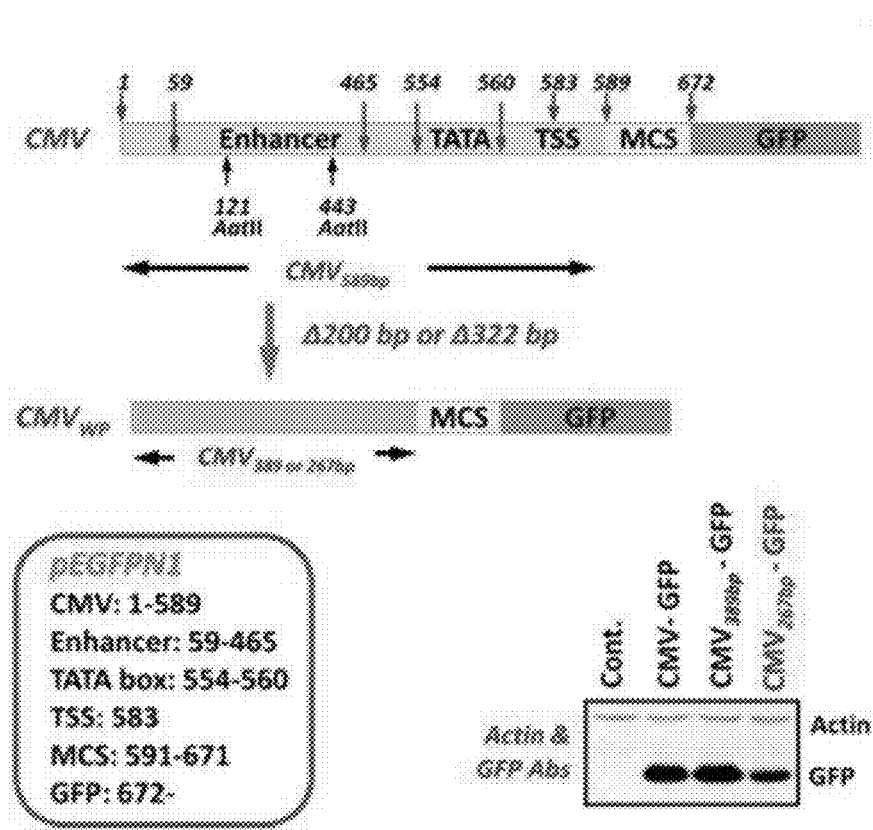
FIG. 16 shows the construction of a CMV weak promoter in accordance with another aspect of the present disclosure.

The inventors have constructed a series of mutant CMV promoters by deleting 200 or 322 bp from original CMV promoter (CMV$_{589\ bp}$) sequence of pEGFPN1 (Clontech Inc., USA) plasmid using either PCR or restriction digestion methods. The resultant mutant CMV promoters are tested for promoter activity by Western blot analyses expressing in HEK293 or SH-SY5Y cells. Of these, CMVA$_{A(121-443)bp}$-GFP construct, designated as CMV weak promoter-GFP (CMV$_{WP}$-GFP) results in the significant reduction of the GFP protein expression by >60% when compared with CMV$_{589\ bp}$-GFP or CMV$_{A(1-200)bp}$-GFP. As is shown in FIG. 16, construction of CMV promoter variants is shown. 200 bp deleted from the 5' end through PCR or 322 bp deleted by AatII digestion from the CMV promoter region of pEGFPN1 is shown in the upper panel of FIG. 16. Validation of promoter activity is shown in the lower panel of FIG. 16. Protein extracts from HEK293 or SH-SY5Y cells transfected with CMV promoter variants were subjected to Western blot analyses using the antibodies indicated. The blots were re-probed for Actin as an internal loading control. CMV$_{A(121-443)bp}$ promoter [CMV weak promoter (CMV$_{WP}$)] results in significant reduction of GFP protein expression.

Figure 17:
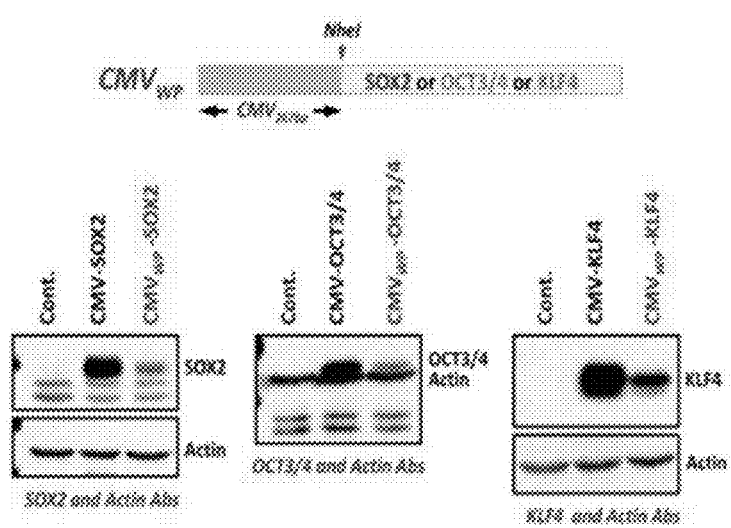
FIG. 17 shows the validation of the CMV weak promoter in accordance with another aspect of the present disclosure.

In order to validate this CMV$_{WP}$ activity further, reprogramming factors OCT3/4, SOX2, KLF4 and c-MYC genes were cloned separately into pre-GFP deleted CMV$_{WP}$-GFP plasmid at NheI site and tested for promoter activity by Western blot analyses expressing in HEK293 or SH-SY5Y cells. The Western blot data revealed the reduction of promoter activity of CMV$_{WP}$ by >70% when compared with CMV$_{589\ bp}$ promoter (See FIG. 17).

iPS cells are then generated using the CMV$_{WP}$ in the viral cassette as has previously been disclosed for the CMV promoter. In short, IMR90 cells are plated at a density of 1.5~2.5×10$^6$ cells per 10 cm tissue culture dish without feeder cells. The next day (day 2), IMR90 cells are about 60-70% confluent and the cells are transduced with medium (DMEM, 5% FBS, 1% NEAA, 0.5% penicillin-streptomycin) containing adenoviruses, Ad-GFP (control) or Ad(CMV$_{WP}$)-GFP-cMKSO viruses. From day 3 onward, the culture medium is replaced with human ES cell medium including DMEM/F12, 20% Knockout Serum Replacement (KSR), 1× nonessential amino acids, 1× sodium pyruvate, 1× L-glutamine, 0.1 mM b-mercaptoethanol, 25 ng/ml basic fibroblast growth factor (bFGF), and 0.5% penicillin-streptomycin. The medium is changed every day and incubated for 7-8 days. By days 4-7, several colonies showing ES cell-like morphology emerge and all colonies look identical, as shown in FIG. 18B. The resultant colonies (iPSCs) can be further expanded or subjected to characterization. SEQ ID 2, SEQ ID 3, and SEQ ID 4 are examples of adenovirus cassettes utilizing CMV$_{WP}$.

Additionally, as has been described, the undifferentiated state of human ES/iPS cells express high levels of membrane alkaline phosphatase (ALP) and ALP staining can be used to characterize the stem cells. For ALP staining, iPS cells are generated from iMR90 cells in 12 wells plate using the methods described. An experimental timeline is shown in FIG. 18A. At day 4, iPS cells are fixed with 4% paraformaldehyde for 2 minutes, followed by 15-minute incubation with staining solution (Alkaline Phosphatase Detection Kit; Millipore). ALP staining data demonstrates the positive staining for iPS cells, as is shown in FIG. 18C. As such, the CMV$_{WP}$ promoter can be utilized to generate iPS cells according to the methods and techniques described herein.

EXAMPLES

Materials

Reprogramming factors: OCT3/4, SOX2, GKLF4 and c-Myc. Plasmids containing the reprogramming factors (pEP4 E02S ET2K, pCEP4-M2L, pEP4 E02S EN2K, pEP4 E02S CK2M EN2L) are purchased from Addgene Inc., USA.

Each of the reprogramming factors was PCR amplified from the plasmids with NheI restriction sites. The authenticity of each gene was verified by NheI restriction digestion analyses and DNA sequencing.

Plasmid, pEGP-N1 (4.7 kb) is purchased from Clontech Inc., USA.

Adenoviral plasmid (pAdEasy-1, 33.4 kb), Shuttle vectors (pAdTrack and pAdTrack-CMV), Competent cells (Ad-Easier cells: *E coli* BJ5183 containing pAdEasy-1 backbone), and Packaging cells (HEK 293A) were generous gift from CoraliePoizet, Larry Kedes Lab, University of Southern California, Los Angeles, Calif., USA.

All enzymes related to cloning experiments are purchased from New England Biolabs Inc., USA.

Human embryonic fibroblast IMR90 cells were obtained from the American Type Culture Collection (ATCC), Catalog No. CCL-186. IMR90 cells were maintained in DMEM medium containing 10% fetal bovine serum (FBS).

Human skeletal muscle cells (SkMCs) were obtained from Lonza Inc., USA, Catalog NO. CC-2661. SkMCs were maintained in SkGM medium (catalog #3160, Lonza Inc., USA), containing 10% FBS.

Human spinocerebellar ataxia 2 (SCA2) skin fibroblasts containing (CAG)57 were obtained from Coriell Cell Repositories, USA Catalog No. #GM04319. SCA2 skin fibroblasts were cultured in MEM medium containing 15% FBS.

DMEM (Invitrogen, cat. no. 11965-092)
Fetal bovine serum, FBS (Hyclone, Thermo Scientific)
KO serum replacement (KOSR; Invitrogen, cat. no. 10828-028)
PBS without Ca/Mg (Hyclone, Thermo Scientific)
L-Gln, 100× (Invitrogen Inc.,)
Nonessential amino acid solution (NEAA) (Invitrogen Inc.,)
2-Mercaptoethanol, 1000×, 55 mM (Invitrogen Inc.,)
Sodium Pyruvate, 100× (Invitrogen Inc.,)
Basic fibroblast growth factor (bFGF; Invitrogen, cat. no. 13256-029)
7.5% BSA solution (wt/vol; Invitrogen, cat. no. 15260-037)
Penicillin/streptomycin, 100× (Invitrogen Inc.,)
0.25% Trypsin/EDTA (Invitrogen, cat. no. 25200-056)
0.05% Trypsin/EDTA (Invitrogen, cat. no. 25300-054)
Collagenase type IV (Invitrogen, cat. no. 17104-019)
Attachment factor, AF 1×, (Invitrogen, cat. no. 17104-019)
Equipment
Inverted tissue culture microscope with phase contrast microscope, Nikon Eclipse, TS100 (5×, 10×, 20×, 40× objectives)
Stereomicroscope (Nikon; SMZ-1500 or similar)
Incubator, Hera cell 240i, Thermo Scientific
Biosafety cabinet with aspirator for tissue culture
Biosafety cabinet with aspirator for tissue culture, fitted for stereomicroscope
Tissue culture centrifuge, Sorvall, Legend X1 Centrifuge, Thermo Scientific.
Tissue culture dishes and Flasks, 100 mm, 150 mm and T-25
Tissue culture plates, 4, 6 and 12-well
Filter unit: Millex-HV, PVDF, 0.45 µm, 33 mm, Millipore Inc.,
Conical tubes, 15 and 50 ml
Water bath Isotemp (Fisher Scientific, USA)
Plastic disposable transfer pipettes, 1, 5, 10 and 25 ml
Glass disposable transfer pipettes, 5 ml
Disposable sterile filter system (0.22 µm, 250 ml and 500 ml)
Disposable syringes, 60, 30, 10 and 1 ml
Hypodermic needle, 27-30G
Freezing container (Nalgene Labware, cat. no. 5100)
Cell lifter (Corning, cat. no. 3008)
Reagent Setup
Culture medium 1 (CM-1): DMEM, 10% FBS, and 1% penicillin-streptomycin Transduction medium: culture medium 2 (CM-2): DMEM, 5% FBS, 1% NEAA, and 0.5% penicillin-streptomycin.

Culture medium 3 (CM-3): DMEM, 10% FBS, 1% NEAA, and 0.5% penicillin-streptomycin.

Mouse embryo fibroblast (MEF) medium: DMEM, 10% FBS, 1% NEAA, and 0.5% penicillin-streptomycin.

hiPS cell medium: DMEM/F12 containing 20% KOSR (vol/vol), 50 ng/ml bFGF, 1× L-Gln, 1×NEAA, 1× Sodium Pyruvate, 100 µM 2-mercaptoethanol, 50 U/ml penicillin, and 50 mg/ml streptomycin.

2× cell-freezing medium: DMEM, 20% DMSO (vol/vol), 40% FBS (vol/vol), and 1% penicillin-streptomycin 2× iPS cell-freezing medium: DMEM/F12, 20% DMSO (vol/vol), 60% FBS (vol/vol), and 20% hiPS medium (vol/vol).

Example 1: Cloning of Reprogramming Factors

Cloning techniques follow methods published in Molecular cloning (A laboratory manual by Tom Maniatis, J. Sambrook, and E. F. Fritsch), which is incorporated herein by reference.

pEGFP-N1 plasmid (4.7 kb; purchased from Clontech Inc., USA.) is digested with BglII and NotI to remove the GFP open reading frame (ORF) from the plasmid backbone. The digestion reaction mix is as follows:

| | |
|---|---|
| pEGFP-N1 Plasmid DNA (1 µg/ul) | 10 µl |
| 10X Buffer | 5 µl |
| BglII (10 U/µl) | 1 µl |
| NotI (10 U/µl) | 1 µl |
| H2O | 33 µl |
| Total | 50 µl |

The digestion reaction mix is incubated at 37° C. for 3-4 hrs. Heat inactivation is performed at 65° C. for 30 min. The digested product is then electrophoresed on a 0.8% agarose gel and the plasmid back bone (3.9 kb) is purified using a gel extraction kit (Qiagen).

Each of the reprogramming factors (OCT3/4, SOX2, GKLF4 and c-Myc) are PCR amplified from pEP4 E02S ET2K or pCEP4-M2L or pEP4 E02S EN2K or pEP4 E02S CK2M EN2L plasmids (Addgene) with NheI restriction sites. The PCR products are cloned into pEGFP N1 (GFP deletion) at NheI site from the above digestion reaction. The ligation reaction mix is as follows:

| | |
|---|---|
| Vector DNA (10 ng/µl) | 1 µl |
| Insert DNA (PCR product) | 5 µl |
| 10X Buffer | 2 µl |
| T4 DNA ligase (3 U/µl) | 1 µl |
| H2O | 11 µl |
| Total | 20 µl |

The ligation reaction mix is incubated at 16° C. for 18-24 hrs. The DNA is mixed with DH5α competent cells (New England Biolabs Inc.) and the transformation is performed. The cell suspension is inoculated onto 10 cm petri dishes containing LB-agar plus 50 µg/ml of kanamycin. The agar plates are incubated at 37° C. for 20-24 hrs. The positive clones of each gene are verified by NheI restriction digestion analyses and DNA sequencing.

In order to clone the four reprogramming factors into the pAdTrack shuttle vector, each cassette from the above reaction is consecutively subcloned into the shuttle vector (Sox2 cassette at HindIII site, OCT3/4 cassette at EcoRV site, KLF4 cassette at SalI site, and c-Myc cassette at NotI site), designated as pAdSOcMK shuttle vector, as is shown in FIG. 1. The ligation reaction mix is as follows:

| | |
|---|---|
| pShuttle Vector DNA (10 ng/μl) | 1 μl |
| Insert DNA (CMV-SOX2-SV40PA) (10 ng/μl) | 5 μl |
| 10X Buffer | 2 μl |
| T4 DNA ligase (3 U/μl) | 1 μl |
| H2O | 11 μl |
| Total | 20 μl |

The ligation reaction mix is incubated at 16° C. for 18-24 hrs. The DNA is mixed with DH5α competent cells and the transformation is performed. The cell suspension is inoculated onto 10 cm petri dishes containing LB-agar plus 50 μg/ml of kanamycin. The agar plates are incubated at 37° C. for 20-24 hrs. The positive clones of each gene are verified by restriction digestion analyses and DNA sequencing.

Example 2: Generation of Recombinant Adenoviral Plasmids by Homologous Recombination in *E. coli* (FIG. 1)

High competence bacterial cells (*E coli* BJ5183) are utilized in the following methods to achieve efficient recombination.

Recombinant pAdShuttle plasmid clones containing the reprogramming factors (pAdSOcMK) from Example 1 are grown in 4.0 ml LB/kanamycin in a 5-ml conical tube, and shaken overnight in a 37° C. orbital shaker. The plasmid DNA is purified by an alkaline lysis procedure. It has been found that efficient homologous recombination in AdEasier-cells is improved by maintaining the integrity of the shuttle vector DNAs. Plasmids purified with commercial DNA minipreparation kits can contain significant numbers of nicked DNA molecules that may be detrimental to efficient and faithful recombination. The conventional alkaline lysis procedure can provide consistent and reliable results.

The recombinant shuttle vector plasmid is linearized by digesting with the restriction endonuclease PmeI, and purified using a gel extraction kit (Qiagen). The digestion reaction mix is as follows:

| | |
|---|---|
| Recombinant shuttle vector DNA (1 μg/μl) | 10 μl |
| 10X Buffer | 5 μl |
| PmeI (10 U/μl) | 1 μl |
| 100X BSA | 0.5 μl |
| H2O | 33.5 μl |
| Total | 50 μl |

The digestion reaction is incubated at 37° C. for 3-4 hrs. Heat inactivation is performed at 65° C. for 30 min. The digested product is electrophoresed on a 0.8% agarose gel and the plasmid back bone is purified using a gel extraction kit (Qiagen).

10 μl (100 ng/μl) of the linearized plasmid is mixed with 50-100 μl of *E. coli* BJ5183 cells and incubated on ice for 40-60 min. The bacteria/DNA mix is then heat shockedat 42° C. for 1.5-2 min and immediately incubated on ice for 0.5-1 min. The cells are immediately placed in 250-300 μl of LB-Broth and grown at 37° C. for 1.5-2 hrs.

100 μl of the cell suspension is inoculated onto each of three 10 cm petri dishes containing LB-agar plus 50 μg/ml of kanamycin. The agar plates are incubated at 24-30° C. for 2-3 days until colonies appear. Each colony is isolated and grown in 4 ml LB medium containing 50 μg/ml of kanamycin at 24-30° C. for 2 days in an orbital shaker.

Plasmid DNA is isolated using the conventional alkaline lysis method. PacI restriction digestion is performed on candidate clones. Correct recombinants usually yield a large fragment (~30 kb) and a smaller fragment of 4.5 kb. 1-3 μl of correct recombinant plasmids (pAdSOcMK adenoviral vector) are retransformed into DH10B competent cells. The correct clones are subjected to restriction enzyme and/or PCR analysis to verify authenticity. The plasmids are purified with Pure Link Maxi Kit (Invitrogen Inc.,) in order to transfect into the packaging cells (HEK 293A cells) for virus production.

Example 3: Adenovirus Production in Packaging Cells (HEK 293A)

Day 1: HEK 293A cells (E1-transformed human embryonic kidney cells) are plated at a density of $1-2 \times 10^6$ cells per T-25 flask in cell culture medium containing DMEM, 10% FBS, and 1% penicillin-streptomycin. The cells are incubated at 37° C., 5% $CO_2$ for 24 hr.

Day 2: The confluencycan be about 50-70% at the time of transfection. The recombinant adenoviral plasmids (pAdSOcMK) are digested with PacI (often 5 μg DNA is needed for one transfection). The digested plasmids are ethanol precipitated and resuspended in 25-30 μl of sterile $H_2O$. A standard lipofectamine transfection is performed according to manufacturer's protocol (Invitrogen Inc.). Mix 5 μg of PacI-digested plasmid and 25 μl of Lipofectamine in 500 μl of OptiMem I medium, and incubate at room temperature for 15-30 min. While waiting, medium from the recipient cells can be removed and the cells can be wash once with a serum-free medium (DMEM). 2.5-3.0 ml Opti-Mem I is added to a T-25 flask containing the cells. Incubate the cells (37° C., 5% CO2) for 10-15 min. The lipofectamine-DNA mix is added to the flasks with the cells and returned to the incubator for 5-6 hrs. The lipofectamine/DNA medium is removed and 5-7 ml of fresh cell culture medium is added, and the cells are incubated at 37° C., 5% CO2.

Incubation continues until ~90% of the cells detach (die) from the flask surface. This often takes approximately 20-30 days. Transfections and viral production can be monitored by GFP expression. The cells are scraped off the flask with a scrapper at 20-30 days post-transfection and the medium with the cells is collected in 15/50 ml conical tubes. The tubes are spun in a benchtop centrifuge, and supernatant (sup 1) is collected and the pellet is resuspended in 2-3 ml sterile PBS. The cells are frozen in a dry ice/methanol bath or a −80° C. freezer, thawed in a 37° C. water bath, and vortexed vigorously. This procedure of freeze/thaw/vortex is repeated for 3-4 more cycles. The samples are spun briefly, and the supernatant (sup 2) is collected. Sup 1 and sup 2 are mixed (hereinafter "adenovirus particles"). The adenovirus particles are filtered with a 0.45 μm syringe filter and stored at −20/−80° C. until use.

Example 4: Amplification of Adenoviruses

Two 50-70% confluent T-25 flasks of HEK 293A cells are infected using 40-50% of the viral supernatant containing the adenovirus particles from Example 3 for each flask. Cytopathic effect (CPE) or cell lysis should appear at 7-10 days post infection. Effective production of adenoviruses can be monitored by GFP expression. When ≥90% of the cells die, the cells are scraped off and adenoviral supernatant is prepared as described in Example 3. Authenticity of recombinant adenovirus can be confirmed by infecting the viral supernatant to any infectable cells and Western blot and/or PCR analyses of target genes. Multiple rounds of infection cycles in HEK 293A cells can be carried out to harvest adenoviral particles.

Example 5: Generation of iPS Cells by Adenoviral Vector Containing Multi-Reprogramming Factors from IMR90 Human Fetal Fibroblasts without Using Feeder Cells Human embryonic fibroblast IMR90 cells are purchased from the American Type Culture Collection (ATCC) (Manassas, Va., http://www.atcc.org; Catalog No. CCL-186). IMR90 cells are cultured and maintained in culture medium 1 (CM-1) containing DMEM, 10% FBS, and 1% penicillin-streptomycin according to manufacturer's protocol.

The fibroblasts IMR90 are thawed as follows:
1. Prepare 9 ml of CM-1 in a 15 ml conical tube.
2. A vial of frozen fibroblasts is removed from the liquid nitrogen tank and placed into a 37° C. water bath until most (but not all) cells are thawed.
3. The vial is wiped with ethanol, the cap is opened, and the cell suspension is transferred to the tube prepared in step 1.
4. The tube is centrifuged at 1100 rpm for 3 minutes, and the supernatant is discarded.
5. The cells are re-suspended in 10 ml of CM-1, and transferred to a 100 mm dish (0.5-1×105 cells/dish). The cells are incubated in a 37° C., 5% CO2 incubator until the cells become 80~90% confluent. The medium is changed every other day.

The fibroblasts are passaged as follows:
1. The medium is discarded the cells are washed once with PBS.
2. The PBS is aspirated, and 1.5 ml per dish of 0.05% trypsin/0.53 mM EDTA is added, and the cells are incubated for 1-2 minutes at 37° C.
3. 8.5 ml of CM-1 is added, and the cells are separated into a single cell suspension by pipetting up and down several times.
4. The cell suspension is adjusted to 40 ml by the addition of CM-1 medium, and transferred to dishes (10 ml per 10 mm dish). Thus the cells are divided up in a 1:4 ratio. The cells are incubated at 37° C., 5% CO2 until the cells become 80-90% confluent. This commonly takes 4~5 days after passage.

Adenoviral transduction is accomplished as follows:
Day 1: IMR90 cells are plated at a density of 1.5~2.5×10$^6$ cells per 10 cm tissue culture dish in CM-1 without feeder cells and incubated at 37° C., 5% $CO_2$ for 24 hr.
Day 2: When IMR90 cells are about 60-70% confluent, the culture medium is removed and the cells are transduced with culture medium 2 (CM-2) including DMEM, 5% FBS, 1% NEAA, 0.5% penicillin-streptomycin and also containing adenovirus particles as generated in either of Examples 3 and 4, Ad-GFP or Ad-SOK or Ad-SOcMK at 100-500 pfu/cell. The cells are incubated at 37° C., 5% CO2 for 24 hr.
Day 3: The culture medium is changed with culture medium 3 (CM-3) including of DMEM, 10% FBS, 1% NEAA, 0.5% penicillin-streptomycin. The cells are incubated at 37° C., 5% CO2 for 24 hr.
Day 4: Incubation continues. The medium is changed every day with CM-3 and incubated for more 3-4 days.
By days 4-7, several colonies showing ES cell-like morphology emerge and all colonies look identical, as shown in FIG. 3.

Example 6: Adenovirus Transduction and iPSC Generation

IMR90 cells (1.0-1.5×106) are cultured overnight on 100 mm dishes without feeder cells. On the following day, cells are transduced with Ad-SOcMK or Ad-GFP (control). Adenoviruses are removed at 24 hrs post-transduction (day 1), and replaced with human ES cell medium consisting of DMEM/F12 (#11330-32, Invitrogen Inc., USA), 20% Knockout Serum Replacement (KSR) (#10828-028, Invitrogen Inc., USA), 1× nonessential amino acids, 1× sodium pyruvate, 1× L-glutamine, 0.1 mM β-mercaptoethanol, 25 ng/ml basic fibroblast growth factor (bFGF) (#PHG0263, Invitrogen Inc., USA), and 0.5% penicillin-streptomycin. The medium is changed every day and by days 2-3, several colonies showing ES cell-like morphology emerged on the dish. The same protocol is used to generate iPSCs from SkMCs and SCA2 patient skin fibroblasts. Feeder cells are not used.

Example 7: Western Blot Analysis

Protein extracts are resolved by SDS-PAGE and transferred to Hybond P membranes (Amersham Bioscience Inc., USA). After blocking with 5% skim milk in 0.1% Tween 20/PBS, the membranes are incubated with primary antibodies in 5% skim milk in 0.1% Tween 20/PBS for 2 hrs at room temperature or overnight at 4° C. After several washes with 0.1% Tween 20/PBS, the membranes are incubated with the corresponding secondary antibodies conjugated with HRP in 5% skim milk in 0.1% Tween 20/PBS for 2 hrs at room temperature. Following three additional washes with 0.1% Tween 20/PBS, signals are detected by using the Immobilon Western Chemiluminescent HRP Substrate (#WBKLSO100, Millipore Inc., USA) according to the manufacturer's protocol. The antibodies with their sources and dilutions are listed in Table 2.

TABLE 2

| | Antibodies | | | |
|---|---|---|---|---|
| Antibodies | Dilutions (Western blot) | Dilutions (Immunofluorescence) | Vendors name | Catalog # |
| Primary Antibodies: Monoclonal antibodies (mAb): | | | | |
| OCT-3/4 (C-10) | 1:5000 | | Santa Cruz Inc., USA | sc-5279 |
| GKLF (B-9) | 1:7000 | | " | sc-166100 |
| c-MYC (9E10) | 1:5000 | | " | sc-40 |

TABLE 2-continued

| Antibodies | | | | |
|---|---|---|---|---|
| Antibodies | Dilutions (Western blot) | Dilutions (Immunofluorescence) | Vendors name | Catalog # |
| SSEA-1 | | 1:500 | Millipore Inc., USA | MAB4301-20 |
| SSEA-3 | | 1:500 | " | MAB4303-20 |
| SSEA-4 | | 1:500 | " | MAB4304-20 |
| TRA-1-60 | | 1:500 | " | MAB4360-20 |
| TRA-1-81 | | 1:500 | " | MAB4381-20 |
| Smooth Muscle Actin (SMA) | | 1:500 | " | CBL171 |
| Alpha Feto Protein (AFP) | | 1:500 | " | 2004189 |
| Polyclonal antibodies (pAb): Host: Rabbit | | | | |
| SOX-2 (H-65) | 1:4000 | | Santa Cruz Inc., USA | sc-20088 |
| LIN-28 (H-44) | | 1:500 | " | sc-67266 |
| TERT (H-231) | | 1:500 | " | sc-7212 |
| NANOG | 1:3000 | 1:500 | Cell Signaling Tech., USA | 3580 |
| THY1 | 1:4000 | | " | 9798 |
| Nestin | | 1:500 | Millipore Inc., USA | AB5922 |
| mAb conjugated with HRP: | | | | |
| Beta-Actin (AC-15) | 1:10000 | | Sigma Inc., USA | A3854 |
| Secondary Antibodies: Conjugation: HRP | | | | |
| anti-mouse IgG | 1:5000 | | Sigma Inc., USA | A2304 |
| anti-rabbit IgG | 1:5000 | | Santa Cruz Inc., USA | sc-2077 |
| Conjugation: Dylight 549 | | | | |
| anti-mouse IgG | | 1:2000 | Fisher Scientific, USA | 35507 |
| anti-rabbit IgG | | 1:2000 | " | 35557 |

Example 8: Alkaline Phosphatase Staining and Immunocytochemistry

ALP Staining was Performed Using the Alkaline Phosphatase Detection Kit (#SCR004, Millipore Inc., USA). Briefly, iPS cells are fixed with 4% paraformaldehyde/PBS for 2 min, followed by 15 min incubation with staining solution according to the manufacturer's protocol. For immunocytochemistry, cells are fixed in 4% paraformaldehyde/PBS for 20 min at room temperature. The cells are then permeabilized with 70% ethanol and stored at 4° C. After washing with PBS, cells were blocked with 10% BSA/PBS for 2 hrs at room temperature. Slides were incubated with primary antibodies in 10% BSA/PBS for 2 hrs at room temperature or overnight at 4° C., washed three times with PBS and incubated with the corresponding secondary antibodies conjugated with Dylight variants. Following incubation, cells are washed three times with PBS and nuclei stained with 4',6-diamidino-2-phenylindole (DAPI) (Sigma Inc., USA). The slides are mounted with mounting medium, Vectashield (Vector Inc., USA) and cells visualized using confocal microscopy (Nikon Eclipse Ti microscopy). The antibodies with their sources and dilutions are listed in Table 2.

Example 9: PCR Analysis

Total RNA is prepared from harvested cells using the RNAeasy Kit (Qiagen Inc., USA). cDNA is synthesized from 5 µg of total RNA using MMLV reverse transcriptase and random hexanucleotide primers (New England Biolab Inc., USA) according to the manufacturer's protocol. To study gene expression of iPS cells, cDNAs (150 ng for semi-quantitative and 5 ng for real-time PCR) derived from the total RNA is subjected to PCR analysis. In regular PCR, the PCR products are cloned and verified by sequencing. Primer sequences used for semi-quantitative and real-time PCR are listed in Tables 3 and 4.

TABLE 3

| Primers |
|---|
| CDH1 |
| Forward: SEQ ID 5 |
| 5'-AGCCATGGGCCCTTGGAGCCGCAG-3' |
| Reverse: SEQ ID 6 |
| 5'-GGAATAACCCAGTCTCTCTTCTGTC-3' |
| |
| GAL |
| Forward: SEQ ID 7 |
| 5'-TGCGGCCCGAAGATGACATGAAACC-3' |
| Forward: SEQ ID 8 |
| 5'-CCCAGGAGGCTCTCAGGACCGCTC-3' |
| |
| THY1 |
| Forward: SEQ ID 9 |
| 5'-GAGGAGGCTGCAGCAGCGGAAGAC-3' |
| Forward: SEQ ID 10 |
| 5'-GAGCCAGCAGGCTGATGCCCTCAC-3' |
| |
| GABRB3 |
| Forward: SEQ ID 11 |
| 5'-CCTTGCCCAAAATCCCCTATGTCAAAGC-3' |
| Reverse: SEQ ID 12 |
| 5'-GTATCGCCAATGCCGCCTGAGACCTC-3' |
| |
| NANOG |
| Forward: SEQ ID 13 |
| 5'-ATTATAAATCTAGAGACTCCAGG-3' |
| Reverse: SEQ ID 14 |
| 5'-CATGGAGGAAGGAAGAGGAGAGAC-3' |

TABLE 3 -continued

Primers

TDGF1
Forward: SEQ ID 15
5'-CTGCTGCCTGAATGGGGGAACCTGC-3'
Reverse: SEQ ID 16
5'-GCCACGAGGTGCTCATCCATCACAAGG-3'

ALPL
Forward: SEQ ID 17
5'-TTATAAGGCGGCGGGGGTGGTGGC-3'
Reverse: SEQ ID 18
5'-CGAAGGGGAACTTGTCCATCTCCAG-3'

NODAL
Forward: SEQ ID 19
5'-ATCATCCGCAGCCTACAGGCAG-3'
Reverse: SEQ ID 20
5'-CTGTCCCTCCTGGGCCCGCCAGG-3'

TERT
Forward: SEQ ID 21
5'-CCTGCTCAAGCTGACTCGACACCGTG-3'
Reverse: SEQ ID 22
5'-GGAAAAGCTGGCCCTGGGGTGGAGC-3'

PODXL2
Forward: SEQ ID 23
5'-CTCAACCAGCAGCTCCTAGAAGGG-3'
Reverse: SEQ ID 24
5'-GCTGGCCCGCGCCTGGCAGCTGC-3'

GDF3
Forward: SEQ ID 25
5'-CTTATGCTACGTAAAGGAGCTGGG-3'
Reverse: SEQ ID 26
5'-GTGCCAACCCAGGTCCCGGAAGTT-3'

GAPDH
Forward: SEQ ID 27
5'-TGAAGGTCGGAGTCAACGGATTTGG-3'
Reverse: SEQ ID 28
5'-GGAGGCCATGTGGGCCATGAG-3'

FGF4
Forward: SEQ ID 29
5'-CTACAACGCCTACGAGTCCTACAAG-3'
Reverse: SEQ ID 30
5'GTTGCACCAGAAAAGTCAGAGTTG-3'

OCT3/4*
Forward: SEQ ID 31
5'-AGGAGTCCCAGGACATCAAAGCTCTG-3'
SOX2*
Forward: SEQ ID 32
5'-CCGGCGGCAATAGCATGGCGAGCGG-3'

DPPA4
Forward: SEQ ID 33
5'-ATATCCCGCCGTGGGTGAAAGTTC-3'
Reverse: SEQ ID 34
5'-ACTCAGCCATGGACTGGAGCATCC-3'

KLF4*
Forward: SEQ ID 35
5'-TCCAATTCGCTGACCCATCCTCCG-3'

IFITM1
Forward: SEQ ID 36
5'-CCCCAAAGCCAGAAGATGCACAAGGAGG-3'
Reverse: SEQ ID 37
5'-CGTCGCCAACCATCTTCCTGTCCCTAG-3' c-MYC*
Forward: SEQ ID 38
5'-ATGGTGACCGAGCTGCTGGGAGGAG-3'

TABLE 3 -continued

Primers

Poly A*
Reverse: SEQ ID 39
5'-ATACATTGATGAGTTTGGACAAAC-3'

*Primers used for exogenous gene.

TABLE 4

Primers

THY1
Forward: SEQ ID 40
5'-GAGGAGGCTGCAGCAGCGGAAGAC-3'
Reverse: SEQ ID 41
5'-CCACTAGGCAGGCCGTTAGGCTGG-3'

TDGF1
Forward: SEQ ID 42
5'-GGATACAGCACAGTAAGGAGC-3'
Reverse: SEQ ID 43
5'-GCACAGACCCACAGTTCTC-3'

OCT3/4
Forward: SEQ ID 44
5'-TCTCCCATGCATTCAAACTGAG-3'
Reverse: SEQ ID 45
5'-CCTTTGTGTTCCCAATTCCTTC-3'

GDF3
Forward: SEQ ID 46
5'-CCCGAGACTTATGCTACGTAAAG-3'
Reverse: SEQ ID 47
5'-GGCAGACAGGTTAAAGTAGAGG-3'

NANOG
Forward: SEQ ID 48
5'-AGCTACAAACAGGTGAAGACC-3'
Reverse: SEQ ID 49
5'-GTGGTAGGAAGAGTAAAGGCTG-3'

ALPL
Forward: SEQ ID 50
5'-GATGTGGAGTATGAGAGTGACG-3'
Reverse: SEQ ID 51
5'-GGTCAAGGGTCAGGAGTTC-3'

TERT
Forward: SEQ ID 52
5'-GCACGGCTTTTGTTCAGATG-3'
Reverse: SEQ ID 53
5'-CGGTTGAAGGTGAGACTGGC-3'

GABRB3
Forward: SEQ ID 54
5'-CAAGGCAAAGAATGACCGTTC-3'
Reverse: SEQ ID 55
5'-TGCTGAATTCCTGGTATCGC-3'

LIN28
Forward: SEQ ID 56
5'-GCAGAAGCGCAGATCAAAAG-3'
Reverse: SEQ ID 57
5'-CGGACATGAGGCTACCATATG-3'

NODAL
Forward: SEQ ID 58
5'-AGGAGTTTCATCCGACCAAC-3'
Reverse: SEQ ID 59
5'-TCTGCCATTATCCACATACAGC-3'

IFITM4
Forward: SEQ ID 60
5'-ATCAACATCCACAGCGAGAC-3'
Reverse: SEQ ID 61
5'-CAACCATCTTCCTGTCCCTAG-3'

TABLE 4 -continued

Primers

```
FGF4
Forward: SEQ ID 62
5'-CCATGAAGGTCACCCACTTC-3'
Reverse: SEQ ID 63
5'-CTCTTGCATTAAACTCTTCATCCG-3'

PODXL2
Forward: SEQ ID 64
5'-CCCAGCGAAGAGAATGAAGAG-3'
Reverse: SEQ ID 65
5'-AATGGAACCTGCCTTCTCAG-3'

CDH1
Forward: SEQ ID 66
5'-CCCAATACATCTCCCTTCACAG-3'
Reverse: SEQ ID 67
5'-CCACCTCTAAGGCCATCTTTG-3'

GAL
Forward: SEQ ID 68
5'-GCGCACAATCATTGAGTTTCTG-3'
Reverse: SEQ ID 69
5'-AGACAAACATGCCC AGGAGG-3'

GAPDH
Forward: SEQ ID 70
5'-GAAGGTGAAGGTCGGAGTCAACG-3'
Reverse: SEQ ID 71
5'-GAAGATGGTGATGGGATTTCC-3'
```

Example 10: Bisulfite Sequencing

To assess the methylation status of CpGs in the promoter region of NANOG, genomic DNA is purified from IMR90 cells transduced with Ad-GFP or Ad-SOcMK using the DNeasy Kit (Qiagen Inc., USA). Purified genomic DNA (1 µg) is used to convert unmethylated cytosines (C) to uracil (U) using EZ DNA methylation kit (#D5001, Zymo Research Inc., USA), according to the manufacturer's protocol. Treated DNA is purified with QIAquick column (Qiagen Inc., USA) and purified DNA (150 ng) from each sample is subjected to PCR analyses for the promoter region of NANOG using the following primers: forward 5'-CAC-CATGCGTGGCTAATTTTTGTA-3', reverse 5'-TTAAAATCCTGGAGTCTCTAGATTT-3'. The resulting PCR products are subcloned into the pCR2.1-TOPO vector (Invitrogen Inc., USA). Ten clones of each sample are verified by sequencing.

Example 11: In Vitro Differentiation

To determine the differentiation ability of iPS cells in vitro, the floating culture method is used to form Embryoid bodies (EBs). Briefly, IMR90 cells are transduced with Ad-SOcMK. On day 3, the resultant iPS cells are mechanically dissociated and cultured in ES cell medium (without bFGF) in non-coated T25 flasks. The medium is changed every other day. After 7 days in floating culture, ball-shaped structures typical for EBs are formed. EBs are then transferred to 0.1% gelatin-coated chamber slides using the same medium. The medium is changed every other day once EBs are attached to the slide. Differentiated cells are fixed after 8 days in adherent culture and stained with antibodies recognizing marker proteins for each germ layer.

Example 12: Teratoma Formation

To examine the in vivo development potential of iPS cells, IMR90 cells are transduced with Ad-SOcMK. On day 3, the resultant iPSCs are injected subcutaneously to 4 of 6-week-old male nonobese diabetic severe combined immunodeficient (NOD/SCID) mice (Charles River Laboratories) (3×106 iPSCs for each mouse). For control experiment, IMR90 cells (3×106 cells) are also injected into one mouse. After 9-10 weeks, tumors are dissected and fixed in 4% paraformaldehyde. Teratoma experiments are conducted in Comparative Oncology Resource Core at the University of Utah. Samples are embedded in paraffin and stained with hematoxylin and eosin in the Tissue Resource and Application Core (TRAC) at the University of Utah. All procedures are performed in accordance with protocols approved by the University of Utah Animal Research Committee guidelines.

Example 12: Microarray Analyses

IMR90 cells are transduced with Ad-SOcMK or Ad-GFP. Adenoviruses are removed at 12 hrs post-transduction and cells are sampled at every 6 hrs. Total RNA is prepared from each sample using Qiagen RNeasy kit according to manufacturer's protocol. Human genome SurePrintG3 8×60K carrying 27,958 genes and 7,419 LincRNA targets (Agilent Technologies, Inc.) are used for microarray hybridization to examine the global gene expression. Approximately 1 µg of RNA from each sample is labeled using Agilent Two-Color Quick Amp Labeling Kit following manufacturer's instructions. All arrays are hybridized at 65° C. for 17 hrs and scanned using an Agilent scanner G2505C. The gene expression raw data is extracted using Agilent Feature Extraction Software version 10.5. Quality control is done on the basis of Agilent quality control metrics. Singular value decomposition (SVD) of the qualified data, with gene expression centered at its time average, identified several "eigengenes," i.e., significant patterns of expression variation across time. Sorting the data according to the two most significant eigengenes gives a global picture of the dynamics of gene expression, in which individual genes appear to be classified into groups of similar regulation and function 25. Array experiments are performed in Microarray Core Facility at the University of Utah.

Of course, it is to be understood that the above-described arrangements are only illustrative of the application of the principles of the present disclosure. Numerous modifications and alternative arrangements may be devised by those skilled in the art without departing from the spirit and scope of the present disclosure and the appended claims are intended to cover such modifications and arrangements. Thus, while the present disclosure has been described above with particularity and detail in connection with what is presently deemed to be the most practical embodiments of the disclosure, it will be apparent to those of ordinary skill in the art that numerous modifications, including, but not limited to, variations in size, materials, shape, form, function and manner of operation, assembly and use may be made without departing from the principles and concepts set forth herein.

What is claimed is:

1. A method of generating iPS cells, comprising:

cloning nucleic acid sequences encoding OCT3/4, SOX2, and at least one protein selected from the group consisting of KLF4, c-Myc, NANOG, or LIN28 into separate vectors, wherein each nucleic acid sequence is operably linked to a separate promoter;

cloning each nucleic acid sequence operably linked to a separate promoter into a single shuttle vector;

linearizing the shuttle vector;

introducing the shuttle vector into an expression vector for virus production;

producing a viral particle containing the expression vector;

transducing mammalian somatic cells in vitro with the viral particle; and culturing the transduced mammalian somatic cells in vitro for a period of time such that iPS cells are obtained.

2. The method of claim 1, wherein the nucleic acid sequences are cloned into separate vectors using blunt end ligation.

3. The method of claim 1, wherein the transduced mammalian somatic cells are cultured in vitro in the absence of feeder cells, in the absence of a matrigel matrix, or in the absence of feeder cells and a matrigel matrix such that iPS cells are obtained.

4. The method of claim 1, wherein the expression vector is selected from the group consisting of adenoviral vectors, episomal vectors, retroviral vectors, and lentiviral vectors.

5. The method of claim 1, wherein the expression vector is an episomal vector.

6. The method of claim 1, wherein the expression vector has a sequence that is at least 80% homologous to SEQ ID 72.

7. The method of claim 1, wherein the expression vector has a sequence that is at least 95% homologous to SEQ ID 72.

8. The method of claim 1, wherein at least one nucleic acid sequence is under control of a CMV promoter.

9. The method of claim 8, wherein the CMV promoter is a weak CMV promoter.

10. The method of claim 1, wherein the expression vector further includes a reporter sequence under control of a separate promoter.

* * * * *

UNITED STATES PATENT AND TRADEMARK OFFICE
CERTIFICATE OF CORRECTION

PATENT NO. : 9,920,333 B2
APPLICATION NO. : 14/984861
DATED : March 20, 2018
INVENTOR(S) : Stefan M. Pulst Page 1 of 1

It is certified that error appears in the above-identified patent and that said Letters Patent is hereby corrected as shown below:

In the Specification

Column 1 Line 18, delete "This invention was made with government support under grant numbers R01NS33123 and RC4NS073009 from the National Institutes of Neurological Disorders and Stroke. The United States government has certain rights to this invention." and replace it with the following:

--This invention was made with government support under grant NS073009 and R01 NS033123 awarded by the National Institutes of Health. The government has certain rights in this invention.--

Signed and Sealed this
Tenth Day of September, 2019

Andrei Iancu
*Director of the United States Patent and Trademark Office*

SEQUENCE LISTING

<160> NUMBER OF SEQ ID NOS: 72

<210> SEQ ID NO 1
<211> LENGTH: 16309
<212> TYPE: DNA
<213> ORGANISM: Artificial Sequence
<220> FEATURE:
<223> OTHER INFORMATION: The adeno shuttle vector containing
      multi-reprogramming factors has been provided as complementary
      sequence (pAd-kcMOS). In the text, it should be read as pAd-SOcMK
      (S; SOX2, O; OCT3/4, cM; c-MYC, K; KLF4)
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (12)..(14)
<223> OTHER INFORMATION: n is a, c, g, or t
<220> FEATURE:
<221> NAME/KEY: misc_feature
<222> LOCATION: (355)..(357)
<223> OTHER INFORMATION: n is a, c, g, or t
<220> FEATURE:
<221> NAME/KEY: misc_feature
<222> LOCATION: (1945)..(1947)
<223> OTHER INFORMATION: n is a, c, g, or t
<220> FEATURE:
<221> NAME/KEY: misc_feature
<222> LOCATION: (7317)..(7317)
<223> OTHER INFORMATION: n is a, c, g, or t
<220> FEATURE:
<221> NAME/KEY: misc_feature
<222> LOCATION: (10202)..(10204)
<223> OTHER INFORMATION: n is a, c, g, or t
<220> FEATURE:
<221> NAME/KEY: misc_feature
<222> LOCATION: (12445)..(12447)
<223> OTHER INFORMATION: n is a, c, g, or t
<220> FEATURE:
<221> NAME/KEY: misc_feature
<222> LOCATION: (12462)..(12464)
<223> OTHER INFORMATION: n is a, c, g, or t
<220> FEATURE:
<221> NAME/KEY: misc_feature
<222> LOCATION: (13447)..(13449)
<223> OTHER INFORMATION: n is a, c, g, or t
<220> FEATURE:
<221> NAME/KEY: misc_feature
<222> LOCATION: (13464)..(13466)
<223> OTHER INFORMATION: n is a, c, g, or t
<220> FEATURE:
<221> NAME/KEY: misc_feature
<222> LOCATION: (14767)..(14772)
<223> OTHER INFORMATION: n is a, c, g, or t

<400> SEQUENCE: 1

| | | | | | |
|---|---|---|---|---|---|
| nnnttaatta | annntccctt | ccagctctct | gccccttttg | gattgaagcc | aatatgataa | 60 |
| tgaggggtg | gagtttgtga | cgtggcgcgg | ggcgtgggaa | cggggcgggt | gacgtagtag | 120 |
| tgtggcggaa | gtgtgatgtt | gcaagtgtgg | cggaacacat | gtaagcgacg | gatgtggcaa | 180 |
| aagtgacgtt | tttggtgtgc | gccggtgtac | acaggaagtg | acaattttcg | cgcggtttta | 240 |
| ggcggatgtt | gtagtaaatt | tgggcgtaac | cgagtaagat | ttggccattt | tcgcgggaaa | 300 |
| actgaataag | aggaagtgaa | atctgaataa | ttttgtgtta | ctcatagcgc | gtaannncgc | 360 |
| gttaagatac | attgatgagt | ttggacaaac | cacaactaga | atgcagtgaa | aaaaatgctt | 420 |
| tatttgtgaa | atttgtgatg | ctattgcttt | atttgtaacc | attataagct | gcaataaaca | 480 |
| agttaacaac | aacaattgca | ttcattttat | gtttcaggtt | caggggagg | tgtgggaggt | 540 |
| tttttaaagc | aagtaaaacc | tctacaaatg | tggtatggct | gattatgatc | agttatctag | 600 |

```
atccggtgga tctgagtccg gacttgtaca gctcgtccat gccgagagtg atcccggcgg    660
cggtcacgaa ctccagcagg accatgtgat cgcgcttctc gttggggtct ttgctcaggg    720
cggactgggt gctcaggtag tggttgtcgg gcagcagcac ggggccgtcg ccgatggggg    780
tgttctgctg gtagtggtcg gcgagctgca cgctgccgtc ctcgatgttg tggcggatct    840
tgaagttcac cttgatgccg ttcttctgct tgtcggccat gatatagacg ttgtggctgt    900
tgtagttgta ctccagcttg tgccccagga tgttgccgtc ctccttgaag tcgatgccct    960
tcagctcgat gcggttcacc agggtgtcgc cctcgaactt cacctcggcg cgggtcttgt   1020
agttgccgtc gtccttgaag aagatggtgc gctcctggac gtagccttcg ggcatggcgg   1080
acttgaagaa gtcgtgctgc ttcatgtggt cggggtagcg gctgaagcac tgcacgccgt   1140
aggtcagggt ggtcacgagg gtgggccagg gcacgggcag cttgccggtg gtgcagatga   1200
acttcagggt cagcttgccg taggtggcat cgccctcgcc ctcgccggac acgctgaact   1260
tgtggccgtt tacgtcgccg tccagctcga ccaggatggg caccaccccg gtgaacagct   1320
cctcgccctt gctcaccatg gtggcgaccg gtagcgctag cggatctgac ggttcactaa   1380
accagctctg cttatataga cctcccaccg tacacgccta ccgcccattt gcgtcaatgg   1440
ggcggagttg ttacgacatt ttggaaagtc ccgttgattt tggtgccaaa acaaactccc   1500
attgacgtca atggggtgga gacttggaaa tccccgtgag tcaaaccgct atccacgccc   1560
attgatgtac tgccaaaacc gcatcaccat ggtaatagcg atgactaata cgtagatgta   1620
ctgccaagta ggaaagtccc ataaggtcat gtactgggca taatgccagg cgggccattt   1680
accgtcattg acgtcaatag ggggcgtact tggcatatga tacacttgat gtactgccaa   1740
gtgggcagtt taccgtaaat actccaccca ttgacgtcaa tggaaagtcc ctattggcgt   1800
tactatggga acatacgtca ttattgacgt caatgggcgg gggtcgttgg gcggtcagcc   1860
aggcgggcca tttaccgtaa gttatgtaac gcggaactcc atatatgggc tatgaactaa   1920
tgaccccgta attgattact attannncta gcagatctgg taccgtcgat aatagtaatc   1980
aattacgggg tcattagttc atagcccata tatggagttc cgcgttacat aacttacggt   2040
aaatggcccg cctggctgac cgcccaacga ccccgcccca ttgacgtcaa taatgacgta   2100
tgttcccata gtaacgccaa tagggacttt ccattgacgt caatgggtgg agtatttacg   2160
gtaaactgcc cacttggcag tacatcaagt gtatcatatg ccaagtacgc cccctattga   2220
cgtcaatgac ggtaaatggc ccgcctggca ttatgcccag tacatgacct tatgggactt   2280
tcctacttgg cagtacatct acgtattagt catcgctatt accatggtga tgcggttttg   2340
gcagtacatc aatgggcgtg gatagcggtt tgactcacgg ggatttccaa gtctccaccc   2400
cattgacgtc aatgggagtt tgttttggca ccaaaatcaa cgggactttc caaaatgtcg   2460
taacaactcc gccccattga cgcaaatggg cggtaggcgt gtacggtggg aggtctatat   2520
aagcagagct ggtttagtga accgtcagat ccgctagcat ggctgtcagc gacgcgctgc   2580
tcccatcttt ctccacgttc gcgtctggcc cggcgggaag ggagaagaca ctgcgtcaag   2640
caggtgcccc gaataaccgc tggcgggagg agctctccca catgaagcga cttccccag    2700 tgcttcccgg ccgcccctat gacctggcgg cggcgaccgt ggccacagac ctggagagcg   2760
gcggagccgg tgcggcttgc ggcggtagca acctggcgcc cctacctcgg agagagaccg   2820
aggagttcaa cgatctcctg gacctggact ttattctctc caattcgctg acccatcctc   2880
cggagtcagt ggccgccacc gtgtcctcgt cagcgtcagc ctcctcttcg tcgtcgccgt   2940
cgagcagcgg ccctgccagc gcgccctcca cctgcagctt cacctatccg atccgggccg   3000
```

```
ggaacgaccc gggcgtggcg ccgggcggca cgggcggagg cctcctctat ggcagggagt    3060
ccgctccccc tccgacggct cccttcaacc tggcggacat caacgacgtg agcccctcgg    3120
gcggcttcat ggccgagctc ctgcggccag aattggaccc ggtgtacatt ccgccgcagc    3180
agccgcagcc gccaggtggc gggctgatgg gcaagttcgt gctgaaggcg tcgctgagcg    3240
cccctggcag cgagtacggc agcccgtcgg tcatcagcgt cagcaaaggc agccctgacg    3300
gcagccaccc ggtggtggtg gcgccctaca acggcgggcc gccgcgcacg tgccccaaga    3360
tcaagcagga ggcggtctct tcgtgcaccc acttgggcgc tggacccccct ctcagcaatg    3420 gccaccggcc ggctgcacac gacttccccc tggggcggca gctccccagc aggactaccc    3480
cgaccctggg tcttgaggaa gtgctgagca gcagggactg tcaccctgcc ctgccgcttc    3540
ctccggcttc catcccccac ccgggcccaa attacccatc cttcctgccc gatcagatgc    3600
agccgcaagt cccgccgctc cattaccaag agctcatgcc acccggttcc tgcatgccag    3660
aggagcccaa gccaaagagg ggaagacgat cgtggcccccg gaaaaggacc gccacccaca    3720
cttgtgatta cgcgggctgc ggcaaaaacct acacaaagag ttcccatctc aaggcacacc    3780
tgcgaaccca cacaggtgag aaaccttacc actgtgactg ggacggctgt ggatggaaat    3840
tcgcccgctc agatgaactg accaggcact accgtaaaca cacggggcac cgcccgttcc    3900
agtgccaaaa atgcgaccga gcattttcca ggtcggacca cctcgcctta cacatgaaga    3960
ggcattttta agctagcgct accggactca gatcggccgc gactctagat cataatcagc    4020
cataccacat ttgtagaggt tttacttgct ttaaaaaaacc tcccacacct cccctgaac    4080 ctgaaacata aaatgaatgc aattgttgtt gttaacttgt ttattgcagc ttataatggt    4140
tacaaataaa gcaatagcat cacaaatttc acaaataaag catttttttc actgcattct    4200
agttgtggtt tgtccaaact catcaatgta tcttaatcga cgcggcctaa tagtaatcaa    4260
ttacggggtc attagttcat agcccatata tggagttccg cgttacataa cttacggtaa    4320
atggcccgcc tggctgaccg cccaacgacc cccgcccatt gacgtcaata atgacgtatg    4380
ttcccatagt aacgccaata gggactttcc attgacgtca atgggtggag tatttacggt    4440
aaactgccca cttggcagta catcaagtgt atcatatgcc aagtacgccc cctattgacg    4500
tcaatgacgg taaatggccc gcctggcatt atgcccagta catgacctta tgggactttc    4560
ctacttggca gtacatctac gtattagtca tcgctattac catggtgatg cggttttggc    4620
agtacatcaa tgggcgtgga tagcggtttg actcacgggg atttccaagt ctccacccca    4680
ttgacgtcaa tgggagtttg ttttggcacc aaaatcaacg ggactttcca aaatgtcgta    4740
acaactccgc cccattgacg caaatgggcg gtaggcgtgt acggtgggag gtctatataa    4800
gcagagctgt ttagtgaac cgtcagatcc gctagcatgc cctcaacgt agcttcacc    4860 aacaggaact atgacctcga ctacgactcg gtgcagccgt atttctactg cgacgaggag    4920
gagaacttct accagcagca gcagcagagc gagctgcagc cccggcgcc cagcgaggat    4980 atctggaaga aattcgagct gctgcccacc ccgcccctgt ccctagccg ccgctccggg    5040 ctctgctcgc cctcctacgt tgcggtcaca cccttctccc ttcggggaga caacgacggc    5100
ggtggcggga gcttctccac ggccgaccag ctggagatgg tgaccgagct gctgggagga    5160
gacatggtga accagagttt catctgcgac ccggacgacg agaccttcat caaaaacatc    5220
atcatccagg actgtatgtg gagcggcttc tcggccgccg ccaagctcgt ctcagagaag    5280
ctggcctcct accaggctgc gcgcaaagac agcggcagcc cgaaccccgc ccgcggccac    5340
```

```
agcgtctgct ccacctccag cttgtacctg caggatctga gcgccgccgc ctcagagtgc      5400
atcgacccct cggtggtctt ccctaccct ctcaacgaca gcagctcgcc caagtcctgc       5460
gcctcgcaag actccagcgc cttctctccg tcctcggatt ctctgctctc ctcgacggag      5520
tcctccccgc agggcagccc cgagccctg gtgctccatg aggagacacc gcccaccacc       5580
agcagcgact ctgaggagga caagaagat gaggaagaaa tcgatgttgt ttctgtggaa       5640
aagaggcagg ctcctggcaa aaggtcgag tctggatcac cttctgctgg aggccacagc       5700
aaacctcctc acagcccact ggtcctcaag aggtgccacg tctccacaca tcagcacaac      5760
tacgcagcgc ctccctccac tcggaaggac tatcctgctg ccaagagggt caagttggac      5820
agtgtcagag tcctgagaca gatcagcaac aaccgaaaat gcaccagccc caggtcctcg      5880
gacaccgagg agaatgtcaa gaggcgaaca cacaacgtct tggagcgcca gaggaggaac      5940
gagctaaaac ggagcttttt tgccctgcgt gaccagatcc cggagttgga aaacaatgaa      6000
aaggccccca aggtagttat ccttaaaaaa gccacagcat acatcctgtc cgtccaagca      6060
gaggagcaaa agctccattc tgaagaggac ttgttgcgga aacgacgaga acagttgaaa      6120
cacaaacttg aacagctacg gaactcttgt gcgtaagcta gcgctaccgg actcagatcg      6180
gccgcgactc tagatcataa tcagccatac cacatttgta gaggttttac ttgctttaaa      6240
aaacctccca cacctccccc tgaacctgaa acataaaatg aatgcaattg ttgttgttaa      6300
cttgtttatt gcagcttata atggttacaa ataaagcaat agcatcacaa atttcacaaa      6360
taaagcattt ttttcactgc attctagttg tggtttgtcc aaactcatca atgtatctta      6420
aggccgcgat taatagtaat caattacggg gtcattagtt catagcccat atatggagtt      6480
ccgcgttaca taacttacgg taaatggccc gcctggctga ccgcccaacg acccccgccc      6540
attgacgtca ataatgacgt atgttcccat agtaacgcca atagggactt tccattgacg      6600
tcaatgggtg gagtatttac ggtaaactgc ccacttggca gtacatcaag tgtatcatat      6660
gccaagtacg ccccctattg acgtcaatga cggtaaatgg cccgcctggc attatgccca      6720
gtacatgacc ttatgggact ttcctacttg gcagtacatc tacgtattag tcatcgctat      6780
taccatggta atgcggtttt ggcagtacat caatgggcgt ggatagcggt ttgactcacg      6840
gggatttcca agtctccacc ccattgacgt caatgggagt ttgttttggc accaaaatca      6900
acgggacttt ccaaaatgtc gtaacaactc cgccccattg acgcaaatgg gcggtaggcg      6960
tgtacggtgg gaggtctata taagcagagc tggtttagtg aaccgtcaga tccgctagca      7020
tggcgggaca cctggcttcg gatttcgcct tctcgccccc tccaggtggt ggaggtgatg      7080 ggccagggggg gccggagccg ggctgggttg atcctcggac ctggctaagc ttccaaggcc      7140
ctcctggagg gccaggaatc gggccggggg ttgggccagg ctctgaggtg tggggggattc     7200 ccccatgccc cccgccgtat gagttctgtg ggggatggc gtactgtggg ccccaggttg       7260
gagtggggct agtgccccaa gcggcttgg agacctctca gcctgagggt gaagcangag       7320
tcggggtgga gagcaactcc gatggggcct ccccggagcc ctgcaccgtc acccctggtg      7380
ccgtgaagct ggagaaggag aagctggagc aaaacccgga ggagtccag gacatcaaag       7440 ctctgcagaa agaactcgag caatttgcca agctcctgaa gcagaagagg atcaccctgg      7500
gatatacaca ggccgatgtg gggctcaccc tgggggttct atttgggaag gtattcagcc      7560
aaacgaccat ctgccgcttt gaggctctgc agcttagctt caagaacatg tgtaagctgc      7620
ggcccttgct gcagaagtgg gtggaggaag ctgacaacaa tgaaaatctt caggagatat      7680
gcaaagcaga aaccctcgtg caggcccgaa agagaaagcg aaccagtatc gagaaccgag      7740
```

```
tgagaggcaa cctggagaat ttgttcctgc agtgcccgaa acccacactg cagcagatca   7800
gccacatcgc ccagcagctt gggctcgaga aggatgtggt ccgagtgtgg ttctgtaacc   7860
ggcgccagaa gggcaagcga tcaagcagcg actatgcaca acgagaggat tttgaggctg   7920
ctgggtctcc tttctcaggg ggaccagtgt cctttcctct ggcccaggg ccccattttg    7980 gtacccagg ctatgggagc cctcacttca ctgcactgta ctcctcggtc cctttccctg    8040
agggggaagc ctttccccct gtctccgtca ccactctggg ctctcccatg cattcaaact   8100
gagctagcgc taccggactc agatcggccg cgactctaga tcataatcag ccataccaca   8160
tttgtagagg ttttacttgc tttaaaaaac ctcccacacc tccccctgaa cctgaaacat   8220
aaaatgaatg caattgttgt tgttaacttg tttattgcag cttataatgg ttacaaataa   8280
agcaatagca tcacaaattt cacaaataaa gcattttttt cactgcattc tagttgtggt   8340
ttgtccaaac tcatcaatgt atcttaaatc ctcgagaagc ttaatagtaa tcaattacgg   8400
ggtcattagt tcatagccca tatatggagt tccgcgttac ataacttacg gtaaatggcc   8460
cgcctggctg accgcccaac gacccccgcc cattgacgtc aataatgacg tatgttccca   8520
tagtaacgcc aatagggact ttccattgac gtcaatgggt ggagtattta cggtaaactg   8580
cccacttggc agtacatcaa gtgtatcata tgccaagtac gccccctatt gacgtcaatg   8640
acggtaaatg gcccgcctgg cattatgccc agtacatgac cttatgggac tttcctactt   8700
ggcagtacat ctacgtatta gtcatcgcta ttaccatggt gatgcggttt tggcagtaca   8760
tcaatgggcg tggatagcgg tttgactcac ggggatttcc aagtctccac cccattgacg   8820
tcaatgggag tttgttttgg caccaaaatc aacgggactt tccaaaatgt cgtaacaact   8880
ccgccccatt gacgcaaatg ggcggtaggc gtgtacggtg ggaggtctat ataagcagag   8940
ctggtttagt gaaccgtcag atccgctagc atgtacaaca tgatggagac ggagctgaag   9000
ccgccgggcc cgcagcaaac ttcggggggc ggcggcggca actccaccgc ggcggcggcc   9060
ggcggcaacc agaaaaacag cccggaccgc gtcaagcggc ccatgaatgc cttcatggtg   9120
tggtcccgcg ggcagcggcg caagatggcc caggagaacc ccaagatgca caactcggag   9180
atcagcaagc gcctgggcgc cgagtggaaa cttttgtcgg agacggagaa gcggccgttc   9240
atcgacgagg ctaagcggct gcgagcgctg cacatgaagg agcacccgga ttataaatac   9300
cggccccggc ggaaaaccaa gacgctcatg aagaaggata gtacacgct gcccggcggg    9360 ctgctggccc ccggcggcaa tagcatggcg agcggggtcg gggtgggcgc cggcctgggc   9420
gcgggcgtga accagcgcat ggacagttac gcgcacatga acggctggag caacggcagc   9480
tacagcatga tgcaggacca gctgggctac ccgcagcacc cgggcctcaa tgcgcacggc   9540
gcagcgcaga tgcagcccat gcaccgctac gacgtgagcg ccctgcagta caactccatg   9600
accagctcgc agacctacat gaacggctcg cccacctaca gcatgtccta ctcgcagcag   9660
ggcacccctg gcatggctct tggctccatg ggttcggtgg tcaagtccga ggccagctcc   9720 agccccctg tggttacctc ttcctcccac tccagggcgc cctgccaggc cggggacctc   9780
cgggacatga tcagcatgta tctcccccgg gccgaggtgc cggaacccgc cgcccccagc   9840
agacttcaca tgtcccagca ctaccagagc ggcccggtgc ccggcacggc cattaacggc   9900
acactgcccc tctcacacat gtgagctagc gctaccggac tcagatcggc cgcgactcta   9960
gatcataatc agccatacca catttgtaga ggttttactt gctttaaaaa acctcccaca   10020 cctcccccctg aacctgaaac ataaaatgaa tgcaattgtt gttgttaact tgtttattgc   10080
```

-continued

```
agcttataat ggttacaaat aaagcaatag catcacaaat ttcacaaata aagcatttt      10140
ttcactgcat tctagttgtg gtttgtccaa actcatcaat gtatcttaaa gctttctaga     10200
gnnntaaggg tgggaaagaa tatataaggt gggggtctta tgtagttttg tatctgtttt     10260
gcagcagccg ccgccgccat gagcaccaac tcgtttgatg gaagcattgt gagctcatat     10320
ttgacaacgc gcatgccccc atgggccggg gtgcgtcaga atgtgatggg ctccagcatt     10380
gatggtcgcc ccgtcctgcc cgcaaactct actaccttga cctacgagac cgtgtctgga     10440
acgccgttgg agactgcagc ctccgccgcc gcttcagccg ctgcagccac cgcccgcggg     10500
attgtgactg actttgcttt cctgagcccg cttgcaagca gtgcagcttc ccgttcatcc     10560
gcccgcgatg acaagttgac ggctcttttg gcacaattgg attctttgac ccgggaactt     10620
aatgtcgttt ctcagcagct gttggatctg cgccagcagg tttctgccct gaaggcttcc     10680
tcccctccca atgcggttta aaacataaat aaaaaaccag actctgtttg gatttggatc     10740
aagcaagtgt cttgctgtct ttatttaggg gttttgcgcg cgcggtaggc ccgggaccag     10800
cggtctcggt cgttgagggt cctgtgtatt ttttccagga cgtggtaaag gtgactctgg     10860
atgttcagat acatgggcat aagcccgtct ctggggtgga ggtagcacca ctgcagagct     10920
tcatgctgcg gggtggtgtt gtagatgatc cagtcgtagc aggagcgctg ggcgtggtgc     10980
ctaaaaatgt cttttcagtag caagctgatt gccaggggca ggcccttggt gtaagtgttt     11040
acaaagcggt taagctggga tgggtgcata cgtggggata tgagatgcat cttggactgt     11100
attttttaggt tggctatgtt cccagccata tccctccggg gattcatgtt gtgcagaacc     11160
accagcacag tgtatccggt gcacttggga aatttgtcat gtagcttaga aggaaatgcg     11220
tggaagaact tggagacgcc cttgtgacct ccaagatttt ccatgcattc gtccataatg     11280
atggcaatgg gcccacgggc ggcggcctgg gcgaagatat ttctgggatc actaacgtca     11340
tagttgtgtt ccaggatgag atcgtcatag gccatttta caaagcgcgg gcggagggtg     11400
ccagactgcg gtataatggt tccatccggc ccagggggcgt agttaccctc acagatttgc     11460
atttcccacg ctttgagttc agatgggggg atcatgtcta cctgcggggc gatgaagaaa     11520
acggtttccg gggtagggga atcagctgg gaagaaagca ggttcctgag cagctgcgac     11580
ttaccgcagc cggtgggccc gtaaatcaca cctattaccg ggtgcaactg gtagttaaga     11640
gagctgcagc tgccgtcatc cctgagcagg ggggccactt cgttaagcat gtccctgact     11700
cgcatgtttt ccctgaccaa atccgccaga aggcgctcgc cgcccagcga tagcagttct     11760
tgcaaggaag caaagttttt caacggtttg agaccgtccg ccgtaggcat gcttttgagc     11820
gtttgaccaa gcagttccag gcggtcccac agctcggtca cctgctctac ggcatctcga     11880
tccagcatat ctcctcgttt cgcgggttgg ggcggctttc gctgtacggc agtagtcggt     11940
gctcgtccag acgggccagg gtcatgtctt tccacgggcg cagggtcctc gtcagcgtag     12000
tctgggtcac ggtgaagggg tgcgctccgg gctgcgcgct ggccagggtg cgcttgaggc     12060
tggtcctgct ggtgctgaag cgctgccggt cttcgccctg cgcgtcggcc aggtagcatt     12120
tgaccatggt gtcatagtcc agcccctccg cggcgtggcc cttggcgcgc agcttgccct     12180
tggaggaggc gccgcacgag gggcagtgca gacttttgag ggcgtagagc ttgggcgcga     12240
gaaataccga ttccggggag taggcatccg cgccgcaggc cccgcagacg gtctcgcatt     12300
ccacgagcca ggtgagctct ggccgttcgg ggtcaaaaac caggtttccc ccatgctttt     12360
tgatgcgttt cttacctctg gtttccatga gccggtgtcc acgctcggtg acgaaaaggc     12420
tgtccgtgtc cccgtataca gactnnngtt taaacgaatt cnnntataaa atgcaaggtg     12480
```

```
ctgctcaaaa aatcaggcaa agcctcgcgc aaaaagaaa gcacatcgta gtcatgctca    12540
tgcagataaa ggcaggtaag ctccggaacc accacagaaa aagacaccat ttttctctca    12600
aacatgtctg cgggtttctg cataaacaca aataaaata acaaaaaaac atttaaacat    12660
tagaagcctg tcttacaaca ggaaaaacaa cccttataag cataagacgg actacggcca    12720
tgccggcgtg accgtaaaaa aactggtcac cgtgattaaa aagcaccacc gacagctcct    12780
cggtcatgtc cggagtcata atgtaagact cggtaaacac atcaggttga ttcatcggtc    12840
agtgctaaaa agcgaccgaa atagcccggg ggaatacata cccgcaggcg tagagacaac    12900
attacagccc ccataggagg tataacaaaa ttaataggag agaaaaacac ataaacacct    12960
gaaaaaccct cctgcctagg caaaatagca ccctcccgct ccagaacaac atacagcgct    13020
tcacagcggc agcctaacag tcagccttac cagtaaaaaa gaaaacctat taaaaaaaca    13080
ccactcgaca cggcaccagc tcaatcagtc acagtgtaaa aagggccaa gtgcagagcg    13140 agtatatata ggactaaaaa atgacgtaac ggttaaagtc cacaaaaaac acccagaaaa    13200
ccgcacgcga acctacgccc agaaacgaaa gccaaaaaac ccacaacttc ctcaaatcgt    13260
cacttccgtt ttcccacgtt acgtaacttc ccattttaag aaaactacaa ttcccaacac    13320
atacaagtta ctccgcccta aaacctacgt cacccgcccc gttcccacgc ccgcgccac    13380 gtcacaaact ccaccccctc attatcatat tggcttcaat ccaaaataag gtatattatt    13440
gatgatnnnt taattaagga tccnnncggt gtgaaatacc gcacagatgc gtaaggagaa    13500
aataccgcat caggcgctct tccgcttcct cgctcactga ctcgctgcgc tcggtcgttc    13560
ggctgcggcg agcggtatca gctcactcaa aggcggtaat acgttatcc acagaatcag    13620 gggataacgc aggaaagaac atgtgagcaa aaggccagca aaaggccagg aaccgtaaaa    13680
aggccgcgtt gctggcgttt ttccataggc tccgcccccc tgacgagcat cacaaaaatc    13740
gacgctcaag tcagaggtgg cgaaacccga caggactata agataccag gcgtttcccc    13800 ctggaagctc cctcgtgcgc tctcctgttc cgaccctgcc gcttaccgga tacctgtccg    13860
cctttctccc ttcgggaagc gtggcgcttt ctcatagctc acgctgtagg tatctcagtt    13920
cggtgtaggt cgttcgctcc aagctgggct gtgtgcacga accccccgtt cagcccgacc    13980
gctgcgcctt atccggtaac tatcgtcttg agtccaaccc ggtaagacac gacttatcgc    14040
cactggcagc agccactggt aacaggatta gcagagcgag gtatgtaggc ggtgctacag    14100
agttcttgaa gtggtggcct aactacggct acactagaag gacagtattt ggtatctgcg    14160
ctctgctgaa gccagttacc ttcggaaaaa gagttggtag ctcttgatcc ggcaaacaaa    14220
ccaccgctgg tagcggtggt ttttttgttt gcaagcagca gattacgcgc agaaaaaaag    14280
gatctcaaga agatcctttg atcttttcta cggggtctga cgctcagtgg aacgaaaact    14340
cacgttaagg gattttggtc atgagattat caaaaaggat cttcacctag atcctttaa    14400 attaaaaatg aagttttaaa tcaatctaaa gtatatatga gtaaacttgg tctgacagtt    14460
accaatgctt aatcagtgag gcacctatct cagcgatctg tctatttcgt tcatccatag    14520
ttgcctgact ccccgtcgtg tagataacta cgatacggga gggcttacca tctggcccca    14580
gtgctgcaat gataccgcga gacccacgct caccggctcc agatttatca gcaataaacc    14640
agccagccgg aagggccgag cgcagaagtg gtcctgcaac tttatccgcc tccatccagt    14700
ctattaattg ttgccgggaa gctagagtaa gtagttcgcc agttaatagt ttgcgcaacg    14760
ttgttgnnnn nnaaaaagga tcttcaccta gatcctttc acgtagaaag ccagtccgca    14820
```

```
gaaacggtgc tgaccccgga tgaatgtcag ctactgggct atctggacaa gggaaaacgc    14880
aagcgcaaag agaaagcagg tagcttgcag tgggcttaca tggcgatagc tagactgggc    14940
ggttttatgg acagcaagcg aaccggaatt gccagctggg gcgccctctg gtaaggttgg    15000
gaagccctgc aaagtaaact ggatggcttt ctcgccgcca aggatctgat ggcgcagggg    15060
atcaagctct gatcaagaga caggatgagg atcgtttcgc atgattgaac aagatggatt    15120
gcacgcaggt tctccggccg cttgggtgga gaggctattc ggctatgact gggcacaaca    15180
gacaatcggc tgctctgatg ccgccgtgtt ccggctgtca gcgcaggggc gcccggttct    15240
ttttgtcaag accgacctgt ccggtgccct gaatgaactg caagacgagg cagcgcggct    15300
atcgtggctg gccacgacgg gcgttccttg cgcagctgtg ctcgacgttg tcactgaagc    15360
gggaagggac tggctgctat tgggcgaagt gccggggcag gatctcctgt catctcacct    15420
tgctcctgcc gagaaagtat ccatcatggc tgatgcaatg cggcggctgc atacgcttga    15480
tccggctacc tgcccattcg accaccaagc gaaacatcgc atcgagcgag cacgtactcg    15540
gatggaagcc ggtcttgtcg atcaggatga tctggacgaa gagcatcagg ggctcgcgcc    15600
agccgaactg ttcgccaggc tcaaggcgag catgcccgac ggcgaggatc tcgtcgtgac    15660
ccatggcgat gcctgcttgc cgaatatcat ggtggaaaat ggccgctttt ctggattcat    15720
cgactgtggc cggctgggtg tggcggaccg ctatcaggac atagcgttgg ctacccgtga    15780
tattgctgaa gagcttggcg gcgaatgggc tgaccgcttc ctcgtgcttt acggtatcgc    15840
cgctcccgat tcgcagcgca tcgccttcta tcgccttctt gacgagttct tctgaatttt    15900
gttaaaattt ttgttaaatc agctcatttt ttaaccaata ggccgaaatc ggcaacatcc    15960
cttataaatc aaaagaatag accgcgatag ggttgagtgt tgttccagtt tggaacaaga    16020
gtccactatt aaagaacgtg gactccaacg tcaaagggcg aaaaaccgtc tatcagggcg    16080
atggcccact acgtgaacca tcacccaaat caagtttttt gcggtcgagg tgccgtaaag    16140
ctctaaatcg gaaccctaaa gggagccccc gatttagagc ttgacgggga aagccggcga    16200
acgtggcgag aaaggaaggg aagaaagcga aggagcgggc gctagggcg ctggcaagtg    16260 tagcggtcac gctgcgcgta accaccacac ccgcgcgctt aatgcgccg                16309
```

```
<210> SEQ ID NO 2
<211> LENGTH: 14736
<212> TYPE: DNA
<213> ORGANISM: Artificial Sequence
<220> FEATURE:
<223> OTHER INFORMATION: The adeno shuttle vector containing multi-RFs
      under CMV weak promoter (CMVWP) has been provided as
      pAd(CMVWP)-GFP-cMKSO (cM; c-Myc, K; KLF4, S; SOX2, O; OCT3/4).
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (12)..(14)
<223> OTHER INFORMATION: n is a, c, g, or t
<220> FEATURE:
<221> NAME/KEY: misc_feature
<222> LOCATION: (355)..(357)
<223> OTHER INFORMATION: n is a, c, g, or t
<220> FEATURE:
<221> NAME/KEY: misc_feature
<222> LOCATION: (7564)..(7564)
<223> OTHER INFORMATION: n is a, c, g, or t
<220> FEATURE:
<221> NAME/KEY: misc_feature
<222> LOCATION: (8622)..(8624)
<223> OTHER INFORMATION: n is a, c, g, or t
```

```
<220> FEATURE:
<221> NAME/KEY: misc_feature
<222> LOCATION: (10865)..(10867)
<223> OTHER INFORMATION: n is a, c, g, or t
<220> FEATURE:
<221> NAME/KEY: misc_feature
<222> LOCATION: (10882)..(10884)
<223> OTHER INFORMATION: n is a, c, g, or t
<220> FEATURE:
<221> NAME/KEY: misc_feature
<222> LOCATION: (11867)..(11869)
<223> OTHER INFORMATION: n is a, c, g, or t
<220> FEATURE:
<221> NAME/KEY: misc_feature
<222> LOCATION: (11884)..(11886)
<223> OTHER INFORMATION: n is a, c, g, or t
<220> FEATURE:
<221> NAME/KEY: misc_feature
<222> LOCATION: (13187)..(13192)
<223> OTHER INFORMATION: n is a, c, g, or t
<220> FEATURE:
<221> NAME/KEY: misc_feature
<222> LOCATION: (14730)..(14736)
<223> OTHER INFORMATION: n is a, c, g, or t

<400> SEQUENCE: 2
nnnttaatta annntccctt ccagctctct gcccctttg gattgaagcc aatatgataa      60 tgaggggtg gagtttgtga cgtggcgcgg ggcgtgggaa cggggcgggt gacgtagtag     120
tgtggcggaa gtgtgatgtt gcaagtgtgg cggaacacat gtaagcgacg gatgtggcaa    180
aagtgacgtt tttggtgtgc gccggtgtac acaggaagtg acaattttcg cgcggtttta    240
ggcggatgtt gtagtaaatt tgggcgtaac cgagtaagat ttggccattt tcgcgggaaa    300
actgaataag aggaagtgaa atctgaataa ttttgtgtta ctcatagcgc gtaannnggt    360
accgcggcct aatagtaatc aattacgggg tcattagttc atagcccata tatggagttc    420
cgcgttacat aacttacggt aaatggcccg cctggctgac cgcccaacga cccccgccca    480
ttgacgtcaa tgggagtttg ttttggcacc aaaatcaacg ggactttcca aaatgtcgta    540
acaactccgc cccattgacg caaatgggcg gtaggcgtgt acggtgggag gtctatataa    600
gcagagctgg tttagtgaac cgtcagatcg ctagcgcta ccggactcag atctcgagct     660
caagcttcga attctgcagt cgacggtacc gcgggcccgg gatccaccgg tcgccaccat    720
ggtgagcaag ggcgaggagc tgttcaccgg ggtggtgccc atcctggtcg agctggacgg    780
cgacgtaaac ggccacaagt tcagcgtgtc cggcgagggc gagggcgatg ccacctacgg    840
caagctgacc ctgaagttca tctgcaccac cggcaagctg cccgtgccct ggcccaccct    900
cgtgaccacc ctgacctacg gcgtgcagtg cttcagccgc taccccgacc acatgaagca    960
gcacgacttc ttcaagtccg ccatgcccga aggctacgtc caggagcgca ccatcttctt   1020
caaggacgac ggcaactaca agacccgcgc cgaggtgaag ttcgagggcg acaccctggt   1080
gaaccgcatc gagctgaagg gcatcgactt caaggaggac ggcaacatcc tggggcacaa   1140
gctggagtac aactacaaca gccacaacgt ctatatcatg gccgacaagc agaagaacgg   1200
catcaaggtg aacttcaaga tccgccacaa catcgaggac ggcagcgtgc agctcgccga   1260
ccactaccag cagaacaccc ccatcggcga cggccccgtg ctgctgcccg acaaccacta   1320
cctgagcacc cagtccgccc tgagcaaaga ccccaacgaa agcgcgatc acatggtcct    1380 gctggagttc gtgaccgccg ccgggatcac tctcggcatg gacgagctgt acaagtaaag   1440
cggccgcgac tctagatcat aatcagccat accacatttg tagaggtttt acttgcttta   1500
aaaaacctcc cacacctccc cctgaacctg aaacataaaa tgaatgcaat tgttgttgtt   1560
```

```
aacttgttta ttgcagctta taatggttac aaataaagca atagcatcac aaatttcaca   1620
aataaagcat ttttttcact gcattctagt tgtggtttgt ccaaactcat caatgtatct   1680
taaggccgcc tcgagtctag aagtaatcaa ttacggggtc attagttcat agcccatata   1740
tggagttccg cgttacataa cttacggtaa atggcccgcc tggctgaccg cccaacgacc   1800
cccgcccatt gacgtcaatg ggagtttgtt ttggcaccaa aatcaacggg actttccaaa   1860
atgtcgtaac aactccgccc cattgacgca aatgggcggt aggcgtgtac ggtgggaggt   1920
ctatataagc agagctggtt tagtgaaccg tcagatccgc tagcatgccc ctcaacgtta   1980
gcttcaccaa caggaactat gacctcgact acgactcggt gcagccgtat ttctactgcg   2040
acgaggagga gaacttctac cagcagcagc agcagagcga gctgcagccc ccggcgccca   2100
gcgaggatat ctggaagaaa ttcgagctgc tgcccacccc gccccctgcc cctagccgcc   2160
gctccgggct ctgctcgccc tcctacgttg cggtcacacc cttctcccct cggggagaca   2220
acgacggcgg tggcgggagc ttctccacgg ccgaccagct ggagatggtg accgagctgc   2280
tgggaggaga catggtgaac cagagtttca tctgcgaccc ggacgacgag accttcatca   2340
aaaacatcat catccaggac tgtatgtgga gcggcttctc ggccgccgcc aagctcgtct   2400
cagagaagct ggcctcctac caggctgcgc gcaaagacag cggcagcccg aaccccgccc   2460
gcggccacag cgtctgctcc acctccagct tgtacctgca ggatctgagc gccgccgcct   2520
cagagtgcat cgaccctcg gtggtcttcc cctaccctct caacgacagc agctcgccca   2580
agtcctgcgc ctcgcaagac tccagcgcct tctctccgtc ctcggattct ctgctctcct   2640
cgacggagtc ctccccgcag ggcagccccg agccctggt gctccatgag gagacaccgc   2700
ccaccaccag cagcgactct gaggaggaac aagaagatga ggaagaaatc gatgttgttt   2760
ctgtggaaaa gaggcaggct cctggcaaaa ggtcagagtc tggatcacct tctgctggag   2820
gccacagcaa acctcctcac agcccactgg tcctcaagag gtgccacgtc tccacacatc   2880
agcacaacta cgcagcgcct ccctccactc ggaaggacta tcctgctgcc aagagggtca   2940
agttggacag tgtcagagtc ctgagacaga tcagcaacaa ccgaaaatgc accagcccca   3000
ggtcctcgga caccgaggag aatgtcaaga ggcgaacaca caacgtcttg gagcgccaga   3060
ggaggaacga gctaaaacgg agcttttttg ccctgcgtga ccagatcccg gagttggaaa   3120
acaatgaaaa ggcccccaag gtagttatcc ttaaaaaagc cacagcatac atcctgtccg   3180
tccaagcaga ggagcaaaag ctcatttctg aagaggactt gttgcggaaa cgacgagaac   3240
agttgaaaca caaacttgaa cagctacgga actcttgtgc gtaagctagc gctaccggac   3300
tcagatcggc cgcgactcta gatcataatc agccatacca catttgtaga ggttttactt   3360
gctttaaaaa acctcccaca cctccccctg aacctgaaac ataaaatgaa tgcaattgtt   3420
gttgttaact tgtttattgc agcttataat ggttacaaat aaagcaatag catcacaaat   3480
ttcacaaata aagcattttt ttcactgcat tctagttgtg gtttgtccaa actcatcaat   3540
gtattctaga gataattcag taatcaatta cggggtcatt agttcatagc ccatatatgg   3600
agttccgcgt tacataactt acggtaaatg gcccgcctgg ctgaccgccc aacgaccccc   3660
gcccattgac gtcaatggga gtttgttttg gcaccaaaat caacgggact ttccaaaatg   3720
tcgtaacaac tccgccccat tgacgcaaat gggcggtagg cgtgtacggt gggaggtcta   3780
tataagcaga gctggtttag tgaaccgtca gatccgctag catggctgtc agcgacgcgc   3840
tgctcccatc tttctccacg ttcgcgtctg gcccggcggg aagggagaag acactgcgtc   3900
aagcaggtgc cccgaataac cgctggcggg aggagctctc ccacatgaag cgacttcccc   3960
```

```
cagtgcttcc cggccgcccc tatgacctgg cggcggcgac cgtggccaca gacctggaga   4020
gcggcggagc cggtgcggct tgcggcggta gcaacctggc gcccctacct cggagagaga   4080

ccgaggagtt caacgatctc ctggacctgg actttattct ctccaattcg ctgacccatc   4140
ctccggagtc agtggccgcc accgtgtcct cgtcagcgtc agcctcctct tcgtcgtcgc   4200
cgtcgagcag cggccctgcc agcgcgccct ccacctgcag cttcacctat ccgatccggg   4260
ccgggaacga cccgggcgtg gcgccgggcg gcacgggcgg aggcctcctc tatggcaggg   4320
agtccgctcc ccctccgacg gctcccttca acctggcgga catcaacgac gtgagcccct   4380
cgggcggctt catggccgag ctcctgcggc cagaattgga cccggtgtac attccgccgc   4440
agcagccgca gccgccaggt ggcgggctga tgggcaagtt cgtgctgaag gcgtcgctga   4500
gcgcccctgg cagcgagtac ggcagcccgt cggtcatcag cgtcagcaaa ggcagccctg   4560
acggcagcca cccggtggtg gtggcgccct acaacggcgg gccgccgcgc acgtgcccca   4620
agatcaagca ggaggcggtc tcttcgtgca cccacttggg cgctggaccc cctctcagca   4680
atggccaccg gccggctgca cacgacttcc ccctggggcg gcagctcccc agcaggacta   4740
ccccgaccct gggtcttgag gaagtgctga gcagcaggga ctgtcaccct gccctgccgc   4800
ttcctcccgg cttccatccc cacccggggc ccaattaccc atccttcctg cccgatcaga   4860
tgcagccgca agtcccgccg ctccattacc aagagctcat gccacccggt tcctgcatgc   4920
cagaggagcc caagccaaag aggggaagac gatcgtggcc ccggaaaagg accgccaccc   4980
acacttgtga ttacgcgggc tgcggcaaaa cctacacaaa gagttcccat ctcaaggcac   5040
acctgcgaac ccacacaggt gagaaacctt accactgtga ctgggacggc tgtggatgga   5100
aattcgcccg ctcagatgaa ctgaccaggc actaccgtaa acacacgggg caccgcccgt   5160
tccagtgcca aaaatgcgac cgagcatttt ccaggtcgga ccacctcgcc ttacacatga   5220
agaggcattt ttaagctagc gctaccggac tcagatcggc cgcgactcta gatcataatc   5280
agccatacca catttgtaga ggttttactt gctttaaaaa acctcccaca cctccccctg   5340
aacctgaaac ataaaatgaa tgcaattgtt gttgttaact tgtttattgc agcttataat   5400
ggttacaaat aaagcaatag catcacaaat ttcacaaata aagcattttt ttcactgcat   5460
tctagttgtg gtttgtccaa actcatcaat gtatgaatta tcgaattcaa gcttagtaat   5520
caattacggg gtcattagtt catagcccat atatggagtt ccgcgttaca taacttacgg   5580
taaatggccc gcctggctga ccgcccaacg acccccgccc attgacgtca atgggagttt   5640
gttttggcac caaaatcaac gggactttcc aaaatgtcgt aacaactccg ccccattgac   5700
gcaaatgggc ggtaggcgtg tacggtggga ggtctatata agcagagctg gtttagtgaa   5760
ccgtcagatc cgctagcatg tacaacatga tggagacgga gctgaagccg ccgggcccgc   5820
agcaaacttc ggggggcggc ggcggcaact ccaccgcggc ggcggccggc ggcaaccaga   5880
aaaacagccc ggaccgcgtc aagcggccca tgaatgcctt catggtgtgg tcccgcgggc   5940
agcggcgcaa gatggcccag gagaacccca agatgcacaa ctcggagatc agcaagcgcc   6000
tgggcgccga gtggaaactt ttgtcggaga cggagaagcg gccgttcatc gacgaggcta   6060
agcggctgcg agcgctgcac atgaaggagc acccggatta taaataccgg ccccggcgga   6120
aaaccaagac gctcatgaag aaggataagt acacgctgcc cggcgggctg ctggcccccg   6180
gcggcaatag catggcgagc ggggtcgggg tgggcgccgg cctgggcgcg ggcgtgaacc   6240
agcgcatgga cagttacgcg cacatgaacg gctggagcaa cggcagctac agcatgatgc   6300
```

```
aggaccagct gggctacccg cagcacccgg gcctcaatgc gcacggcgca gcgcagatgc    6360
agcccatgca ccgctacgac gtgagcgccc tgcagtacaa ctccatgacc agctcgcaga    6420
cctacatgaa cggctcgccc acctacagca tgtcctactc gcagcagggc acccctggca    6480
tggctcttgg ctccatgggt tcggtggtca agtccgaggc cagctccagc ccccctgtgg    6540
ttacctcttc ctcccactcc agggcgccct gccaggccgg ggacctccgg acatgatca    6600 gcatgtatct ccccggcgcc gaggtgccgg aacccgccgc ccccagcaga cttcacatgt    6660
cccagcacta ccagagcggc ccggtgcccg gcacggccat taacggcaca ctgcccctct    6720
cacacatgtg agctagcgct accggactca gatcggccgc gactctagat cataatcagc    6780
cataccacat ttgtagaggt tttacttgct ttaaaaaacc tcccacacct ccccctgaac    6840
ctgaaacata aaatgaatgc aattgttgtt gttaacttgt ttattgcagc ttataatggt    6900
tacaaataaa gcaatagcat cacaaatttc acaaataaag catttttttc actgcattct    6960
agttgtggtt tgtccaaact catcaatgta taagcttgtc gacagtaatc aattacgggg    7020
tcattagttc atagcccata tatggagttc cgcgttacat aacttacggt aaatggcccg    7080
cctggctgac cgcccaacga ccccgccca ttgacgtcaa tgggagtttg ttttggcacc    7140
aaaatcaacg ggactttcca aatgtcgta acaactccgc cccattgacg caaatgggcg    7200
gtaggcgtgt acggtgggag gtctatataa gcagagctgg tttagtgaac cgtcagatcc    7260
gctagcatgg cgggacacct ggcttcggat ttcgccttct cgcccctcc aggtggtgga    7320 ggtgatgggc caggggggcc ggagccgggc tgggttgatc ctcggacctg gctaagcttc    7380
caaggccctc ctgagggcc aggaatcggg ccggggttg gccaggctc tgaggtgtgg    7440 gggattcccc catgcccccc gccgtatgag ttctgtgggg ggatggcgta ctgtgggccc    7500
caggttggag tggggctagt gccccaaggc ggcttggaga cctctcagcc tgagggtgaa    7560
gcangagtcg gggtggagag caactccgat ggggcctccc cggagccctg caccgtcacc    7620
cctggtgccg tgaagctgga gaaggagaag ctggagcaaa acccggagga gtcccaggac    7680
atcaaagctc tgcagaaaga actcgagcaa tttgccaagc tcctgaagca gaagaggatc    7740
accctgggat atacacaggc cgatgtgggg ctcaccctgg gggttctatt tgggaaggta    7800
ttcagccaaa cgaccatctg ccgctttgag gctctgcagc ttagcttcaa gaacatgtgt    7860
aagctgcggc ccttgctgca gaagtgggtg gaggaagctg acaacaatga aaatcttcag    7920
gagatatgca aagcagaaac cctcgtgcag gcccgaaaga gaaagcgaac cagtatcgag    7980
aaccgagtga gaggcaacct ggagaatttg ttcctgcagt gcccgaaacc cacactgcag    8040
cagatcagcc acatcgccca gcagcttggg ctcgagaagg atgtggtccg agtgtggttc    8100
tgtaaccggc gccagaaggg caagcgatca agcagcgact atgcacaacg agaggatttt    8160
gaggctgctg ggtctccttt ctcaggggga ccagtgtcct ttcctctggc cccagggccc    8220
cattttggta ccccaggcta tgggagccct cacttcactg cactgtactc ctcggtccct    8280
ttccctgagg gggaagcctt tccccctgtc tccgtcacca ctctgggctc tcccatgcat    8340
tcaaactgag ctagcgctac cggactcaga tcggccgcga ctctagatca taatcagcca    8400
taccacattt gtagaggttt tacttgcttt aaaaaacctc ccacacctcc cctgaacct    8460 gaaacataaa atgaatgcaa ttgttgttgt taacttgttt attgcagctt ataatggtta    8520
caaataaagc aatagcatca caaatttcac aaataaagca ttttttttcac tgcattctag    8580 ttgtggtttg tccaaactca tcaatgtatg tcgacagatc tnnntaaggg tgggaaagaa    8640
tatataaggt gggggtctta tgtagttttg tatctgtttt gcagcagccg ccgccgccat    8700
```

```
gagcaccaac tcgtttgatg gaagcattgt gagctcatat ttgacaacgc gcatgccccc    8760
atgggccggg gtgcgtcaga atgtgatggg ctccagcatt gatggtcgcc ccgtcctgcc    8820
cgcaaactct actaccttga cctacgagac cgtgtctgga acgccgttgg agactgcagc    8880
ctccgccgcc gcttcagccg ctgcagccac cgcccgcggg attgtgactg actttgcttt    8940
cctgagcccg cttgcaagca gtgcagcttc ccgttcatcc gcccgcgatg acaagttgac    9000
ggctcttttg gcacaattgg attctttgac ccgggaactt aatgtcgttt ctcagcagct    9060
gttggatctg cgccagcagg tttctgccct gaaggcttcc tcccctccca atgcggttta    9120
aaacataaat aaaaaaccag actctgtttg gatttggatc aagcaagtgt cttgctgtct    9180
ttatttaggg gttttgcgcg cgcggtaggc ccgggaccag cggtctcggt cgttgagggt    9240
cctgtgtatt ttttccagga cgtggtaaag gtgactctgg atgttcagat acatgggcat    9300
aagcccgtct ctggggtgga ggtagcacca ctgcagagct tcatgctgcg gggtggtgtt    9360
gtagatgatc cagtcgtagc aggagcgctg ggcgtggtgc ctaaaaatgt ctttcagtag    9420
caagctgatt gccaggggca ggcccttggt gtaagtgttt acaaagcggt taagctggga    9480
tgggtgcata cgtggggata tgagatgcat cttggactgt attttttaggt tggctatgtt    9540
cccagccata tccctccggg gattcatgtt gtgcagaacc accagcacag tgtatccggt    9600
gcacttggga aatttgtcat gtagcttaga aggaaatgcg tggaagaact tggagacgcc    9660
cttgtgacct ccaagatttt ccatgcattc gtccataatg atggcaatgg gcccacgggc    9720
ggcggcctgg gcgaagatat ttctgggatc actaacgtca tagttgtgtt ccaggatgag    9780
atcgtcatag gccatttta caaagcgcgg gcggagggtg ccagactgcg gtataatggt    9840
tccatccggc ccaggggcgt agttaccctc acagatttgc atttcccacg ctttgagttc    9900
agatggggg atcatgtcta cctgcggggc gatgaagaaa acggtttccg gggtagggga    9960
gatcagctgg gaagaaagca ggttcctgag cagctgcgac ttaccgcagc cggtgggccc    10020
gtaaatcaca cctattaccg ggtgcaactg gtagttaaga gagctgcagc tgccgtcatc    10080
cctgagcagg ggggccactt cgttaagcat gtccctgact cgcatgtttt ccctgaccaa    10140
atccgccaga aggcgctcgc cgcccagcga tagcagttct tgcaaggaag caaagttttt    10200
caacggtttg agaccgtccg ccgtaggcat gcttttgagc gtttgaccaa gcagttccag    10260
gcggtcccac agctcggtca cctgctctac ggcatctcga tccagcatat ctcctcgttt    10320
cgcgggttgg ggcggctttc gctgtacggc agtagtcggt gctcgtccag acgggccagg    10380
gtcatgtctt tccacgggcg cagggtcctc gtcagcgtag tctgggtcac ggtgaagggg    10440
tgcgctccgg gctgcgcgct ggccagggtg cgcttgaggc tggtcctgct ggtgctgaag    10500
cgctgccggt cttcgccctg cgcgtcggcc aggtagcatt tgaccatggt gtcatagtcc    10560
agcccctccg cggcgtggcc cttggcgcgc agcttgccct tggaggaggc gccgcacgag    10620
gggcagtgca gacttttgag ggcgtagagc ttgggcgcga gaaataccga ttccggggag    10680
taggcatccg cgccgcaggc cccgcagacg gtctcgcatt ccacgagcca ggtgagctct    10740
ggccgttcgg ggtcaaaaac caggtttccc ccatgctttt tgatgcgttt cttacctctg    10800
gtttccatga gccggtgtcc acgctcggtg acgaaaaggc tgtccgtgtc cccgtataca    10860
gactnnngtt taaacgaatt cnnntataaa atgcaaggtg ctgctcaaaa aatcaggcaa    10920
agcctcgcgc aaaaagaaa gcacatcgta gtcatgctca tgcagataaa ggcaggtaag    10980
ctccggaacc accacagaaa aagacaccat ttttctctca aacatgtctg cgggtttctg    11040
```

```
cataaacaca aaataaaata acaaaaaaac atttaaacat tagaagcctg tcttacaaca   11100
ggaaaaacaa cccttataag cataagacgg actacggcca tgccggcgtg accgtaaaaa   11160
aactggtcac cgtgattaaa aagcaccacc gacagctcct cggtcatgtc cggagtcata   11220
atgtaagact cggtaaacac atcaggttga ttcatcggtc agtgctaaaa agcgaccgaa   11280
atagcccggg ggaatacata cccgcaggcg tagagacaac attacagccc ccataggagg   11340
tataacaaaa ttaataggag agaaaaacac ataaacacct gaaaaaccct cctgcctagg   11400
caaaatagca ccctcccgct ccagaacaac atacagcgct tcacagcggc agcctaacag   11460
tcagccttac cagtaaaaaa gaaaacctat taaaaaaaca ccactcgaca cggcaccagc   11520
tcaatcagtc acagtgtaaa aaagggccaa gtgcagagcg agtatatata ggactaaaaa   11580
atgacgtaac ggttaaagtc cacaaaaaac acccagaaaa ccgcacgcga acctacgccc   11640
agaaacgaaa gccaaaaaac ccacaacttc ctcaaatcgt cacttccgtt ttcccacgtt   11700
acgtaacttc ccattttaag aaaactacaa ttcccaacac atacaagtta ctccgcccta   11760
aaacctacgt cacccgcccc gttcccacgc cccgcgccac gtcacaaact ccacccctc   11820
attatcatat tggcttcaat ccaaaataag gtatattatt gatgatnnnt taattaagga   11880
tccnnncggt gtgaaatacc gcacagatgc gtaaggagaa aataccgcat caggcgctct   11940
tccgcttcct cgctcactga ctcgctgcgc tcggtcgttc ggctgcggcg agcggtatca   12000
gctcactcaa aggcggtaat acggttatcc acagaatcag gggataacgc aggaaagaac   12060
atgtgagcaa aaggccagca aaaggccagg aaccgtaaaa aggccgcgtt gctggcgttt   12120
ttccataggc tccgccccc tgacgagcat cacaaaaatc gacgctcaag tcagaggtgg   12180
cgaaacccga caggactata aagataccag gcgtttcccc ctggaagctc cctcgtgcgc   12240
tctcctgttc cgaccctgcc gcttaccgga tacctgtccg cctttctccc ttcgggaagc   12300
gtggcgcttt ctcatagctc acgctgtagg tatctcagtt cggtgtaggt cgttcgctcc   12360
aagctgggct gtgtgcacga accccccgtt cagcccgacc gctgcgcctt atccggtaac   12420
tatcgtcttg agtccaaccc ggtaagacac gacttatcgc cactggcagc agccactggt   12480
aacaggatta gcagagcgag gtatgtaggc ggtgctacag agttcttgaa gtggtggcct   12540
aactacggct acactagaag gacagtattt ggtatctgcg ctctgctgaa gccagttacc   12600
ttcggaaaaa gagttggtag ctcttgatcc ggcaaacaaa ccaccgctgg tagcggtggt   12660
ttttttgttt gcaagcagca gattacgcgc agaaaaaaag gatctcaaga agatcctttg   12720
atcttttcta cggggtctga cgctcagtgg aacgaaaact cacgttaagg gattttggtc   12780
atgagattat caaaaaggat cttcacctag atccttttaa attaaaaatg aagttttaaa   12840
tcaatctaaa gtatatatga gtaaacttgg tctgacagtt accaatgctt aatcagtgag   12900
gcacctatct cagcgatctg tctatttcgt tcatccatag ttgcctgact ccccgtcgtg   12960
tagataacta cgatacggga gggcttacca tctggcccca gtgctgcaat gataccgcga   13020
gacccacgct caccggctcc agatttatca gcaataaacc agccagccgg aagggccgag   13080
cgcagaagtg gtcctgcaac tttatccgcc tccatccagt ctattaattg ttgccgggaa   13140
gctagagtaa gtagttcgcc agttaatagt ttgcgcaacg ttgttgnnnn nnaaaaagga   13200
tcttcaccta gatcctttc acgtagaaag ccagtccgca gaaacggtgc tgaccccgga   13260
tgaatgtcag ctactgggct atctggacaa gggaaaacgc aagcgcaaag agaaagcagg   13320
tagcttgcag tgggcttaca tggcgatagc tagactgggc ggttttatgg acagcaagcg   13380
aaccggaatt gccagctggg gcgccctctg gtaaggttgg gaagccctgc aaagtaaact   13440
```

```
ggatggcttt ctcgccgcca aggatctgat ggcgcagggg atcaagctct gatcaagaga    13500
caggatgagg atcgtttcgc atgattgaac aagatggatt gcacgcaggt tctccggccg    13560
cttgggtgga gaggctattc ggctatgact gggcacaaca gacaatcggc tgctctgatg    13620
ccgccgtgtt ccgctgtca gcgcaggggc gcccggttct ttttgtcaag accgacctgt    13680
ccggtgccct gaatgaactg caagacgagg cagcgcggct atcgtggctg gccacgacgg    13740
gcgttccttg cgcagctgtg ctcgacgttg tcactgaagc gggaagggac tggctgctat    13800
tgggcgaagt gccggggcag gatctcctgt catctcacct tgctcctgcc gagaaagtat    13860
ccatcatggc tgatgcaatg cggcggctgc atacgcttga tccggctacc tgcccattcg    13920
accaccaagc gaaacatcgc atcgagcgag cacgtactcg gatggaagcc ggtcttgtcg    13980
atcaggatga tctggacgaa gagcatcagg ggctcgcgcc agccgaactg ttcgccaggc    14040
tcaaggcgag catgcccgac ggcgaggatc tcgtcgtgac ccatggcgat gcctgcttgc    14100
cgaatatcat ggtggaaaat ggccgctttt ctggattcat cgactgtggc cggctgggtg    14160
tggcggaccg ctatcaggac atagcgttgg ctacccgtga tattgctgaa gagcttggcg    14220
gcgaatgggc tgaccgcttc ctcgtgcttt acggtatcgc cgctcccgat tcgcagcgca    14280
tcgccttcta tcgccttctt gacgagttct tctgaatttt gttaaaattt tgttaaatc     14340 agctcatttt ttaaccaata ggccgaaatc ggcaacatcc cttataaatc aaaagaatag    14400
accgcgatag ggttgagtgt tgttccagtt tggaacaaga gtccactatt aaagaacgtg    14460
gactccaacg tcaagggcg aaaaaccgtc tatcagggcg atggcccact acgtgaacca     14520
tcacccaaat caagttttttt gcggtcgagg tgccgtaaag ctctaaatcg aaccctaaa    14580 gggagccccc gatttagagc ttgacgggga agccggcga acgtggcgag aaaggaaggg    14640
aagaaagcga aggagcggg cgctagggcg ctggcaagtg tagcggtcac gctgcgcgta    14700
accaccacac ccgcgcgctt aatgcgccgn nnnnnn                              14736
```

<210> SEQ ID NO 3
<211> LENGTH: 13418
<212> TYPE: DNA
<213> ORGANISM: Artificial Sequence
<220> FEATURE:
<223> OTHER INFORMATION: The adeno shuttle vector containing multi-RFs
      under CMV weak promoter (CMVWP) has been provided as
      pAd(CMVWP)-cMKSO (cM; c-Myc, K; KLF4, S; SOX2, O; OCT3/4).
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (12)..(14)
<223> OTHER INFORMATION: n is a, c, g, or t
<220> FEATURE:
<221> NAME/KEY: misc_feature
<222> LOCATION: (355)..(357)
<223> OTHER INFORMATION: n is a, c, g, or t
<220> FEATURE:
<221> NAME/KEY: misc_feature
<222> LOCATION: (6246)..(6246)
<223> OTHER INFORMATION: n is a, c, g, or t
<220> FEATURE:
<221> NAME/KEY: misc_feature
<222> LOCATION: (7304)..(7306)
<223> OTHER INFORMATION: n is a, c, g, or t
<220> FEATURE:
<221> NAME/KEY: misc_feature
<222> LOCATION: (9547)..(9549)
<223> OTHER INFORMATION: n is a, c, g, or t
<220> FEATURE:

```
<221> NAME/KEY: misc_feature
<222> LOCATION: (9564)..(9566)
<223> OTHER INFORMATION: n is a, c, g, or t
<220> FEATURE:
<221> NAME/KEY: misc_feature
<222> LOCATION: (10549)..(10551)
<223> OTHER INFORMATION: n is a, c, g, or t
<220> FEATURE:
<221> NAME/KEY: misc_feature
<222> LOCATION: (10566)..(10568)
<223> OTHER INFORMATION: n is a, c, g, or t
<220> FEATURE:
<221> NAME/KEY: misc_feature
<222> LOCATION: (11869)..(11874)
<223> OTHER INFORMATION: n is a, c, g, or t
<220> FEATURE:
<221> NAME/KEY: misc_feature
<222> LOCATION: (13412)..(13418)
<223> OTHER INFORMATION: n is a, c, g, or t

<400> SEQUENCE: 3
nnnttaatta annntcccatt ccagctctct gccccttttg gattgaagcc aatatgataa      60 tgaggggtg gagtttgtga cgtggcgcgg ggcgtgggaa cggggcgggt gacgtagtag       120
tgtggcggaa gtgtgatgtt gcaagtgtgg cggaacacat gtaagcgacg gatgtggcaa     180
aagtgacgtt tttggtgtgc gccggtgtac acaggaagtg acaattttcg cgcggtttta     240
ggcggatgtt gtagtaaatt tgggcgtaac cgagtaagat ttggccattt tcgcgggaaa    300
actgaataag aggaagtgaa atctgaataa ttttgtgtta ctcatagcgc gtaannnggt    360
accgcggccg cctcgagtct agaagtaatc aattacgggg tcattagttc atagcccata   420 tatgagttc cgcgttacat aacttacggt aaatggcccg cctggctgac cgcccaacga   480
cccccgccca ttgacgtcaa tgggagtttg ttttggcacc aaaatcaacg ggactttcca   540
aaatgtcgta acaactccgc cccattgacg caaatgggcg gtaggcgtgt acggtgggag   600
gtctatataa gcagagctgg tttagtgaac cgtcagatcc gctagcatgc cctcaacgt    660 tagcttcacc aacaggaact atgacctcga ctacgactcg gtgcagccgt atttctactg    720
cgacgaggag gagaacttct accagcagca gcagcagagc gagctgcagc cccggcgcc    780 cagcgaggat atctggaaga aattcgagct gctgcccacc ccgccctgt cccctagccg    840 ccgctccggg ctctgctcgc cctcctacgt tgcggtcaca cccttctccc ttcggggaga    900
caacgacggc ggtggcggga gcttctccac ggccgaccag ctggagatgg tgaccgagct    960
gctgggagga gacatggtga accagagttt catctgcgac ccggacgacg agaccttcat   1020
caaaaacatc atcatccagg actgtatgtg gagcggcttc tcggccgccg ccaagctcgt   1080
ctcagagaag ctggcctcct accaggctgc gcgcaaagac agcggcagcc cgaacccgc    1140 ccgcggccac agcgtctgct ccacctccag cttgtacctg caggatctga gcgccgccgc    1200
ctcagagtgc atcgacccct cggtggtctt ccctaccct ctcaacgaca gcagctcgcc    1260
caagtcctgc gcctcgcaag actccagcgc cttctctccg tcctcggatt ctctgctctc    1320
ctcgacggag tcctccccgc agggcagccc cgagccctg gtgctccatg aggagacacc    1380
gcccaccacc agcagcgact ctgaggagga acaagaagat gaggaagaaa tcgatgttgt   1440
ttctgtggaa aagaggcagg ctcctggcaa aggtcagag tctggatcac cttctgctgg    1500
aggccacagc aaacctcctc acagcccact ggtcctcaag aggtgccacg tctccacaca    1560
tcagcacaac tacgcagcgc ctccctccac tcggaaggac tatcctgctg ccaagagggt    1620
caagttggac agtgtcagag tcctgagaca gatcagcaac aaccgaaaat gcaccagccc    1680
caggtcctcg gacaccgagg agaatgtcaa gaggcgaaca cacaacgtct ggagcgcca    1740
```

```
gaggaggaac gagctaaaac ggagcttttt tgccctgcgt gaccagatcc cggagttgga    1800
aaacaatgaa aaggccccca aggtagttat ccttaaaaaa gccacagcat acatcctgtc    1860
cgtccaagca gaggagcaaa agctcatttc tgaagaggac ttgttgcgga aacgacgaga    1920
acagttgaaa cacaaacttg aacagctacg gaactcttgt gcgtaagcta gcgctaccgg    1980
actcagatcg gccgcgactc tagatcataa tcagccatac cacatttgta gaggttttac    2040
ttgctttaaa aaacctccca cacctccccc tgaacctgaa acataaaatg aatgcaattg    2100
ttgttgttaa cttgtttatt gcagcttata atggttacaa ataaagcaat agcatcacaa    2160
atttcacaaa taaagcattt ttttcactgc attctagttg tggtttgtcc aaactcatca    2220
atgtattcta gagataattc agtaatcaat tacggggtca ttagttcata gcccatatat    2280
ggagttccgc gttacataac ttacggtaaa tggcccgcct ggctgaccgc ccaacgaccc    2340
ccgcccattg acgtcaatgg gagtttgttt tggcaccaaa atcaacggga ctttccaaaa    2400
tgtcgtaaca actccgcccc attgacgcaa atgggcggta ggcgtgtacg gtgggaggtc    2460
tatataagca gagctggttt agtgaaccgt cagatccgct agcatggctg tcagcgacgc    2520
gctgctccca tctttctcca cgttcgcgtc tggcccggcg ggaagggaga agacactgcg    2580
tcaagcaggt gccccgaata accgctggcg ggaggagctc tcccacatga agcgacttcc    2640
cccagtgctt cccggccgcc cctatgacct ggcggcggcg accgtggcca cagacctgga    2700
gagcggcgga gccggtgcgg cttgcggcgg tagcaacctg gcgcccctac ctcggagaga    2760
gaccgaggag ttcaacgatc tcctggacct ggactttatt ctctccaatt cgctgaccca    2820
tcctccggag tcagtggccg ccaccgtgtc ctcgtcagcg tcagcctcct cttcgtcgtc    2880
gccgtcgagc agcggccctg ccagcgcgcc ctccacctgc agcttcacct atccgatccg    2940
ggccgggaac gacccgggcg tggcgccggg cggcacgggc ggaggcctcc tctatggcag    3000
ggagtccgct cccctccga cggctcccct caacctggcg gacatcaacg acgtgagccc    3060
ctcgggcggc ttcatggccg agctcctgcg gccagaattg gacccggtgt acattccgcc    3120
gcagcagccg cagccgccag gtggcgggct gatgggcaag ttcgtgctga aggcgtcgct    3180
gagcgcccct ggcagcgagt acggcagccc gtcggtcatc agcgtcagca aaggcagccc    3240
tgacggcagc caccccggtgg tggtggcgcc ctacaacggc gggccgccgc gcacgtgccc    3300
caagatcaag caggaggcgg tctcttcgtg cacccacttg ggcgctggac cccctctcag    3360
caatggccac cggccggctg cacacgactt cccctggggg cggcagctcc ccagcaggac    3420
taccccgacc ctgggtcttg aggaagtgct gagcagcagg gactgtcacc ctgccctgcc    3480
gcttcctccc ggcttccatc cccacccggg gcccaattac ccatccttcc tgcccgatca    3540
gatgcagccg caagtcccgc cgctccatta ccaagagctc atgccacccg gttcctgcat    3600
gccagaggag cccaagccaa agaggggaag acgatcgtgg ccccggaaaa ggaccgccac    3660
ccacacttgt gattacgcgg gctgcggcaa aacctacaca aagagttccc atctcaaggc    3720
acacctgcga acccacacag gtgagaaacc ttaccactgt gactgggacg gctgtggatg    3780
gaaattcgcc cgctcagatg aactgaccag gcactaccgt aaacacacgg ggcaccgccc    3840
gttccagtgc caaaaatgcg accgagcatt ttccaggtcg gaccacctcg ccttacacat    3900
gaagaggcat ttttaagcta gcgctaccgg actcagatcg gccgcgactc tagatcataa    3960
tcagccatac cacatttgta gaggttttac ttgctttaaa aaacctccca cacctccccc    4020
tgaacctgaa acataaaatg aatgcaattg ttgttgttaa cttgtttatt gcagcttata    4080
```

```
atggttacaa ataaagcaat agcatcacaa atttcacaaa taaagcattt ttttcactgc    4140
attctagttg tggtttgtcc aaactcatca atgtatgaat tatcgaattc aagcttagta    4200
atcaattacg gggtcattag ttcatagccc atatatggag ttccgcgtta cataacttac    4260
ggtaaatggc ccgcctggct gaccgcccaa cgacccccgc ccattgacgt caatgggagt    4320
ttgttttggc accaaaatca acgggacttt ccaaaatgtc gtaacaactc cgccccattg    4380
acgcaaatgg gcggtaggcg tgtacggtgg gaggtctata taagcagagc tggtttagtg    4440
aaccgtcaga tccgctagca tgtacaacat gatggagacg gagctgaagc cgccgggccc    4500
gcagcaaact cgggggggcg gcggcggcaa ctccaccgcg gcggcggccg gcggcaacca    4560
gaaaaacagc ccggaccgcg tcaagcggcc catgaatgcc ttcatggtgt ggtcccgcgg    4620
gcagcggcgc aagatggccc aggagaaccc caagatgcac aactcggaga tcagcaagcg    4680
cctgggcgcc gagtggaaac ttttgtcgga cacggagaag cggccgttca tcgacgaggc    4740
taagcggctg cgagcgctgc acatgaagga gcacccggat tataaatacc ggccccggcg    4800
gaaaaccaag acgctcatga agaaggataa gtacacgctg cccggcgggc tgctggcccc    4860
cggcggcaat agcatggcga gcggggtcgg ggtgggcgcc ggcctgggcg cgggcgtgaa    4920
ccagcgcatg gacagttacg cgcacatgaa cggctggagc aacggcagct acagcatgat    4980
gcaggaccag ctgggctacc cgcagcaccc gggcctcaat gcgcacggcg cagcgcagat    5040
gcagcccatg caccgctacg acgtgagcgc cctgcagtac aactccatga ccagctcgca    5100
gacctacatg aacggctcgc ccacctacag catgtcctac tcgcagcagg gcacccctgg    5160
catggctctt ggctccatgg gttcggtggt caagtccgag gccagctcca gcccccctgt    5220
ggttacctct tcctcccact ccagggcgcc ctgccaggcc ggggacctcc gggacatgat    5280
cagcatgtat ctccccggcg ccgaggtgcc ggaacccgcc gcccccagca gcttcacat    5340 gtcccagcac taccagagcg gcccggtgcc cggcacggcc attaacggca cactgcccct    5400
ctcacacatg tgagctagcg ctaccggact cagatcggcc gcgactctag atcataatca    5460
gccataccac atttgtagag gttttacttg ctttaaaaaa cctcccacac ctccccctga    5520
acctgaaaca taaaatgaat gcaattgttg ttgttaactt gtttattgca gcttataatg    5580
gttacaaata aagcaatagc atcacaaatt tcacaaataa agcatttttt tcactgcatt    5640
ctagttgtgg tttgtccaaa ctcatcaatg tataagcttg tcgacagtaa tcaattacgg    5700
ggtcattagt tcatagccca tatatggagt tccgcgttac ataacttacg gtaaatggcc    5760
cgcctggctg accgcccaac gacccccgcc cattgacgtc aatgggagtt gttttggca    5820 ccaaaatcaa cgggactttc caaaatgtcg taacaactcc gccccattga cgcaaatggg    5880
cggtaggcgt gtacggtggg aggtctatat aagcagagct ggtttagtga accgtcagat    5940
ccgctagcat ggcgggacac ctggcttcgg atttcgcctt ctcgcccct ccaggtggtg    6000 gaggtgatgg gccaggggg ccggagccgg gctgggttga tcctcggacc tggctaagct    6060
tccaaggccc tcctggaggg ccaggaatcg gcccggggt tgggccaggc tctgaggtgt    6120
gggggattcc cccatgcccc ccgccgtatg agttctgtgg gggatggcg tactgtgggc    6180 cccaggttgg agtggggcta gtgccccaag gcggcttgga gacctctcag cctgagggtg    6240
aagcangagt cggggtggag agcaactccg atggggcctc cccggagccc tgcaccgtca    6300
cccctggtgc cgtgaagctg gagaaggaga agctggagca aaaccgggag gagtcccagg    6360
acatcaaagc tctgcagaaa gaactcgagc aatttgccaa gctcctgaag cagaagagga    6420
tcacccctgg gatatacacag gccgatgtgg ggctcaccct gggggttcta tttgggaagg    6480
```

```
tattcagcca aacgaccatc tgccgctttg aggctctgca gcttagcttc aagaacatgt    6540
gtaagctgcg gcccttgctg cagaagtggg tggaggaagc tgacaacaat gaaaatcttc    6600
aggagatatg caaagcagaa accctcgtgc aggcccgaaa gagaaagcga accagtatcg    6660
agaaccgagt gagaggcaac ctggagaatt tgttcctgca gtgcccgaaa cccacactgc    6720
agcagatcag ccacatcgcc cagcagcttg ggctcgagaa ggatgtggtc cgagtgtggt    6780
tctgtaaccg gcgccagaag ggcaagcgat caagcagcga ctatgcacaa cgagaggatt    6840
ttgaggctgc tgggtctcct ttctcagggg gaccagtgtc ctttcctctg gccccagggc    6900
cccattttgg tacccaggc tatgggagcc ctcacttcac tgcactgtac tcctcggtcc      6960 cttccctga gggggaagcc ttccccctg tctccgtcac cactctgggc tctcccatgc      7020
attcaaactg agctagcgct accggactca gatcggccgc gactctagat cataatcagc    7080
cataccacat ttgtagaggt tttacttgct ttaaaaaacc tcccacacct cccctgaac    7140 ctgaaacata aaatgaatgc aattgttgtt gttaacttgt ttattgcagc ttataatggt    7200
tacaaataaa gcaatagcat cacaaatttc acaaataaag catttttttc actgcattct    7260
agttgtggtt tgtccaaact catcaatgta tgtcgacaga tctnnntaag ggtgggaaag    7320
aatatataag gtggggtct tatgtagttt tgtatctgtt ttgcagcagc cgccgccgcc     7380
atgagcacca actcgtttga tggaagcatt gtgagctcat atttgacaac gcgcatgccc    7440
ccatgggccg gggtgcgtca gaatgtgatg ggctccagca ttgatggtcg ccccgtcctg    7500
cccgcaaact ctactacctt gacctacgag accgtgtctg gaacgccgtt ggagactgca    7560
gcctccgccg ccgcttcagc cgctgcagcc accgcccgcg ggattgtgac tgactttgct    7620
ttcctgagcc cgcttgcaag cagtgcagct cccgttcat ccgcccgcga tgacaagttg     7680
acggctcttt tggcacaatt ggattctttg acccgggaac ttaatgtcgt ttctcagcag    7740
ctgttggatc tgcgccagca ggtttctgcc ctgaaggctt cctcccctcc caatgcggtt    7800
taaaacataa ataaaaaacc agactctgtt tggatttgga tcaagcaagt gtcttgctgt    7860
ctttatttag gggttttgcg cgcgcggtag gcccgggacc agcggtctcg gtcgttgagg    7920
gtcctgtgta tttttccag gacgtggtaa aggtgactct ggatgttcag atacatgggc      7980
ataagcccgt ctctggggtg gaggtagcac cactgcagag cttcatgctg cggggtggtg    8040
ttgtagatga tccagtcgta gcaggagcgc tgggcgtggt gcctaaaaat gtctttcagt    8100
agcaagctga ttgccagggg caggcccttg gtgtaagtgt ttacaaagcg gttaagctgg    8160
gatgggtgca tacgtgggga tatgagatgc atcttggact gtattttag gttggctatg     8220 ttcccagcca tatccctccg gggattcatg ttgtgcagaa ccaccagcac agtgtatccg    8280
gtgcacttgg gaaatttgtc atgtagctta aaggaaatg cgtggaagaa cttggagacg      8340
cccttgtgac ctccaagatt ttccatgcat tcgtccataa tgatggcaat gggcccacgg    8400
gcggcggcct gggcgaagat atttctggga tcactaacgt catagttgtg ttccaggatg    8460
agatcgtcat aggccatttt tacaaagcgc gggcggaggg tgccagactg cggtataatg    8520
gttccatccg gccagggggc gtagttaccc tcacagattt gcatttccca cgctttgagt    8580
tcagatgggg ggatcatgtc tacctgcggg gcgatgaaga aaacggtttc cggggtaggg    8640
gagatcagct gggaagaaag caggttcctg agcagctgcg acttaccgca gccggtgggc    8700
ccgtaaatca cacctattac cgggtgcaac tggtagttaa gagagctgca gctgccgtca    8760
tccctgagca gggggggccac ttcgttaagc atgtccctga ctcgcatgtt ttccctgacc    8820
```

```
aaatccgcca gaaggcgctc gccgcccagc gatagcagtt cttgcaagga agcaaagttt    8880
ttcaacggtt tgagaccgtc cgccgtaggc atgcttttga gcgtttgacc aagcagttcc    8940
aggcggtccc acagctcggt cacctgctct acggcatctc gatccagcat atctcctcgt    9000
ttcgcgggtt ggggcggctt tcgctgtacg gcagtagtcg gtgctcgtcc agacgggcca    9060
gggtcatgtc tttccacggg cgcagggtcc tcgtcagcgt agtctgggtc acggtgaagg    9120
ggtgcgctcc gggctgcgcg ctggccaggg tgcgcttgag gctggtcctg ctggtgctga    9180
agcgctgccg gtcttcgccc tgcgcgtcgg ccaggtagca tttgaccatg gtgtcatagt    9240
ccagcccctc cgcggcgtgg cccttggcgc gcagcttgcc cttggaggag cgccgcacg     9300
aggggcagtg cagacttttg agggcgtaga gcttgggcgc gagaaatacc gattccgggg    9360
agtaggcatc cgcgccgcag gccccgcaga cggtctcgca ttccacgagc caggtgagct    9420
ctggccgttc ggggtcaaaa accaggtttc ccccatgctt tttgatgcgt ttcttacctc    9480
tggtttccat gagccggtgt ccacgctcgg tgacgaaaag gctgtccgtg tccccgtata    9540
cagactnnng tttaaacgaa ttcnnntata aaatgcaagg tgctgctcaa aaaatcaggc    9600
aaagcctcgc gcaaaaaaga aagcacatcg tagtcatgct catgcagata aaggcaggta    9660
agctccggaa ccaccacaga aaaagacacc attttctctct caaacatgtc tgcgggtttc   9720
tgcataaaca caaataaaa taacaaaaaa catttaaac attagaagcc tgtcttacaa      9780
caggaaaaac aaccttata agcataagac ggactacggc catgccggcg tgaccgtaaa     9840
aaaactggtc accgtgatta aaaagcacca ccgacagctc ctcggtcatg tccggagtca    9900
taatgtaaga ctcggtaaac acatcaggtt gattcatcgg tcagtgctaa aaagcgaccg    9960
aaatagcccg ggggaataca tacccgcagg cgtagagaca acattacagc ccccatagga   10020
ggtataacaa aattataagg agagaaaaac acataaacac ctgaaaaacc ctcctgccta   10080
ggcaaaatag caccctcccg ctccagaaca acatacagcg cttcacagcg gcagcctaac   10140
agtcagcctt accagtaaaa aagaaaacct attaaaaaaa caccactcga cacggcacca   10200
gctcaatcag tcacagtgta aaaagggcc aagtgcagag cgagtatata taggactaaa    10260
aaatgacgta acggttaaag tccacaaaaa acacccagaa aaccgcacgc gaacctacgc   10320
ccagaaacga aagccaaaaa acccacaact tcctcaaatc gtcacttccg ttttcccacg   10380
ttacgtaact tcccattta agaaaactac aattcccaac acatacaagt tactccgccc    10440
taaaacctac gtcacccgcc ccgttcccac gccccgcgcc acgtcacaaa ctccaccccc   10500
tcattatcat attggcttca atccaaaata aggtatatta ttgatgatnn nttaattaag   10560
gatccnnncg gtgtgaaata ccgcacagat gcgtaaggag aaaataccgc atcaggcgct   10620
cttccgcttc ctcgctcact gactcgctgc gctcggtcgt tcggctgcgg cgagcggtat   10680
cagctcactc aaaggcggta atacggttat ccacagaatc aggggataac gcaggaaaga   10740
acatgtgagc aaaaggccag caaaaggcca ggaaccgtaa aaaggccgcg ttgctggcgt   10800
ttttccatag gctccgcccc cctgacgagc atcacaaaaa tcgacgctca agtcagaggt   10860
ggcgaaaccc gacaggacta taaagatacc aggcgtttcc ccctggaagc tccctcgtgc   10920
gctctcctgt tccgaccctg ccgcttaccg gatacctgtc cgcctttctc ccttcgggaa   10980
gcgtggcgct ttctcatagc tcacgctgta ggtatctcag ttcggtgtag gtcgttcgct   11040
ccaagctggg ctgtgtgcac gaaccccccg ttcagcccga ccgctgcgcc ttatccggta   11100
actatcgtct tgagtccaac ccggtaagac acgacttatc gccactggca gcagccactg   11160
gtaacaggat tagcagagcg aggtatgtag gcggtgctac agagttcttg aagtggtggc   11220
```

-continued

```
ctaactacgg ctacactaga aggacagtat ttggtatctg cgctctgctg aagccagtta    11280
ccttcggaaa aagagttggt agctcttgat ccggcaaaca aaccaccgct ggtagcggtg    11340 gttttttgt ttgcaagcag cagattacgc gcagaaaaaa aggatctcaa gaagatcctt     11400
tgatcttttc tacggggtct gacgctcagt ggaacgaaaa ctcacgttaa gggattttgg    11460
tcatgagatt atcaaaaagg atcttcacct agatcctttt aaattaaaaa tgaagtttta    11520
aatcaatcta agtatatat gagtaaactt ggtctgacag ttaccaatgc ttaatcagtg     11580
aggcacctat ctcagcgatc tgtctatttc gttcatccat agttgcctga ctccccgtcg    11640
tgtagataac tacgatacgg gagggcttac catctggccc cagtgctgca atgataccgc    11700
gagacccacg ctcaccggct ccagatttat cagcaataaa ccagccagcc ggaagggccg    11760
agcgcagaag tggtcctgca actttatccg cctccatcca gtctattaat tgttgccggg    11820
aagctagagt aagtagttcg ccagttaata gtttgcgcaa cgttgttgnn nnnnaaaaag   11880
gatcttcacc tagatccttt tcacgtagaa agccagtccg cagaaacggt gctgaccccg    11940
gatgaatgtc agctactggg ctatctggac aagggaaaac gcaagcgcaa agagaaagca    12000
ggtagcttgc agtgggctta catggcgata gctagactgg gcggttttat ggacagcaag    12060
cgaaccggaa ttgccagctg gggcgccctc tggtaaggtt gggaagccct gcaaagtaaa    12120
ctggatggct ttctcgccgc caaggatctg atggcgcagg ggatcaagct ctgatcaaga    12180
gacaggatga ggatcgtttc gcatgattga acaagatgga ttgcacgcag gttctccggc    12240
cgcttgggtg gagaggctat tcggctatga ctgggcacaa cagacaatcg gctgctctga    12300
tgccgccgtg ttccggctgt cagcgcaggg gcgcccggtt ctttttgtca agaccgacct    12360
gtccggtgcc ctgaatgaac tgcaagacga ggcagcgcgg ctatcgtggc tggccacgac    12420
gggcgttcct tgcgcagctg tgctcgacgt tgtcactgaa gcgggaaggg actggctgct    12480
attgggcgaa gtgccggggc aggatctcct gtcatctcac cttgctcctg ccgagaaagt    12540
atccatcatg gctgatgcaa tgcggcggct gcatacgctt gatccggcta cctgcccatt    12600
cgaccaccaa gcgaaacatc gcatcgagcg agcacgtact cggatggaag ccggtcttgt    12660
cgatcaggat gatctggacg aagagcatca ggggctcgcg ccagccgaac tgttcgccag    12720
gctcaaggcg agcatgcccg acggcgagga tctcgtcgtg acccatggcg atgcctgctt    12780
gccgaatatc atggtggaaa atggccgctt ttctggattc atcgactgtg gccggctggg    12840
tgtggcggac cgctatcagg acatagcgtt ggctacccgt gatattgctg aagagcttgg    12900
cggcgaatgg gctgaccgct tcctcgtgct ttacggtatc gccgctcccg attcgcagcg    12960
catcgccttc tatcgccttc ttgacgagtt cttctgaatt tgttaaaat ttttgttaaa    13020 tcagctcatt ttttaaccaa taggccgaaa tcggcaacat cccttataaa tcaaaagaat    13080
agaccgcgat agggttgagt gttgttccag tttggaacaa gagtccacta ttaaagaacg    13140
tggactccaa cgtcaaaggg cgaaaaaccg tctatcaggg cgatggccca ctacgtgaac    13200
catcacccaa atcaagtttt ttgcggtcga ggtgccgtaa agctctaaat cggaaccta     13260 aagggagccc ccgatttaga gcttgacggg gaaagccggc gaacgtggcg agaaaggaag    13320
ggaagaaagc gaaaggagcg ggcgctaggg cgctggcaag tgtagcggtc acgctgcgcg    13380
taaccaccac acccgcgcgc ttaatgcgcc g                                   13418
```

<210> SEQ ID NO 4
<211> LENGTH: 12887
<212> TYPE: DNA

<213> ORGANISM: Artificial Sequence
<220> FEATURE:
<223> OTHER INFORMATION: The adeno shuttle vector containing multi-RFs under CMV weak promoter (CMVWP) has been provided as pAd(CMVWP)-GFP-KSO (K; KLF4, S; SOX2, O; OCT3/4).
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (12)..(14)
<223> OTHER INFORMATION: n is a, c, g, or t
<220> FEATURE:
<221> NAME/KEY: misc_feature
<222> LOCATION: (355)..(357)
<223> OTHER INFORMATION: n is a, c, g, or t
<220> FEATURE:
<221> NAME/KEY: misc_feature
<222> LOCATION: (5715)..(5715)
<223> OTHER INFORMATION: n is a, c, g, or t
<220> FEATURE:
<221> NAME/KEY: misc_feature
<222> LOCATION: (6773)..(6775)
<223> OTHER INFORMATION: n is a, c, g, or t
<220> FEATURE:
<221> NAME/KEY: misc_feature
<222> LOCATION: (9016)..(9018)
<223> OTHER INFORMATION: n is a, c, g, or t
<220> FEATURE:
<221> NAME/KEY: misc_feature
<222> LOCATION: (9033)..(9035)
<223> OTHER INFORMATION: n is a, c, g, or t
<220> FEATURE:
<221> NAME/KEY: misc_feature
<222> LOCATION: (10018)..(10020)
<223> OTHER INFORMATION: n is a, c, g, or t
<220> FEATURE:
<221> NAME/KEY: misc_feature
<222> LOCATION: (10035)..(10037)
<223> OTHER INFORMATION: n is a, c, g, or t
<220> FEATURE:
<221> NAME/KEY: misc_feature
<222> LOCATION: (11338)..(11343)
<223> OTHER INFORMATION: n is a, c, g, or t
<220> FEATURE:
<221> NAME/KEY: misc_feature
<222> LOCATION: (12881)..(12887)
<223> OTHER INFORMATION: n is a, c, g, or t

<400> SEQUENCE: 4

```
nnnttaatta annntccctt ccagctctct gccccttttg gattgaagcc aatatgataa      60 tgaggggtg gagtttgtga cgtggcgcgg ggcgtgggaa cggggcgggt gacgtagtag     120
tgtggcggaa gtgtgatgtt gcaagtgtgg cggaacacat gtaagcgacg gatgtggcaa    180
aagtgacgtt tttggtgtgc gccggtgtac acaggaagtg acaattttcg cgcggtttta    240
ggcggatgtt gtagtaaatt tgggcgtaac cgagtaagat ttggccattt tcgcgggaaa    300
actgaataag aggaagtgaa atctgaataa ttttgtgtta ctcatagcgc gtaannnggt    360
accgcggcct aatagtaatc aattacgggg tcattagttc atagcccata tatgagttc    420 cgcgttacat aacttacggt aaatggcccg cctggctgac cgcccaacga ccccccgccca    480 ttgacgtcaa tgggagtttg ttttggcacc aaaatcaacg ggactttcca aaatgtcgta    540
acaactccgc cccattgacg caaatgggcg gtaggcgtgt acgtggggag gtctatataa    600
gcagagctgg tttagtgaac cgtcagatcc gctagcgcta ccggactcag atctcgagct    660
caagcttcga attctgcagt cgacggtacc gcgggcccgg gatccaccgg tcgccaccat    720
ggtgagcaag ggcgaggagc tgttcaccgg ggtggtgccc atcctggtcg agctggacgg    780
cgacgtaaac ggccacaagt tcagcgtgtc cggcgagggc gagggcgatg ccacctacgg    840
```

```
caagctgacc ctgaagttca tctgcaccac cggcaagctg cccgtgccct ggcccaccct    900
cgtgaccacc ctgacctacg gcgtgcagtg cttcagccgc taccccgacc acatgaagca    960
gcacgacttc ttcaagtccg ccatgcccga aggctacgtc caggagcgca ccatcttctt   1020
caaggacgac ggcaactaca agacccgcgc cgaggtgaag ttcgagggcg acaccctggt   1080
gaaccgcatc gagctgaagg gcatcgactt caaggaggac ggcaacatcc tggggcacaa   1140
gctggagtac aactacaaca gccacaacgt ctatatcatg gccgacaagc agaagaacgg   1200
catcaaggtg aacttcaaga tccgccacaa catcgaggac ggcagcgtgc agctcgccga   1260
ccactaccag cagaacaccc ccatcggcga cggccccgtg ctgctgcccg acaaccacta   1320
cctgagcacc cagtccgccc tgagcaaaga ccccaacgag aagcgcgatc acatggtcct   1380
gctggagttc gtgaccgccg ccgggatcac tctcggcatg gacgagctgt acaagtaaag   1440
cggccgcgac tctagatcat aatcagccat accacatttg tagaggtttt acttgcttta   1500
aaaaacctcc cacacctccc cctgaacctg aaacataaaa tgaatgcaat tgttgttgtt   1560
aacttgttta ttgcagctta taatggttac aaataaagca atagcatcac aaatttcaca   1620
aataaagcat ttttttcact gcattctagt tgtggtttgt ccaaactcat caatgtatct   1680
taaggccgcc tcgagtctag agataattca gtaatcaatt acggggtcat tagttcatag   1740
cccatatatg gagttccgcg ttacataact tacggtaaat ggcccgcctg gctgaccgcc   1800
caacgacccc cgcccattga cgtcaatggg agtttgtttt ggcaccaaaa tcaacgggac   1860
tttccaaaat gtcgtaacaa ctccgcccca ttgacgcaaa tgggcggtag gcgtgtacgg   1920
tgggaggtct atataagcag agctggttta gtgaaccgtc agatccgcta gcatggctgt   1980
cagcgacgcg ctgctcccat ctttctccac gttcgcgtct ggcccggcgg aagggagaa   2040
gacactgcgt caagcaggtg cccgaataa ccgctggcgg gaggagctct cccacatgaa   2100
gcgacttccc ccagtgcttc ccggccgccc ctatgacctg gcggcggcga ccgtggccac   2160
agacctggag agcggcggag ccggtgcggc ttgcggcggt agcaacctgg cgcccctacc   2220
tcggagagag accgaggagt tcaacgatct cctggacctg gactttattc tctccaattc   2280
gctgacccat cctccggagt cagtggccgc caccgtgtcc tcgtcagcgt cagcctcctc   2340
ttcgtcgtcg ccgtcgagca gcggccctgc cagcgcgccc tccacctgca gcttcaccta   2400
tccgatccgg gccgggaacg acccgggcgt ggcgccgggc ggcacgggcg aggcctcct   2460
ctatggcagg gagtccgctc cccctccgac ggctcccttc aacctggcgg acatcaacga   2520
cgtgagcccc tcgggcggct tcatggccga gctcctgcgg ccagaattgg acccggtgta   2580
cattccgccg cagcagccgc agccgccagg tggcgggctg atgggcaagt tcgtgctgaa   2640
ggcgtcgctg agcgccctg gcagcgagta cggcagcccg tcggtcatca gcgtcagcaa   2700
aggcagccct gacggcagcc acccggtggt ggtggcgccc tacaacggcg gccgccgcg   2760
cacgtgcccc aagatcaagc aggaggcggt ctcttcgtgc acccacttgg gcgctggacc   2820
ccctctcagc aatggccacc ggccggctgc acacgacttc cccctggggc ggcagctccc   2880
cagcaggact accccgaccc tgggtcttga ggaagtgctg agcagcaggg actgtcaccc   2940
tgccctgccg cttcctcccg gcttccatcc ccacccgggg cccaattacc catccttcct   3000
gcccgatcag atgcagccgc aagtcccgcc gctccattac caagagctca tgccacccgg   3060
ttcctgcatg ccagaggagc ccaagccaaa gaggggaaga cgatcgtggc cccgaaaag   3120
gaccgccacc cacacttgtg attacgcggg ctgcggcaaa acctacacaa agagttccca   3180
```

```
tctcaaggca cacctgcgaa cccacacagg tgagaaacct taccactgtg actgggacgg    3240
ctgtggatgg aaattcgccc gctcagatga actgaccagg cactaccgta aacacacggg    3300
gcaccgcccg ttccagtgcc aaaaatgcga ccgagcattt tccaggtcgg accacctcgc    3360
cttacacatg aagaggcatt tttaagctag cgctaccgga ctcagatcgg ccgcgactct    3420
agatcataat cagccatacc acatttgtag aggttttact tgctttaaaa aacctcccac    3480
acctccccct gaacctgaaa cataaaatga atgcaattgt tgttgttaac ttgtttattg    3540
cagcttataa tggttacaaa taaagcaata gcatcacaaa tttcacaaat aaagcatttt    3600
tttcactgca ttctagttgt ggtttgtcca aactcatcaa tgtatgaatt atcgaattca    3660
agcttagtaa tcaattacgg ggtcattagt tcatagccca tatatggagt tccgcgttac    3720
ataacttacg gtaaatggcc cgcctggctg accgcccaac gacccccgcc cattgacgtc    3780
aatgggagtt tgttttggca ccaaaatcaa cgggactttc caaaatgtcg taacaactcc    3840
gccccattga cgcaaatggg cggtaggcgt gtacggtggg aggtctatat aagcagagct    3900
ggtttagtga accgtcagat ccgctagcat gtacaacatg atggagacgg agctgaagcc    3960
gccgggcccg cagcaaactt cggggggcgg cggcggcaac tccaccgcgg cggcggccgg    4020
cggcaaccag aaaaacagcc cggaccgcgt caagcggccc atgaatgcct tcatggtgtg    4080
gtcccgcggg cagcggcgca agatggccca ggagaacccc aagatgcaca actcggagat    4140
cagcaagcgc ctgggcgccg agtggaaact tttgtcggag acgagaagc ggccgttcat    4200 cgacgaggct aagcggctgc gagcgctgca catgaaggag cacccggatt ataaataccg    4260
gccccggcgg aaaaccaaga cgctcatgaa gaaggataag tacacgctgc ccggcgggct    4320
gctggccccc ggcggcaata gcatggcgag cggggtcggg gtgggcgccg gcctgggcgc    4380
gggcgtgaac cagcgcatgg acagttacgc gcacatgaac ggctggagca acggcagcta    4440
cagcatgatg caggaccagc tgggctaccc gcagcacccg ggcctcaatg cgcacggcgc    4500
agcgcagatg cagcccatgc accgctacga cgtgagcgcc ctgcagtaca actccatgac    4560
cagctcgcag acctacatga acggctcgcc cacctacagc atgtcctact cgcagcaggg    4620
cacccctggc atggctcttg gctccatggg ttcggtggtc aagtccgagg ccagctccag    4680
cccccctgtg gttacctctt cctcccactc cagggcgccc tgccaggccg ggacctccg    4740 ggacatgatc agcatgtatc tcccggcgc cgaggtgccg gaaccgccg ccccagcag    4800 acttcacatg tcccagcact accagagcgg cccggtgccc ggcacggcca ttaacggcac    4860
actgcccctc tcacacatgt gagctagcgc taccggactc agatcggccg cgactctaga    4920
tcataatcag ccataccaca tttgtagagg ttttacttgc tttaaaaaac ctcccacacc    4980
tccccctgaa cctgaaacat aaaatgaatg caattgttgt tgttaacttg tttattgcag    5040
cttataatgg ttacaaataa agcaatagca tcacaaattt cacaaataaa gcattttttt    5100
cactgcattc tagttgtggt ttgtccaaac tcatcaatgt ataagcttgt cgacagtaat    5160
caattacggg gtcattagtt catagcccat atatggagtt ccgcgttaca taacttacgg    5220
taaatggccc gcctggctga ccgcccaacg acccccgccc attgacgtca atgggagttt    5280
gttttggcac caaaatcaac gggactttcc aaaatgtcgt aacaactccg ccccattgac    5340
gcaaatgggc ggtaggcgtg tacggtggga ggtctatata agcagagctg gtttagtgaa    5400
ccgtcagatc cgctagcatg gcgggacacc tggcttcgga tttcgccttc tcgcccctc    5460 caggtggtga aggtgatggg ccaggggggc cggagccggg ctgggttgat cctcggacct    5520
ggctaagctt ccaaggccct cctggagggc caggaatcgg gccgggggtt gggccaggct    5580
```

```
ctgaggtgtg ggggattccc ccatgccccc cgccgtatga gttctgtggg gggatggcgt    5640
actgtgggcc ccaggttgga gtggggctag tgccccaagg cggcttggag acctctcagc    5700
ctgagggtga agcangagtc ggggtggaga gcaactccga tggggcctcc ccggagccct    5760
gcaccgtcac ccctggtgcc gtgaagctgg agaaggagag gctggagcaa aacccggagg    5820
agtcccagga catcaaagct ctgcagaaag aactcgagca atttgccaag ctcctgaagc    5880
agaagaggat caccctggga tatacacagg ccgatgtggg gctcaccctg ggggttctat    5940
ttgggaaggt attcagccaa acgaccatct gccgctttga ggctctgcag cttagcttca    6000
agaacatgtg taagctgcgg cccttgctgc agaagtgggt ggaggaagct gacaacaatg    6060
aaaatcttca ggagatatgc aaagcagaaa ccctcgtgca ggcccgaaag agaaagcgaa    6120
ccagtatcga gaaccgagtg agaggcaacc tggagaattt gttcctgcag tgcccgaaac    6180
ccacactgca gcagatcagc cacatcgccc agcagcttgg gctcgagaag gatgtggtcc    6240
gagtgtggtt ctgtaaccgg cgccagaagg gcaagcgatc aagcagcgac tatgcacaac    6300
gagaggattt tgaggctgct gggtctcctt tctcaggggg accagtgtcc tttcctctgg    6360
ccccagggcc ccattttggt accccaggct atgggagccc tcacttcact gcactgtact    6420
cctcggtccc tttccctgag ggggaagcct ttccccctgt ctccgtcacc actctgggct    6480
ctcccatgca ttcaaactga gctagcgcta ccggactcag atcggccgcg actctagatc    6540
ataatcagcc ataccacatt tgtagaggtt ttacttgctt taaaaaacct cccacacctc    6600
cccctgaacc tgaaacataa aatgaatgca attgttgttg ttaacttgtt tattgcagct    6660
tataatggtt acaaataaag caatagcatc acaaatttca caaataaagc attttttttca    6720 ctgcattcta gttgtggttt gtccaaactc atcaatgtat gtcgacagat ctnnntaagg    6780
gtgggaaaga atatataagg tgggggtctt atgtagtttt gtatctgttt tgcagcagcc    6840
gccgccgcca tgagcaccaa ctcgtttgat ggaagcattg tgagctcata tttgacaacg    6900
cgcatgcccc catgggccgg ggtgcgtcag aatgtgatgg gctccagcat tgatggtcgc    6960
cccgtcctgc ccgcaaactc tactaccttg acctacgaga ccgtgtctgg aacgccgttg    7020
gagactgcag cctccgccgc cgcttcagcc gctgcagcca ccgcccgcgg gattgtgact    7080
gactttgctt tcctgagccc gcttgcaagc agtgcagctt cccgttcatc cgcccgcgat    7140
gacaagttga cggctctttt ggcacaattg gattctttga cccgggaact taatgtcgtt    7200
tctcagcagc tgttggatct gcgccagcag gtttctgccc tgaaggcttc ctcccctccc    7260
aatgcggttt aaaacataaa taaaaaacca gactctgttt ggatttggat caagcaagtg    7320
tcttgctgtc tttatttagg ggttttgcgc gcgcggtagg cccgggacca gcggtctcgg    7380
tcgttgaggg tcctgtgtat ttttttccagg acgtggtaaa ggtgactctg gatgttcaga    7440
tacatgggca taagcccgtc tctggggtgg aggtagcacc actgcagagc ttcatgctgc    7500
ggggtggtgt tgtagatgat ccagtcgtag caggagcgct gggcgtggtg cctaaaaatg    7560
tctttcagta gcaagctgat tgccaggggc aggcccttgg tgtaagtgtt tacaaagcgg    7620
ttaagctggg atgggtgcat acgtggggat atgagatgca tcttggactg tattttttagg    7680 ttggctatgt tcccagccat atccctccgg ggattcatgt tgtgcagaac caccagcaca    7740
gtgtatccgg tgcacttggg aaatttgtca tgtagcttag aaggaaatgc gtggaagaac    7800
ttggagacgc ccttgtgacc tccaagattt tccatgcatt cgtccataat gatggcaatg    7860
ggcccacggg cggcggcctg ggcgaagata tttctgggat cactaacgtc atagttgtgt    7920
```

```
tccaggatga gatcgtcata ggccattttt acaaagcgcg ggcggagggt gccagactgc    7980
ggtataatgg ttccatccgg cccaggggcg tagttaccct cacagatttg catttcccac    8040
gctttgagtt cagatggggg gatcatgtct acctgcgggg cgatgaagaa aacggtttcc    8100
ggggtagggg agatcagctg ggaagaaagc aggttcctga gcagctgcga cttaccgcag    8160
ccggtgggcc cgtaaatcac acctattacc gggtgcaact ggtagttaag agagctgcag    8220
ctgccgtcat ccctgagcag gggggccact tcgttaagca tgtccctgac tcgcatgttt    8280
tccctgacca aatccgccag aaggcgctcg ccgcccagcg atagcagttc ttgcaaggaa    8340
gcaaagtttt tcaacggttt gagaccgtcc gccgtaggca tgcttttgag cgtttgacca    8400
agcagttcca ggcggtccca cagctcggtc acctgctcta cggcatctcg atccagcata    8460
tctcctcgtt tcgcgggttg gggcggcttt cgctgtacgg cagtagtcgg tgctcgtcca    8520
gacgggccag ggtcatgtct ttccacgggc gcagggtcct cgtcagcgta gtctgggtca    8580
cggtgaaggg gtgcgctccg ggctgcgcgc tggccagggt gcgcttgagg ctggtcctgc    8640
tggtgctgaa gcgctgccgg tcttcgccct gcgcgtcggc caggtagcat ttgaccatgg    8700
tgtcatagtc cagcccctcc gcggcgtggc ccttggcgcg cagcttgccc ttggaggagg    8760
cgccgcacga ggggcagtgc agacttttga gggcgtagag cttgggcgcg agaaataccg    8820
attccgggga gtaggcatcc gcgccgcagg ccccgcagac ggtctcgcat ccacgagcc    8880
aggtgagctc tggccgttcg gggtcaaaaa ccaggtttcc cccatgcttt ttgatgcgtt    8940
tcttacctct ggtttccatg agccggtgtc cacgctcggt gacgaaaagg ctgtccgtgt    9000
ccccgtatac agactnnngt ttaaacgaat tcnnntataa aatgcaaggt gctgctcaaa    9060
aaatcaggca aagcctcgcg caaaaaagaa agcacatcgt agtcatgctc atgcagataa    9120
aggcaggtaa gctccggaac caccacagaa aaagacacca ttttctctc aaacatgtct    9180
gcgggtttct gcataaacac aaaataaaat aacaaaaaaa catttaaaca ttagaagcct    9240
gtcttacaac aggaaaaaca acccttataa gcataagacg gactacggcc atgccggcgt    9300
gaccgtaaaa aaactggtca ccgtgattaa aaagcaccac cgacagctcc tcggtcatgt    9360
ccggagtcat aatgtaagac tcggtaaaca catcaggttg attcatcggt cagtgctaaa    9420
aagcgaccga aatagcccgg gggaatacat acccgcaggc gtagagacaa cattacagcc    9480
cccataggag gtataacaaa attaatagga gagaaaaaca cataaacacc tgaaaaaccc    9540
tcctgcctag gcaaaatagc accctcccgc tccagaacaa catacagcgc ttcacagcgg    9600
cagcctaaca gtcagcccta ccagtaaaaa agaaaaccta ttaaaaaaac accactcgac    9660
acggcaccag ctcaatcagt cacagtgtaa aaaagggcca agtgcagagc gagtatatat    9720
aggactaaaa aatgacgtaa cggttaaagt ccacaaaaaa cacccagaaa accgcacgcg    9780
aacctacgcc cagaaacgaa agccaaaaaa cccacaactt cctcaaatcg tcacttccgt    9840
tttcccacgt tacgtaactt cccatttaa gaaaactaca attcccaaca catacaagtt    9900
actccgccct aaaacctacg tcacccgccc cgttcccacg ccccgcgcca cgtcacaaac    9960
tccaccccct cattatcata ttggcttcaa tccaaaataa ggtatattat tgatgatnnn   10020
ttaattaagg atccnnncgg tgtgaaatac cgcacagatg cgtaaggaga aaataccgca   10080
tcaggcgctc ttccgcttcc tcgctcactg actcgctgcg ctcggtcgtt cggctgcggc   10140
gagcggtatc agctcactca aaggcggtaa tacggttatc cacagaatca ggggataacg   10200
caggaaagaa catgtgagca aaaggccagc aaaaggccag gaaccgtaaa aaggccgcgt   10260
tgctggcgtt tttccatagg ctccgccccc ctgacgagca tcacaaaaat cgacgctcaa   10320
```

```
gtcagaggtg gcgaaacccg acaggactat aaagatacca ggcgtttccc cctggaagct    10380
ccctcgtgcg ctctcctgtt ccgaccctgc cgcttaccgg atacctgtcc gcctttctcc    10440
cttcgggaag cgtggcgctt tctcatagct cacgctgtag gtatctcagt tcggtgtagg    10500
tcgttcgctc caagctgggc tgtgtgcacg aaccccccgt tcagcccgac cgctgcgcct    10560
tatccggtaa ctatcgtctt gagtccaacc cggtaagaca cgacttatcg ccactggcag    10620
cagccactgg taacaggatt agcagagcga ggtatgtagg cggtgctaca gagttcttga    10680
agtggtggcc taactacggc tacactagaa ggacagtatt tggtatctgc gctctgctga    10740
agccagttac cttcggaaaa agagttggta gctcttgatc cggcaaacaa accaccgctg    10800
gtagcggtgg ttttttttgtt tgcaagcagc agattacgcg cagaaaaaaa ggatctcaag    10860
aagatccttt gatcttttct acggggtctg acgctcagtg gaacgaaaac tcacgttaag    10920
ggattttggt catgagatta tcaaaaagga tcttcaccta gatccttttta aattaaaaat    10980 gaagttttaa atcaatctaa agtatatatg agtaaacttg gtctgacagt taccaatgct    11040
taatcagtga ggcacctatc tcagcgatct gtctatttcg ttcatccata gttgcctgac    11100
tccccgtcgt gtagataact acgatacggg agggcttacc atctggcccc agtgctgcaa    11160
tgataccgcg agacccacgc tcaccggctc cagatttatc agcaataaac cagccagccg    11220
gaagggccga gcgcagaagt ggtcctgcaa ctttatccgc ctccatccag tctattaatt    11280
gttgccggga agctagagta agtagttcgc cagttaatag tttgcgcaac gttgttgnnn    11340
nnnaaaaagg atcttcacct agatcctttt cacgtagaaa gccagtccgc agaaacggtg    11400
ctgaccccgg atgaatgtca gctactgggc tatctggaca agggaaaacg caagcgcaaa    11460
gagaaagcag gtagcttgca gtgggcttac atggcgatag ctagactggg cggttttatg    11520
gacagcaagc gaaccggaat tgccagctgg ggcgccctct ggtaaggttg gaagccctg    11580 caaagtaaac tggatggctt tctcgccgcc aaggatctga tggcgcaggg gatcaagctc    11640
tgatcaagag acaggatgag gatcgtttcg catgattgaa caagatggat tgcacgcagg    11700
ttctccggcc gcttgggtgg agaggctatt cggctatgac tgggcacaac agacaatcgg    11760
ctgctctgat gccgccgtgt tccggctgtc agcgcagggg cgcccggttc tttttgtcaa    11820
gaccgacctg tccggtgccc tgaatgaact gcaagacgag gcagcgcggc tatcgtggct    11880
ggccacgacg ggcgttcctt gcgcagctgt gctcgacgtt gtcactgaag cgggaaggga    11940
ctggctgcta ttgggcgaag tgccggggca ggatctcctg tcatctcacc ttgctcctgc    12000
cgagaaagta tccatcatgg ctgatgcaat gcggcggctg catacgcttg atccggctac    12060
ctgcccattc gaccaccaag cgaaacatcg catcgagcga gcacgtactc ggatggaagc    12120
cggtcttgtc gatcaggatg atctggacga agagcatcag gggctcgcgc cagccgaact    12180
gttcgccagg ctcaaggcga gcatgcccga cggcgaggat ctcgtcgtga cccatggcga    12240
tgcctgcttg ccgaatatca tggtggaaaa tggccgcttt tctggattca tcgactgtgg    12300
ccggctgggt gtggcggacc gctatcagga catagcgttg gctacccgtg atattgctga    12360
agagcttggc ggcgaatggg ctgaccgctt cctcgtgctt tacggtatcg ccgctcccga    12420
ttcgcagcgc atcgccttct atcgccttct tgacgagttc ttctgaattt tgttaaaatt    12480
tttgttaaat cagctcattt tttaaccaat aggccgaaat cggcaacatc ccttataaat    12540
caaaagaata accgcgata gggttgagtg ttgttccagt ttggaacaag agtccactat    12600
taaagaacgt ggactccaac gtcaagggc gaaaaccgt ctatcagggc gatggcccac    12660
```

```
tacgtgaacc atcacccaaa tcaagttttt tgcggtcgag gtgccgtaaa gctctaaatc  12720
ggaaccctaa agggagcccc cgatttagag cttgacgggg aaagccggcg aacgtggcga  12780
gaaaggaagg gaagaaagcg aaaggagcgg gcgctagggc gctggcaagt gtagcggtca  12840
cgctgcgcgt aaccaccaca cccgcgcgct taatgcgccg nnnnnnn              12887
```

<210> SEQ ID NO 5
<211> LENGTH: 24
<212> TYPE: DNA
<213> ORGANISM: Artificial Sequence
<220> FEATURE:
<223> OTHER INFORMATION: Entirely synthesized

<400> SEQUENCE: 5

```
agccatgggc ccttggagcc gcag                                          24
```

<210> SEQ ID NO 6
<211> LENGTH: 25
<212> TYPE: DNA
<213> ORGANISM: Artificial Sequence
<220> FEATURE:
<223> OTHER INFORMATION: Entirely Synthesized

<400> SEQUENCE: 6

```
ggaataaccc agtctctctt ctgtc                                         25
```

<210> SEQ ID NO 7
<211> LENGTH: 25
<212> TYPE: DNA
<213> ORGANISM: Artificial Sequence
<220> FEATURE:
<223> OTHER INFORMATION: Entirely Synthesized

<400> SEQUENCE: 7

```
tgcggcccga agatgacatg aaacc                                         25
```

<210> SEQ ID NO 8
<211> LENGTH: 24
<212> TYPE: DNA
<213> ORGANISM: Artificial Sequence
<220> FEATURE:
<223> OTHER INFORMATION: Entirely Synthesized

<400> SEQUENCE: 8

```
cccaggaggc tctcaggacc gctc                                          24
```

<210> SEQ ID NO 9
<211> LENGTH: 24
<212> TYPE: DNA
<213> ORGANISM: Artificial Sequence
<220> FEATURE:
<223> OTHER INFORMATION: Entirely Synthesized

<400> SEQUENCE: 9

```
gaggaggctg cagcagcgga agac                                          24
```

<210> SEQ ID NO 10
<211> LENGTH: 24
<212> TYPE: DNA
<213> ORGANISM: Artificial Sequence
<220> FEATURE:
<223> OTHER INFORMATION: Entirely Synthesized

<400> SEQUENCE: 10

```
gagccagcag gctgatgccc tcac                                          24
```

<210> SEQ ID NO 11
<211> LENGTH: 28
<212> TYPE: DNA
<213> ORGANISM: Artificial Sequence
<220> FEATURE:
<223> OTHER INFORMATION: Entirely Synthesized

<400> SEQUENCE: 11
ccttgcccaa aatcccctat gtcaaagc                                28

<210> SEQ ID NO 12
<211> LENGTH: 26
<212> TYPE: DNA
<213> ORGANISM: Artificial Sequence
<220> FEATURE:
<223> OTHER INFORMATION: Entirely Synthesized

<400> SEQUENCE: 12
gtatcgccaa tgccgcctga gacctc                                  26

<210> SEQ ID NO 13
<211> LENGTH: 23
<212> TYPE: DNA
<213> ORGANISM: Artificial Sequence
<220> FEATURE:
<223> OTHER INFORMATION: Entirely Synthesized

<400> SEQUENCE: 13
attataaatc tagagactcc agg                                     23

<210> SEQ ID NO 14
<211> LENGTH: 24
<212> TYPE: DNA
<213> ORGANISM: Artificial Sequence
<220> FEATURE:
<223> OTHER INFORMATION: Entirely Synthesized

<400> SEQUENCE: 14
catggaggaa ggaagaggag agac                                    24

<210> SEQ ID NO 15
<211> LENGTH: 25
<212> TYPE: DNA
<213> ORGANISM: Artificial Sequence
<220> FEATURE:
<223> OTHER INFORMATION: Entirely Synthesized

<400> SEQUENCE: 15
ctgctgcctg aatgggggaa cctgc                                   25

<210> SEQ ID NO 16
<211> LENGTH: 27
<212> TYPE: DNA
<213> ORGANISM: Artificial Sequence
<220> FEATURE:
<223> OTHER INFORMATION: Entirely Synthesized

<400> SEQUENCE: 16
gccacgaggt gctcatccat cacaagg                                 27

<210> SEQ ID NO 17
<211> LENGTH: 24
<212> TYPE: DNA
<213> ORGANISM: Artificial Sequence
<220> FEATURE:

<223> OTHER INFORMATION: Entirely Synthesized

<400> SEQUENCE: 17
ttataaggcg gcggggtgg tggc                                              24

<210> SEQ ID NO 18
<211> LENGTH: 25
<212> TYPE: DNA
<213> ORGANISM: Artificial Sequence
<220> FEATURE:
<223> OTHER INFORMATION: Entirely Synthesized

<400> SEQUENCE: 18
cgaaggggaa cttgtccatc tccag                                            25

<210> SEQ ID NO 19
<211> LENGTH: 22
<212> TYPE: DNA
<213> ORGANISM: Artificial Sequence
<220> FEATURE:
<223> OTHER INFORMATION: Entirely Synthesized

<400> SEQUENCE: 19
atcatccgca gcctacaggc ag                                               22

<210> SEQ ID NO 20
<211> LENGTH: 23
<212> TYPE: DNA
<213> ORGANISM: Artificial Sequence
<220> FEATURE:
<223> OTHER INFORMATION: Entirely Synthesized

<400> SEQUENCE: 20
ctgtccctcc tgggcccgcc agg                                              23

<210> SEQ ID NO 21
<211> LENGTH: 26
<212> TYPE: DNA
<213> ORGANISM: Artificial Sequence
<220> FEATURE:
<223> OTHER INFORMATION: Entirely Synthesized

<400> SEQUENCE: 21
cctgctcaag ctgactcgac accgtg                                           26

<210> SEQ ID NO 22
<211> LENGTH: 25
<212> TYPE: DNA
<213> ORGANISM: Artificial Sequence
<220> FEATURE:
<223> OTHER INFORMATION: Entirely Synthesized

<400> SEQUENCE: 22
ggaaaagctg gccctggggt ggagc                                            25

<210> SEQ ID NO 23
<211> LENGTH: 24
<212> TYPE: DNA
<213> ORGANISM: Artificial Sequence
<220> FEATURE:
<223> OTHER INFORMATION: Entirely Synthesized

<400> SEQUENCE: 23
ctcaaccagc agctcctaga aggg                                             24

```
<210> SEQ ID NO 24
<211> LENGTH: 23
<212> TYPE: DNA
<213> ORGANISM: Artificial Sequence
<220> FEATURE:
<223> OTHER INFORMATION: Entirely Synthesized

<400> SEQUENCE: 24
gctggcccgc gcctggcagc tgc                                                23

<210> SEQ ID NO 25
<211> LENGTH: 24
<212> TYPE: DNA
<213> ORGANISM: Artificial Sequence
<220> FEATURE:
<223> OTHER INFORMATION: Entirely Synthesized

<400> SEQUENCE: 25
cttatgctac gtaaaggagc tggg                                               24

<210> SEQ ID NO 26
<211> LENGTH: 24
<212> TYPE: DNA
<213> ORGANISM: Artificial Sequence
<220> FEATURE:
<223> OTHER INFORMATION: Entirely Synthesized

<400> SEQUENCE: 26
gtgccaaccc aggtcccgga agtt                                               24

<210> SEQ ID NO 27
<211> LENGTH: 25
<212> TYPE: DNA
<213> ORGANISM: Artificial Sequence
<220> FEATURE:
<223> OTHER INFORMATION: Entirely Synthesized

<400> SEQUENCE: 27
tgaaggtcgg agtcaacgga tttgg                                              25

<210> SEQ ID NO 28
<211> LENGTH: 21
<212> TYPE: DNA
<213> ORGANISM: Artificial Sequence
<220> FEATURE:
<223> OTHER INFORMATION: Entirely Synthesized

<400> SEQUENCE: 28
ggaggccatg tgggccatga g                                                  21

<210> SEQ ID NO 29
<211> LENGTH: 25
<212> TYPE: DNA
<213> ORGANISM: Artificial Sequence
<220> FEATURE:
<223> OTHER INFORMATION: Entirely Synthesized

<400> SEQUENCE: 29
ctacaacgcc tacgagtcct acaag                                              25

<210> SEQ ID NO 30
<211> LENGTH: 24
<212> TYPE: DNA
<213> ORGANISM: Artificial Sequence
<220> FEATURE:
<223> OTHER INFORMATION: Entirely Synthesized
```

<400> SEQUENCE: 30
gttgcaccag aaaagtcaga gttg				24

<210> SEQ ID NO 31
<211> LENGTH: 26
<212> TYPE: DNA
<213> ORGANISM: Artificial Sequence
<220> FEATURE:
<223> OTHER INFORMATION: Entirely Synthesized

<400> SEQUENCE: 31
aggagtccca ggacatcaaa gctctg				26

<210> SEQ ID NO 32
<211> LENGTH: 25
<212> TYPE: DNA
<213> ORGANISM: Artificial Sequence
<220> FEATURE:
<223> OTHER INFORMATION: Entirely Synthesized

<400> SEQUENCE: 32
ccggcggcaa tagcatggcg agcgg				25

<210> SEQ ID NO 33
<211> LENGTH: 24
<212> TYPE: DNA
<213> ORGANISM: Artificial Sequence
<220> FEATURE:
<223> OTHER INFORMATION: Entirely Synthesized

<400> SEQUENCE: 33
atatcccgcc gtgggtgaaa gttc				24

<210> SEQ ID NO 34
<211> LENGTH: 24
<212> TYPE: DNA
<213> ORGANISM: Artificial Sequence
<220> FEATURE:
<223> OTHER INFORMATION: Entirely Synthesized

<400> SEQUENCE: 34
actcagccat ggactggagc atcc				24

<210> SEQ ID NO 35
<211> LENGTH: 24
<212> TYPE: DNA
<213> ORGANISM: Artificial Sequence
<220> FEATURE:
<223> OTHER INFORMATION: Entirely Synthesized

<400> SEQUENCE: 35
tccaattcgc tgacccatcc tccg				24

<210> SEQ ID NO 36
<211> LENGTH: 28
<212> TYPE: DNA
<213> ORGANISM: Artificial Sequence
<220> FEATURE:
<223> OTHER INFORMATION: Entirely Synthesized

<400> SEQUENCE: 36
ccccaaagcc agaagatgca caaggagg				28

<210> SEQ ID NO 37
<211> LENGTH: 27

```
<212> TYPE: DNA
<213> ORGANISM: Artificial Sequence
<220> FEATURE:
<223> OTHER INFORMATION: Entirely Synthesized

<400> SEQUENCE: 37
cgtcgccaac catcttcctg tccctag                                    27

<210> SEQ ID NO 38
<211> LENGTH: 25
<212> TYPE: DNA
<213> ORGANISM: Artificial Sequence
<220> FEATURE:
<223> OTHER INFORMATION: Entirely Synthesized

<400> SEQUENCE: 38
atggtgaccg agctgctggg aggag                                      25

<210> SEQ ID NO 39
<211> LENGTH: 24
<212> TYPE: DNA
<213> ORGANISM: Artificial Sequence
<220> FEATURE:
<223> OTHER INFORMATION: Entirely Synthesized

<400> SEQUENCE: 39
atacattgat gagtttggac aaac                                       24

<210> SEQ ID NO 40
<211> LENGTH: 24
<212> TYPE: DNA
<213> ORGANISM: Artificial Sequence
<220> FEATURE:
<223> OTHER INFORMATION: Entirely Synthesized

<400> SEQUENCE: 40
gaggaggctg cagcagcgga agac                                       24

<210> SEQ ID NO 41
<211> LENGTH: 24
<212> TYPE: DNA
<213> ORGANISM: Artificial Sequence
<220> FEATURE:
<223> OTHER INFORMATION: Entirely Synthesized

<400> SEQUENCE: 41
ccactaggca ggccgttagg ctgg                                       24

<210> SEQ ID NO 42
<211> LENGTH: 21
<212> TYPE: DNA
<213> ORGANISM: Artificial Sequence
<220> FEATURE:
<223> OTHER INFORMATION: Entirely Synthesized

<400> SEQUENCE: 42
ggatacagca cagtaaggag c                                          21

<210> SEQ ID NO 43
<211> LENGTH: 19
<212> TYPE: DNA
<213> ORGANISM: Artificial Sequence
<220> FEATURE:
<223> OTHER INFORMATION: Entirely Synthesized

<400> SEQUENCE: 43
```
gcacagaccc acagttctc                                           19

<210> SEQ ID NO 44
<211> LENGTH: 22
<212> TYPE: DNA
<213> ORGANISM: Artificial Sequence
<220> FEATURE:
<223> OTHER INFORMATION: Entirely Synthesized

<400> SEQUENCE: 44
tctcccatgc attcaaactg ag                                       22

<210> SEQ ID NO 45
<211> LENGTH: 22
<212> TYPE: DNA
<213> ORGANISM: Artificial Sequence
<220> FEATURE:
<223> OTHER INFORMATION: Entirely Synthesized

<400> SEQUENCE: 45
cctttgtgtt cccaattcct tc                                       22

<210> SEQ ID NO 46
<211> LENGTH: 23
<212> TYPE: DNA
<213> ORGANISM: Artificial Sequence
<220> FEATURE:
<223> OTHER INFORMATION: Entirely Synthesized

<400> SEQUENCE: 46
cccgagactt atgctacgta aag                                      23

<210> SEQ ID NO 47
<211> LENGTH: 22
<212> TYPE: DNA
<213> ORGANISM: Artificial Sequence
<220> FEATURE:
<223> OTHER INFORMATION: Entirely Synthesized

<400> SEQUENCE: 47
ggcagacagg ttaaagtaga gg                                       22

<210> SEQ ID NO 48
<211> LENGTH: 21
<212> TYPE: DNA
<213> ORGANISM: Artificial Sequence
<220> FEATURE:
<223> OTHER INFORMATION: Entirely Synthesized

<400> SEQUENCE: 48
agctacaaac aggtgaagac c                                        21

<210> SEQ ID NO 49
<211> LENGTH: 22
<212> TYPE: DNA
<213> ORGANISM: Artificial Sequence
<220> FEATURE:
<223> OTHER INFORMATION: Entirely Synthesized

<400> SEQUENCE: 49
gtggtaggaa gagtaaaggc tg                                       22

<210> SEQ ID NO 50
<211> LENGTH: 22
<212> TYPE: DNA
<213> ORGANISM: Artificial Sequence

```
<220> FEATURE:
<223> OTHER INFORMATION: Entirely Synthesized

<400> SEQUENCE: 50
gatgtggagt atgagagtga cg                                           22

<210> SEQ ID NO 51
<211> LENGTH: 19
<212> TYPE: DNA
<213> ORGANISM: Artificial Sequence
<220> FEATURE:
<223> OTHER INFORMATION: Entirely Synthesized

<400> SEQUENCE: 51
ggtcaagggt caggagttc                                               19

<210> SEQ ID NO 52
<211> LENGTH: 20
<212> TYPE: DNA
<213> ORGANISM: Artificial Sequence
<220> FEATURE:
<223> OTHER INFORMATION: Entirely Synthesized

<400> SEQUENCE: 52
gcacggcttt tgttcagatg                                              20

<210> SEQ ID NO 53
<211> LENGTH: 20
<212> TYPE: DNA
<213> ORGANISM: Artificial Sequence
<220> FEATURE:
<223> OTHER INFORMATION: Entirely Synthesized

<400> SEQUENCE: 53
cggttgaagg tgagactggc                                              20

<210> SEQ ID NO 54
<211> LENGTH: 21
<212> TYPE: DNA
<213> ORGANISM: Artificial Sequence
<220> FEATURE:
<223> OTHER INFORMATION: Entirely Synthesized

<400> SEQUENCE: 54
caaggcaaag aatgaccgtt c                                            21

<210> SEQ ID NO 55
<211> LENGTH: 20
<212> TYPE: DNA
<213> ORGANISM: Artificial Sequence
<220> FEATURE:
<223> OTHER INFORMATION: Entirely Synthesized

<400> SEQUENCE: 55
tgctgaattc ctggtatcgc                                              20

<210> SEQ ID NO 56
<211> LENGTH: 20
<212> TYPE: DNA
<213> ORGANISM: Artificial Sequence
<220> FEATURE:
<223> OTHER INFORMATION: Entirely Synthesized

<400> SEQUENCE: 56
gcagaagcgc agatcaaaag                                              20
```

<210> SEQ ID NO 57
<211> LENGTH: 21
<212> TYPE: DNA
<213> ORGANISM: Artificial Sequence
<220> FEATURE:
<223> OTHER INFORMATION: Entirely Synthesized

<400> SEQUENCE: 57
cggacatgag gctaccatat g                                     21

<210> SEQ ID NO 58
<211> LENGTH: 20
<212> TYPE: DNA
<213> ORGANISM: Artificial Sequence
<220> FEATURE:
<223> OTHER INFORMATION: Entirely Synthesized

<400> SEQUENCE: 58
aggagtttca tccgaccaac                                       20

<210> SEQ ID NO 59
<211> LENGTH: 22
<212> TYPE: DNA
<213> ORGANISM: Artificial Sequence
<220> FEATURE:
<223> OTHER INFORMATION: Entirely Synthesized

<400> SEQUENCE: 59
tctgccatta tccacataca gc                                    22

<210> SEQ ID NO 60
<211> LENGTH: 20
<212> TYPE: DNA
<213> ORGANISM: Artificial Sequence
<220> FEATURE:
<223> OTHER INFORMATION: Entirely Synthesized

<400> SEQUENCE: 60
atcaacatcc acagcgagac                                       20

<210> SEQ ID NO 61
<211> LENGTH: 21
<212> TYPE: DNA
<213> ORGANISM: Artificial Sequence
<220> FEATURE:
<223> OTHER INFORMATION: Entirely Synthesized

<400> SEQUENCE: 61
caaccatctt cctgtcccta g                                     21

<210> SEQ ID NO 62
<211> LENGTH: 20
<212> TYPE: DNA
<213> ORGANISM: Artificial Sequence
<220> FEATURE:
<223> OTHER INFORMATION: Entirely Synthesized

<400> SEQUENCE: 62
ccatgaaggt cacccacttc                                       20

<210> SEQ ID NO 63
<211> LENGTH: 24
<212> TYPE: DNA
<213> ORGANISM: Artificial Sequence
<220> FEATURE:
<223> OTHER INFORMATION: Entirely Synthesized

```
<400> SEQUENCE: 63
ctcttgcatt aaactcttca tccg                                          24

<210> SEQ ID NO 64
<211> LENGTH: 21
<212> TYPE: DNA
<213> ORGANISM: Artificial Sequence
<220> FEATURE:
<223> OTHER INFORMATION: Entirely Synthesized

<400> SEQUENCE: 64
cccagcgaag agaatgaaga g                                             21

<210> SEQ ID NO 65
<211> LENGTH: 20
<212> TYPE: DNA
<213> ORGANISM: Artificial Sequence
<220> FEATURE:
<223> OTHER INFORMATION: Entirely Synthesized

<400> SEQUENCE: 65
aatggaacct gccttctcag                                               20

<210> SEQ ID NO 66
<211> LENGTH: 22
<212> TYPE: DNA
<213> ORGANISM: Artificial Sequence
<220> FEATURE:
<223> OTHER INFORMATION: Entirely Synthesized

<400> SEQUENCE: 66
cccaatacat ctcccttcac ag                                            22

<210> SEQ ID NO 67
<211> LENGTH: 21
<212> TYPE: DNA
<213> ORGANISM: Artificial Sequence
<220> FEATURE:
<223> OTHER INFORMATION: Entirely Synthesized

<400> SEQUENCE: 67
ccacctctaa ggccatcttt g                                             21

<210> SEQ ID NO 68
<211> LENGTH: 22
<212> TYPE: DNA
<213> ORGANISM: Artificial Sequence
<220> FEATURE:
<223> OTHER INFORMATION: Entirely Synthesized

<400> SEQUENCE: 68
gcgcacaatc attgagtttc tg                                            22

<210> SEQ ID NO 69
<211> LENGTH: 20
<212> TYPE: DNA
<213> ORGANISM: Artificial Sequence
<220> FEATURE:
<223> OTHER INFORMATION: Entirely Synthesized

<400> SEQUENCE: 69
agacaaacat gcccaggagg                                               20

<210> SEQ ID NO 70
```

```
<211> LENGTH: 23
<212> TYPE: DNA
<213> ORGANISM: Artificial Sequence
<220> FEATURE:
<223> OTHER INFORMATION: Entirely Synthesized

<400> SEQUENCE: 70
gaaggtgaag gtcggagtca acg                                              23

<210> SEQ ID NO 71
<211> LENGTH: 21
<212> TYPE: DNA
<213> ORGANISM: Artificial Sequence
<220> FEATURE:
<223> OTHER INFORMATION: Entirely Synthesized

<400> SEQUENCE: 71
gaagatggtg atgggatttc c                                                21

<210> SEQ ID NO 72
<211> LENGTH: 16309
<212> TYPE: DNA
<213> ORGANISM: artificial sequence
<220> FEATURE:
<223> OTHER INFORMATION: The pAdTrack adeno shuttle vector containing
      multi-reprogramming factors sequence has been provided as
      pAd-KcMOS.
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (12)..(14)
<223> OTHER INFORMATION: n is a, c, g, or t
<220> FEATURE:
<221> NAME/KEY: misc_feature
<222> LOCATION: (355)..(357)
<223> OTHER INFORMATION: n is a, c, g, or t
<220> FEATURE:
<221> NAME/KEY: misc_feature
<222> LOCATION: (1945)..(1947)
<223> OTHER INFORMATION: n is a, c, g, or t
<220> FEATURE:
<221> NAME/KEY: misc_feature
<222> LOCATION: (7317)..(7317)
<223> OTHER INFORMATION: n is a, c, g, or t
<220> FEATURE:
<221> NAME/KEY: misc_feature
<222> LOCATION: (10202)..(10204)
<223> OTHER INFORMATION: n is a, c, g, or t
<220> FEATURE:
<221> NAME/KEY: misc_feature
<222> LOCATION: (12445)..(12447)
<223> OTHER INFORMATION: n is a, c, g, or t
<220> FEATURE:
<221> NAME/KEY: misc_feature
<222> LOCATION: (12462)..(12464)
<223> OTHER INFORMATION: n is a, c, g, or t
<220> FEATURE:
<221> NAME/KEY: misc_feature
<222> LOCATION: (13447)..(13449)
<223> OTHER INFORMATION: n is a, c, g, or t
<220> FEATURE:
<221> NAME/KEY: misc_feature
<222> LOCATION: (13464)..(13466)
<223> OTHER INFORMATION: n is a, c, g, or t
<220> FEATURE:
<221> NAME/KEY: misc_feature
<222> LOCATION: (14767)..(14772)
<223> OTHER INFORMATION: n is a, c, g, or t

<400> SEQUENCE: 72
nnnttaatta annntcccctt ccagctctct gcccctttg gattgaagcc aatatgataa      60
```

```
tgaggggtg gagtttgtga cgtggcgcgg ggcgtgggaa cggggcgggt gacgtagtag        120
tgtggcggaa gtgtgatgtt gcaagtgtgg cggaacacat gtaagcgacg gatgtggcaa        180
aagtgacgtt tttggtgtgc gccggtgtac acaggaagtg acaattttcg cgcggtttta        240
ggcggatgtt gtagtaaatt tgggcgtaac cgagtaagat ttggccattt tcgcgggaaa        300
actgaataag aggaagtgaa atctgaataa ttttgtgtta ctcatagcgc gtaannncgc        360
gttaagatac attgatgagt ttggacaaac cacaactaga atgcagtgaa aaaaatgctt        420
tatttgtgaa atttgtgatg ctattgcttt atttgtaacc attataagct gcaataaaca        480
agttaacaac aacaattgca ttcattttat gtttcaggtt cagggggagg tgtgggaggt        540
tttttaaagc aagtaaaacc tctacaaatg tggtatggct gattatgatc agttatctag        600
atccggtgga tctgagtccg gacttgtaca gctcgtccat gccgagagtg atcccggcgg        660
cggtcacgaa ctccagcagg accatgtgat cgcgcttctc gttgggtct ttgctcaggg        720 cggactgggt gctcaggtag tggttgtcgg gcagcagcac ggggccgtcg ccatggggg        780 tgttctgctg gtagtggtcg gcgagctgca cgctgccgtc ctcgatgttg tggcggatct        840
tgaagttcac cttgatgccg ttcttctgct tgtcggccat gatatagacg ttgtggctgt        900
tgtagttgta ctccagcttg tgccccagga tgttgccgtc ctccttgaag tcgatgccct        960
tcagctcgat gcggttcacc agggtgtcgc cctcgaactt cacctcggcg cgggtcttgt       1020
agttgccgtc gtccttgaag aagatggtgc gctcctggac gtagccttcg ggcatggcgg       1080
acttgaagaa gtcgtgctgc ttcatgtggt cggggtagcg gctgaagcac tgcacgccgt       1140
aggtcagggt ggtcacgagg gtgggccagg gcacgggcag cttgccggtg gtgcagatga       1200
acttcagggt cagcttgccg taggtggcat cgccctcgcc ctcgccggac acgctgaact       1260
tgtggccgtt tacgtcgccg tccagctcga ccaggatggg caccaccccg gtgaacagct       1320
cctcgccctt gctcaccatg gtggcgaccg gtagcgctag cggatctgac ggttcactaa       1380
accagctctg cttatataga cctcccaccg tacacgccta ccgcccattt gcgtcaatgg       1440
ggcggagttg ttacgacatt ttggaaagtc ccgttgattt tggtgccaaa acaaactccc       1500
attgacgtca atggggtgga gacttggaaa tccccgtgag tcaaaccgct atccacgccc       1560
attgatgtac tgccaaaacc gcatcaccat ggtaatagcg atgactaata cgtagatgta       1620
ctgccaagta ggaaagtccc ataaggtcat gtactgggca taatgccagg cgggccattt       1680
accgtcattg acgtcaatag ggggcgtact tggcatatga tacacttgat gtactgccaa       1740
gtgggcagtt taccgtaaat actccaccca ttgacgtcaa tggaaagtcc ctattggcgt       1800
tactatggga acatacgtca ttattgacgt caatgggcgg gggtcgttgg gcggtcagcc       1860
aggcgggcca tttaccgtaa gttatgtaac gcggaactcc atatatgggc tatgaactaa       1920
tgaccccgta attgattact attannncta gcagatctgg taccgtcgat aatagtaatc       1980
aattacgggg tcattagttc atagcccata tatggagttc cgcgttacat aacttacggt       2040
aaatggcccg cctggctgac cgcccaacga cccccgccca ttgacgtcaa taatgacgta       2100
tgttcccata gtaacgccaa tagggacttt ccattgacgt caatgggtgg agtatttacg       2160
gtaaactgcc cacttggcag tacatcaagt gtatcatatg ccagtacgcc ccctattga       2220 cgtcaatgac ggtaaatggc ccgcctggca ttatgcccag tacatgacct tatgggactt       2280
tcctacttgg cagtacatct acgtattagt catcgctatt accatggtga tgcggttttg       2340
gcagtacatc aatgggcgtg atagcggttt tgactcacgg ggatttccaa gtctccaccc       2400
```

```
cattgacgtc aatgggagtt tgttttggca ccaaaaatcaa cgggactttc caaaatgtcg    2460
taacaactcc gccccattga cgcaaatggg cggtaggcgt gtacggtggg aggtctatat    2520
aagcagagct ggtttagtga accgtcagat ccgctagcat ggctgtcagc gacgcgctgc    2580
tcccatcttt ctccacgttc gcgtctggcc cggcgggaag ggagaagaca ctgcgtcaag    2640
caggtgcccc gaataaccgc tggcgggagg agctctccca catgaagcga cttcccccag    2700
tgcttcccgg ccgcccctat gacctggcgg cggcgaccgt ggccacagac ctggagagcg    2760
gcggagccgg tgcggcttgc ggcggtagca acctggcgcc cctacctcgg agagagaccg    2820
aggagttcaa cgatctcctg gacctggact ttattctctc caattcgctg acccatcctc    2880
cggagtcagt ggccgccacc gtgtcctcgt cagcgtcagc ctcctcttcg tcgtcgccgt    2940
cgagcagcgg ccctgccagc gcgccctcca cctgcagctt cacctatccg atccgggccg    3000
ggaacgaccc gggcgtggcg ccgggcggca cgggcggagg cctcctctat ggcagggagt    3060
ccgctccccc tccgacggct cccttcaacc tggcggacat caacgacgtg agcccctcgg    3120
gcggcttcat ggccgagctc ctgcggccag aattggaccc ggtgtacatt ccgccgcagc    3180
agccgcagcc gccaggtggc gggctgatgg gcaagttcgt gctgaaggcg tcgctgagcg    3240
cccctggcag cgagtacggc agcccgtcgg tcatcagcgt cagcaaaggc agccctgacg    3300
gcagccaccc ggtggtggtg gcgccctaca acggcgggcc gccgcgcacg tgccccaaga    3360
tcaagcagga ggcggtctct tcgtgcaccc acttgggcgc tggaccccct ctcagcaatg    3420
gccaccggcc ggctgcacac gacttccccc tggggcggca gctccccagc aggactaccc    3480
cgaccctggg tcttgaggaa gtgctgagca gcagggactg tcaccctgcc ctgccgcttc    3540
ctcccggctt ccatccccac ccggggccca attacccatc cttcctgccc gatcagatgc    3600
agccgcaagt cccgccgctc cattaccaag agctcatgcc accggttcc tgcatgccag    3660 aggagcccaa gccaaagagg ggaagacgat cgtggccccg gaaaaggacc gccacccaca    3720
cttgtgatta cgcgggctgc ggcaaaaacct acacaaagag ttcccatctc aaggcacacc    3780
tgcgaaccca cacaggtgag aaaccttacc actgtgactg ggacggctgt ggatggaaat    3840
tcgcccgctc agatgaactg accaggcact accgtaaaca cacggggcac cgcccgttcc    3900
agtgccaaaa atgcgaccga gcattttcca ggtcggacca cctcgcctta cacatgaaga    3960 ggcatttta agctagcgct accggactca gatcggccgc gactctagat cataatcagc    4020
cataccacat ttgtagaggt tttacttgct ttaaaaaacc tcccacacct cccctgaac    4080 ctgaaacata aaatgaatgc aattgttgtt gttaacttgt ttattgcagc ttataatggt    4140
tacaaataaa gcaatagcat cacaaatttc acaaataaag cattttttc actgcattct    4200 agttgtggtt tgtccaaact catcaatgta tcttaatcga gcggcctaa tagtaatcaa    4260 ttacggggtc attagttcat agcccatata tggagttccg cgttacataa cttacggtaa    4320
atggcccgcc tggctgaccg cccaacgacc cccgcccatt gacgtcaata atgacgtatg    4380
ttcccatagt aacgccaata gggactttcc attgacgtca atgggtggag tatttacggt    4440
aaactgccca cttggcagta catcaagtgt atcatatgcc aagtacgccc cctattgacg    4500
tcaatgacgg taaatggccc gcctggcatt atgcccagta catgacctta tgggactttc    4560
ctacttggca gtacatctac gtattagtca tcgctattac catggtgatg cggttttggc    4620
agtacatcaa tgggcgtgga tagcggtttg actcacgggg atttccaagt ctccaccccca    4680 ttgacgtcaa tgggagtttg ttttggcacc aaaatcaacg ggactttcca aaatgtcgta    4740
acaactccgc cccattgacg caaatgggcg gtaggcgtgt acggtgggag gtctatataa    4800
```

```
gcagagctgg tttagtgaac cgtcagatcc gctagcatgc ccctcaacgt tagcttcacc    4860
aacaggaact atgacctcga ctacgactcg gtgcagccgt atttctactg cgacgaggag    4920
gagaacttct accagcagca gcagcagagc gagctgcagc cccggcgcc cagcgaggat     4980 atctggaaga aattcgagct gctgccacc ccgcccctgt ccctagccg ccgctccggg      5040 ctctgctcgc cctcctacgt tgcggtcaca cccttctccc ttcggggaga caacgacggc    5100
ggtggcggga gcttctccac ggccgaccag ctggagatgg tgaccgagct gctgggagga    5160
gacatggtga accagagttt catctgcgac ccggacgacg agaccttcat caaaaacatc    5220
atcatccagg actgtatgtg gagcggcttc tcggccgccg ccaagctcgt ctcagagaag    5280
ctggcctcct accaggctgc gcgcaaagac agcggcagcc cgaaccccgc ccgcggccac    5340
agcgtctgct ccacctccag cttgtacctg caggatctga gcgccgccgc ctcagagtgc    5400
atcgacccct cggtggtctt cccctaccct ctcaacgaca gcagctcgcc caagtcctgc    5460
gcctcgcaag actccagcgc cttctctccg tcctcggatt ctctgctctc ctcgacggag    5520
tcctccccgc agggcagccc cgagcccctg gtgctccatg aggagacacc gcccaccacc    5580
agcagcgact ctgaggagga acaagaagat gaggaagaaa tcgatgttgt ttctgtggaa    5640
aagaggcagg ctcctggcaa aaggtcagag tctggatcac cttctgctgg aggccacagc    5700
aaacctcctc acagcccact ggtcctcaag aggtgccacg tctccacaca tcagcacaac    5760
tacgcagcgc ctccctccac tcggaaggac tatcctgctg ccaagagggt caagttggac    5820
agtgtcagag tcctgagaca gatcagcaac aaccgaaaat gcaccagccc caggtcctcg    5880
gacaccgagg agaatgtcaa gaggcgaaca cacaacgtct tggagcgcca gaggaggaac    5940
gagctaaaac ggagcttttt tgccctgcgt gaccagatcc cggagttgga aaacaatgaa    6000
aaggccccca aggtagttat ccttaaaaaa gccacagcat acatcctgtc cgtccaagca    6060
gaggagcaaa agctcatttc tgaagaggac ttgttgcgga acgacgaga acagttgaaa     6120 cacaaacttg aacagctacg gaactcttgt gcgtaagcta gcgctaccgg actcagatcg    6180
gccgcgactc tagatcataa tcagccatac cacatttgta gaggttttac ttgctttaaa    6240
aaacctccca cacctccccc tgaacctgaa acataaaatg aatgcaattg ttgttgttaa    6300
cttgtttatt gcagcttata atggttacaa ataaagcaat agcatcacaa atttcacaaa    6360
taaagcattt ttttcactgc attctagttg tggtttgtcc aaactcatca atgtatctta    6420
aggccgcgat taatagtaat caattacggg gtcattagtt catagcccat atatggagtt    6480
ccgcgttaca taacttacgg taaatggccc gcctggctga ccgcccaacg accccgcc     6540 attgacgtca ataatgacgt atgttcccat agtaacgcca atagggactt tccattgacg    6600
tcaatgggtg gagtatttac ggtaaactgc ccacttggca gtacatcaag tgtatcatat    6660
gccaagtacg ccccctattg acgtcaatga cggtaaatgg cccgcctggc attatgccca    6720
gtacatgacc ttatgggact ttcctacttg gcagtacatc tacgtattag tcatcgctat    6780
taccatggtg atgcggtttt ggcagtacat caatgggcgt ggatagcggt ttgactcacg    6840
gggatttcca agtctccacc ccattgacgt caatgggagt tgttttggc accaaaatca     6900 acgggacttt ccaaaatgtc gtaacaactc cgccccattg acgcaaatgg gcggtaggcg    6960
tgtacggtgg gaggtctata taagcagagc tggtttagtg aaccgtcaga tccgctagca    7020
tggcgggaca cctggcttcg gatttcgcct tctcgccccc tccaggtggt ggaggtgatg    7080
ggccaggggg gccggagccg ggctgggttg atcctcggac ctggctaagc ttccaaggcc    7140
```

```
ctcctggagg gccaggaatc gggccggggg ttgggccagg ctctgaggtg tgggggattc    7200
ccccatgccc ccgccgtat  gagttctgtg gggggatggc gtactgtggg cccaggttg    7260
gagtggggct agtgccccaa ggcggcttgg agacctctca gcctgagggt gaagcangag    7320
tcggggtgga gagcaactcc gatggggcct cccggagcc  ctgcaccgtc accctggtg    7380
ccgtgaagct ggagaaggag aagctggagc aaaacccgga ggagtccag  acatcaaag    7440
ctctgcagaa agaactcgag caatttgcca agctcctgaa gcagaagagg atcaccctgg    7500
gatatacaca ggccgatgtg gggctcaccc tggggttct  atttgggaag gtattcagcc    7560
aaacgaccat ctgccgcttt gaggctctgc agcttagctt caagaacatg tgtaagctgc    7620
ggcccttgct gcagaagtgg gtggaggaag ctgacaacaa tgaaaatctt caggagatat    7680
gcaaagcaga acccctcgtg caggcccgaa agagaaagcg aaccagtatc gagaaccgag    7740
tgagaggcaa cctggagaat tgttcctgc  agtgcccgaa acccacactg cagcagatca    7800
gccacatcgc ccagcagctt gggctcgaga aggatgtggt ccgagtgtgg ttctgtaacc    7860
ggcgccagaa gggcaagcga tcaagcagcg actatgcaca acgagaggat tttgaggctg    7920
ctgggtctcc tttctcaggg ggaccagtgt cctttcctct ggcccaggg  ccccatttg    7980
gtacccagg  ctatgggagc cctcacttca ctgcactgta ctcctcggtc cctttccctg    8040
agggggaagc ctttccccct gtctccgtca ccactctggg ctctcccatg cattcaaact    8100
gagctagcgc taccggactc agatcggccg cgactctaga tcataatcag ccataccaca    8160
tttgtagagg ttttacttgc tttaaaaaac ctcccacacc tcccctgaa  cctgaaacat    8220
aaaatgaatg caattgttgt tgttaacttg tttattgcag cttataatgg ttacaaataa    8280
agcaatagca tcacaaattt cacaaataaa gcattttttt cactgcattc tagttgtggt    8340
ttgtccaaac tcatcaatgt atcttaaatc ctcgagaagc ttaatagtaa tcaattacgg    8400
ggtcattagt tcatagccca tatatggagt tccgcgttac ataacttacg gtaaatggcc    8460
cgcctggctg accgcccaac gacccccgcc cattgacgtc aataatgacg tatgttccca    8520
tagtaacgcc aatagggact ttccattgac gtcaatgggt ggagtattta cggtaaactg    8580
cccacttggc agtacatcaa gtgtatcata tgccaagtac gccccctatt gacgtcaatg    8640
acggtaaatg gcccgcctgg cattatgccc agtacatgac cttatgggac tttcctactt    8700
ggcagtacat ctacgtatta gtcatcgcta ttaccatggt gatgcggttt tggcagtaca    8760
tcaatgggcg tggatagcgg tttgactcac ggggatttcc aagtctccac cccattgacg    8820
tcaatggag  tttgttttgg caccaaaatc aacgggactt tccaaaatgt cgtaacaact    8880
ccgccccatt gacgcaaatg gcggtaggc  gtgtacggtg ggaggtctat ataagcagag    8940
ctggtttagt gaaccgtcag atccgctagc atgtacaaca tgatggagac ggagctgaag    9000
ccgccgggcc cgcagcaaac ttcggggggc ggcggcggca actccaccgc ggcggcggcc    9060
ggcggcaacc agaaaaacag cccggaccgc gtcaagcggc ccatgaatgc cttcatggtg    9120
tggtcccgcg gcagcggcg  caagatggcc caggagaacc caagatgca  caactcggag    9180
atcagcaagc gcctgggcgc cgagtggaaa cttttgtcgg agacggagaa gcggccgttc    9240
atcgacgagg ctaagcggct gcgagcgctg cacatgaagg agcacccgga ttataaatac    9300
cggccccgg  ggaaaaccaa gacgctcatg aagaaggata agtacacgct gccccggcgg    9360
ctgctgccc  ccggcggcaa tagcatggc  agcgggtcg  gggtgggcgc cggcctgggc    9420
gcgggcgtga accagcgcat ggacagttac gcgcacatga acggctggag caacggcagc    9480
tacagcatga tgcaggacca gctgggctac ccgcagcacc cgggcctcaa tgcgcacggc    9540
```

```
gcagcgcaga tgcagcccat gcaccgctac gacgtgagcg ccctgcagta caactccatg    9600
accagctcgc agacctacat gaacggctcg cccaccctaca gcatgtccta ctcgcagcag    9660 ggcaccctg gcatggctct tggctccatg ggttcggtgg tcaagtccga ggccagctcc     9720 agccccctg tggttacctc ttcctcccac tccagggcgc cctgccaggc cggggacctc    9780
cgggacatga tcagcatgta tctccccggc gccgaggtgc cggaacccgc cgcccccagc    9840
agacttcaca tgtcccagca ctaccagagc ggcccggtgc ccggcacggc cattaacggc    9900
acactgcccc tctcacacat gtgagctagc gctaccggac tcagatcggc cgcgactcta    9960
gatcataatc agccatacca catttgtaga ggttttactt gctttaaaaa acctcccaca   10020 cctcccctg aacctgaaac ataaaatgaa tgcaattgtt gttgttaact tgtttattgc   10080
agcttataat ggttacaaat aaagcaatag catcacaaat ttcacaaata aagcattttt   10140
ttcactgcat tctagttgtg gtttgtccaa actcatcaat gtatcttaaa gctttctaga   10200
gnnntaaggg tgggaaagaa tatataaggt gggggtctta tgtagttttg tatctgtttt   10260
gcagcagccg ccgccgccat gagcaccaac tcgtttgatg gaagcattgt gagctcatat   10320
ttgacaacgc gcatgccccc atgggccggg gtgcgtcaga atgtgatggg ctccagcatt   10380
gatggtcgcc ccgtcctgcc cgcaaactct actaccttga cctacgagac cgtgtctgga   10440
acgccgttgg agactgcagc ctccgccgcc gcttcagccg ctgcagccac cgcccgcggg   10500
attgtgactg actttgcttt cctgagcccg cttgcaagca gtgcagcttc ccgttcatcc   10560
gcccgcgatg acaagttgac ggctcttttg gcacaattgg attctttgac ccgggaactt   10620
aatgtcgttt ctcagcagct gttggatctg cgccagcagg tttctgccct gaaggcttcc   10680
tcccctccca atgcggttta aaacataaat aaaaaaccag actctgtttg gatttggatc   10740
aagcaagtgt cttgctgtct ttatttaggg gttttgcgcg cgcggtaggc ccgggaccag   10800
cggtctcggt cgttgagggt cctgtgtatt ttttccagga cgtggtaaag gtgactctgg   10860
atgttcagat acatgggcat aagcccgtct ctggggtgga ggtagcacca ctgcagagct   10920
tcatgctgcg gggtggtgtt gtagatgatc cagtcgtagc aggagcgctg ggcgtggtgc   10980
ctaaaaatgt ctttcagtag caagctgatt gccaggggca ggcccttggt gtaagtgttt   11040
acaaagcggt taagctggga tgggtgcata cgtggggata tgagatgcat cttgactgt   11100 attttaggt tggctatgtt cccagccata tccctccggg gattcatgtt gtgcagaacc   11160
accagcacag tgtatccggt gcacttggga aatttgtcat gtagcttaga aggaaatgcg   11220
tggaagaact tggagacgcc cttgtgacct ccaagatttt ccatgcattc gtccataatg   11280
atggcaatgg gcccacgggc ggcggcctgg gcgaagatat ttctgggatc actaacgtca   11340
tagttgtgtt ccaggatgag atcgtcatag gccatttta caaagcgcgg gcggagggtg   11400
ccagactgcg gtataatggt tccatccggc ccaggggcgt agttaccctc acagatttgc   11460
atttcccacg ctttgagttc agatgggggg atcatgtcta cctgcgggc gatgaagaaa   11520 acggtttccg gggtagggga gatcagctgg gaagaaagca ggttcctgag cagctgcgac   11580
ttaccgcagc cggtgggccc gtaaatcaca cctattaccg ggtgcaactg gtagttaaga   11640
gagctgcagc tgccgtcatc cctgagcagg ggggccactc cgttaagcat gtccctgact   11700
cgcatgtttt ccctgaccaa atccgccaga aggcgctcgc cgcccagcga tagcagttct   11760
tgcaaggaag caaagttttt caacggtttg agaccgtccg ccgtaggcat gcttttgagc   11820
gtttgaccaa gcagttccag gcggtcccac agctcggtca cctgctctac ggcatctcga   11880
```

```
tccagcatat ctcctcgttt cgcgggttgg ggcggctttc gctgtacggc agtagtcggt    11940
gctcgtccag acgggccagg gtcatgtctt tccacgggcg cagggtcctc gtcagcgtag    12000
tctgggtcac ggtgaagggg tgcgctccgg gctgcgcgct ggccagggtg cgcttgaggc    12060
tggtcctgct ggtgctgaag cgctgccggt cttcgccctg cgcgtcggcc aggtagcatt    12120
tgaccatggt gtcatagtcc agcccctccg cggcgtggcc cttggcgcgc agcttgccct    12180
tggaggaggc gccgcacgag gggcagtgca gacttttgag ggcgtagagc ttgggcgcga    12240
gaaataccga ttccggggag taggcatccg cgccgcaggc cccgcagacg gtctcgcatt    12300
ccacgagcca ggtgagctct ggccgttcgg ggtcaaaaac caggtttccc ccatgctttt    12360
tgatgcgttt cttacctctg gtttccatga gccggtgtcc acgctcggtg acgaaaaggc    12420
tgtccgtgtc cccgtataca gactnnngtt taaacgaatt cnnntataaa atgcaaggtg    12480
ctgctcaaaa aatcaggcaa agcctcgcgc aaaaagaaa gcacatcgta gtcatgctca    12540
tgcagataaa ggcaggtaag ctccggaacc accacagaaa aagacaccat ttttctctca    12600
aacatgtctg cgggtttctg cataaacaca aaataaaata acaaaaaaac atttaaacat    12660
tagaagcctg tcttacaaca ggaaaaacaa cccttataag cataagacgg actacggcca    12720
tgccggcgtg accgtaaaaa aactggtcac cgtgattaaa aagcaccacc gacagctcct    12780
cggtcatgtc cggagtcata atgtaagact cggtaaacac atcaggttga ttcatcggtc    12840
agtgctaaaa agcgaccgaa atagcccggg ggaatacata cccgcaggcg tagagacaac    12900
attacagccc ccataggagg tataacaaaa ttaataggag agaaaaacac ataaacacct    12960
gaaaaaccct cctgcctagg caaaatagca ccctcccgct ccagaacaac atacagcgct    13020
tcacagcggc agcctaacag tcagccttac cagtaaaaaa gaaaacctat taaaaaaaca    13080
ccactcgaca cggcaccagc tcaatcagtc acagtgtaaa aaagggccaa gtgcagagcg    13140
agtatatata ggactaaaaa atgacgtaac ggttaaagtc cacaaaaaac acccagaaaa    13200
ccgcacgcga acctacgccc agaaacgaaa gccaaaaaac ccacaacttc ctcaaatcgt    13260
cacttccgtt ttcccacgtt acgtaacttc ccattttaag aaaactacaa ttcccaacac    13320
atacaagtta ctccgcccta aaacctacgt caccccgcccc gttcccacgc cccgcgccac    13380
gtcacaaact ccaccccctc attatcatat tggcttcaat ccaaaataag gtatattatt    13440
gatgatnnnt taattaagga tccnnncggt gtgaaatacc gcacagatgc gtaaggagaa    13500
aataccgcat caggcgctct tccgcttcct cgctcactga ctcgctgcgc tcggtcgttc    13560
ggctgcggcg agcggtatca gctcactcaa aggcggtaat acggttatcc acagaatcag    13620
gggataacgc aggaaagaac atgtgagcaa aaggccagca aaaggccagg aaccgtaaaa    13680
aggccgcgtt gctggcgttt ttccataggc tccgccccccc tgacgagcat cacaaaaatc    13740
gacgctcaag tcagaggtgg cgaaacccga caggactata aagataccag gcgtttcccc    13800
ctggaagctc cctcgtgcgc tctcctgttc cgaccctgcc gcttaccgga tacctgtccg    13860
cctttctccc ttcgggaagc gtggcgcttt ctcatagctc acgctgtagg tatctcagtt    13920
cggtgtaggt cgttcgctcc aagctgggct gtgtgcacga accccccgtt cagcccgacc    13980
gctgcgcctt atccggtaac tatcgtcttg agtccaaccc ggtaagacac gacttatcgc    14040
cactggcagc agccactggt aacaggatta gcagagcgag gtatgtaggc ggtgctacag    14100
agttcttgaa gtggtggcct aactacggct acactagaag gacagtattt ggtatctgcg    14160
ctctgctgaa gccagttacc ttcggaaaaa gagttggtag ctcttgatcc ggcaaacaaa    14220
ccaccgctgg tagcggtggt ttttttgttt gcaagcagca gattacgcgc agaaaaaaag    14280
```

-continued

```
gatctcaaga agatcctttg atcttttcta cggggtctga cgctcagtgg aacgaaaact  14340
cacgttaagg gattttggtc atgagattat caaaaaggat cttcacctag atccttttaa  14400
attaaaaatg aagttttaaa tcaatctaaa gtatatatga gtaaacttgg tctgacagtt  14460
accaatgctt aatcagtgag gcacctatct cagcgatctg tctatttcgt tcatccatag  14520
ttgcctgact ccccgtcgtg tagataacta cgatacggga gggcttacca tctggcccca  14580
gtgctgcaat gataccgcga gacccacgct caccggctcc agatttatca gcaataaacc  14640
agccagccgg aagggccgag cgcagaagtg gtcctgcaac tttatccgcc tccatccagt  14700
ctattaattg ttgccgggaa gctagagtaa gtagttcgcc agttaatagt ttgcgcaacg  14760
ttgttgnnnn nnaaaaagga tcttcaccta gatccttttc acgtagaaag ccagtccgca  14820
gaaacggtgc tgaccccgga tgaatgtcag ctactgggct atctggacaa gggaaaacgc  14880
aagcgcaaag agaaagcagg tagcttgcag tgggcttaca tggcgatagc tagactgggc  14940
ggttttatgg acagcaagcg aaccggaatt gccagctggg gcgccctctg gtaaggttgg  15000
gaagccctgc aaagtaaact ggatggcttt ctcgccgcca aggatctgat ggcgcagggg  15060
atcaagctct gatcaagaga caggatgagg atcgtttcgc atgattgaac aagatggatt  15120
gcacgcaggt tctccggccg cttgggtgga gaggctattc ggctatgact gggcacaaca  15180
gacaatcggc tgctctgatg ccgccgtgtt ccggctgtca gcgcaggggc gcccggttct  15240
ttttgtcaag accgacctgt ccggtgccct gaatgaactg caagacgagg cagcgcggct  15300
atcgtggctg gccacgacgg gcgttccttg cgcagctgtg ctcgacgttg tcactgaagc  15360
gggaagggac tggctgctat tgggcgaagt gccggggcag gatctcctgt catctcacct  15420
tgctcctgcc gagaaagtat ccatcatggc tgatgcaatg cggcggctgc atacgcttga  15480
tccggctacc tgcccattcg accaccaagc gaaacatcgc atcgagcgag cacgtactcg  15540
gatggaagcc ggtcttgtcg atcaggatga tctggacgaa gagcatcagg ggctcgcgcc  15600
agccgaactg ttcgccaggc tcaaggcgag catgcccgac ggcgaggatc tcgtcgtgac  15660
ccatggcgat gcctgcttgc cgaatatcat ggtggaaaat ggccgctttt ctggattcat  15720
cgactgtggc cggctgggtg tggcggaccg ctatcaggac atagcgttgg ctacccgtga  15780
tattgctgaa gagcttggcg gcgaatgggc tgaccgcttc ctcgtgcttt acggtatcgc  15840
cgctcccgat tcgcagcgca tcgccttcta tcgccttctt gacgagttct tctgaatttt  15900
gttaaatttt ttgttaaatc agctcatttt ttaaccaata ggccgaaatc ggcaacatcc  15960
cttataaatc aaaagaatag accgcgatag ggttgagtgt tgttccagtt tggaacaaga  16020
gtccactatt aaagaacgtg gactccaacg tcaaagggcg aaaaaccgtc tatcagggcg  16080
atggcccact acgtgaacca tcacccaaat caagtttttt gcggtcgagg tgccgtaaag  16140
ctctaaatcg aaccctaaa gggagccccc gatttagagc ttgacgggga agccggcga   16200
acgtggcgag aaaggaaggg aagaaagcga aggagcggg cgctagggcg ctggcaagtg   16260
tagcggtcac gctgcgcgta accaccacac ccgcgcgctt aatgcgccg               16309
```